(12) United States Patent
Wendlandt et al.

(10) Patent No.: US 11,618,763 B2
(45) Date of Patent: Apr. 4, 2023

(54) SELECTIVE VALORIZATION OF BIOMASS SUGARS

(71) Applicant: Massachusetts Institute of Technology, Cambridge, MA (US)

(72) Inventors: Alison Wendlandt, Cambridge, MA (US); Yong Wang, Brookline, MA (US); Hayden Carder, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 17/129,399

(22) Filed: Dec. 21, 2020

(65) Prior Publication Data
US 2021/0188890 A1  Jun. 24, 2021

Related U.S. Application Data

(60) Provisional application No. 62/950,584, filed on Dec. 19, 2019.

(51) Int. Cl.
| | |
|---|---|
| *C07H 1/00* | (2006.01) |
| *C07H 3/02* | (2006.01) |
| *C07H 3/06* | (2006.01) |
| *B01J 31/02* | (2006.01) |
| *B01J 31/18* | (2006.01) |

(52) U.S. Cl.
CPC ............ *C07H 1/00* (2013.01); *B01J 31/0244* (2013.01); *B01J 31/181* (2013.01); *C07H 3/02* (2013.01); *C07H 3/06* (2013.01)

(58) Field of Classification Search
CPC ..... C07H 1/00; C07H 3/02; C07H 3/06; B01J 31/0244; B01J 31/181
See application file for complete search history.

(56) References Cited

U.S. PATENT DOCUMENTS

| | | |
|---|---|---|
| 2,001,788 A | 5/1935 | Leaper et al. |
| 5,612,371 A | 3/1997 | Danvy et al. |
| 2014/0004570 A1 | 1/2014 | Medoff et al. |

FOREIGN PATENT DOCUMENTS

WO  WO-2021/127642 A1  6/2021

OTHER PUBLICATIONS

De et al., Catal. Sci. Technol., 2016, 6, p. 7364-7385. (Year: 2016).*
Capaldo et al., Eur. J. Org. Chem., 2017, 2056-2071. (Year: 2017).*
Chong et al., Journal of Catalysis, 2014, 314, p. 101-108. (Year: 2014).*
Wang et al., "Synthesis of rare sugar isomers through site-selective epimerization," Nature, 578: 403-408 (2020).
Wendlandt., "Site-selective functionalization reactions of carbohydrates," Massachusetts Institute of Technology Chemistry, ACS San Diego: 47 pages (2019).
Banerjee et al., Boron trifluoride etherate in organic synthesis, MOJ Bioorganic & Organic Chemistry, 3(1): 1-9 (2019).
Da Vià et al., "Visible light selective photocatalytic conversion of glucose by TiO2," Applied Catalysis B: Environmental, 202: 281-288 (2017).
Delidovich et al., "Catalytic Isomerization of Biomass-Derived Aldoses: A Review," ChemSusChem, 9: 547-561 (2016).
Gunther et al., "Sn-Beta zeolites with borate salts catalyse the epimerization of carbohydrates via an intramolecular carbon shift," Nature Communications, 3:1109 (2012).
International Search Report and Written Opinion for International Application No. PCT/US20/66433 dated Mar. 15, 2021.
Lanziano et al., "Catalytic Conversion of Glucose Using TiO2 Catalysts," Chemical Engineering Transactions, 37: 589-594 (2014).
Wang et al., "H3PMo12O40 Immobilized on Amine Functionalized SBA-15 as a Catalyst for Aldose Epimerization," Materials, 13: 507 (2020).
Wang et al., "Regioselective 1,2-Diol Rearrangement by Controlling the Loading of BF3•Et2O and its Application to the Synthesis of Related Nor-Sesquiterene- and Sesquiterene-Type Marine Natural Products," Organic Letters, 19(14): 3811-3814 (2017).

* cited by examiner

*Primary Examiner* — Jonathan S Lau
(74) *Attorney, Agent, or Firm* — Foley Hoag LLP; Dana M. Gordon; Alexander J. Chatterley

(57) ABSTRACT

Disclosed are methods of forming an epimer or a dehydrated isomer of a pyranose monosaccharide or a pyranose saccharide residue in an oligosaccharide or a glycoside.

20 Claims, 25 Drawing Sheets a. Biomass-derived monosaccharides (5 total)
- obtained from cellulose, hemicellulose

*D-glucose* $0.02/mol

*D-galactose* $10/mol

*D-mannose* $10/mol

*D-xylose* $1/mol

*L-arabinose* $10/mol b. "Rare" monosaccharides (>500 total)
- cannot be isolated from natural sources

*D-allose* $90,000/mol

*D-talose* $160,000/mol

*L-ribose* $60,000/mol

*L-gulose* (c.f. bleomycin)

*D-digitoxose* (c.f. digoxin)

C. Chemical and enzymatic isomerizations proceed through polar aldose-ketose mechanisms

*Lobry de Bruyn-Alberda van Ekenstein Reaction:*

*"Izumoring" enzymatic isomerization:*

Limitations:
• equilibrium control
• low overall yields/selectivities
• high production costs d. Proposed enzymatic radical epimerization pathway in the biosynthesis of Neomycin B by NeoN a. Product does not equilibrate with starting material b. Deuterium incorporation study

| entry | Catalyst | ox? | red. | yield |
|---|---|---|---|---|
| II-135a | 4,4'-D'Bu | 1.21 v | -1.37 v | 48% |
| II-137a | 5,5'-DiCF₃ | 1.68 v | 0.69 v | 18% |
| II-137b | 5,5'-DiMe | | | 30% |
| II-137c | 4,4'-DiMeO | | | 23% |
| II-137d | 4,4'-DiMe | | | 21% |
| II-137e | H | 0.97 v | | 14% |
| II-137f | phenanthroline | 1.39 v | | <1% |
| II-137g | Ir(PPy)₃ | | | <1% |
| II-138a | H | 0.61 v | | 2% |
| II-138b | 4,4'-DiMe | | | 4% |
| II-138c | 4,4'-DiMeO | 0.59 v | | 2% |
| II-138d | 4,4'-D'Bu | | | 3% |
| II-138e | 5,5'-DiMe | 0.61 v | | 5% |
| II-138f | 5,5'-DiCF₃ | 0.74 v | | <1% |
| II-138g | Ru(bpy)₃Cl·5H₂O | 0.31 v | | <1% |
| II-138l | Ru(dtbpy)₃(PF₆)₂ | | | <1% |

| Entry | Catalyst | $E_{ox}$ | $E_{red}$ | Yield |
|---|---|---|---|---|
| II-135a | [Ir(dF(CF3)ppy)2(dtbbpy)]PF6 | 1.21 v | -1.37 v | 48% |
| II-138h | Eosin-Y | 0.79 v | -1.06 v | <1% |
| II-138j | Methylene Blue | 0.5 v | -0.11 v | <1% |
| II-138k | Mes-Acr | 2.06 v | -0.57 v | <1% |
| II-138m/152b | 4CzIPN | 1.35 v | -1.21 v | 47%/55% |
| II-152c | 4CzIPN, w/o TBAOBz | | | 24% |
| II-152d | 4CzPN | 1.40 v | -1.16 v | 20% |
| II-152e | 4CzPN, w/o TBAOBz | | | 16% |
| II-138a | 4CzTPN | 1.41 v | -1.02 v | 23% |
| II-146b | DCA | 1.97 v | -0.97 v | <1% |

FIG. 4D

Hydrogen Donor Source glucose (1) + R-SH (2, 25 mol%) → allose (3)

Conditions: [Ir(dF(CF₃)ppy)₂(dtbbpy)]PF₆ (1 mol %), Quinuclidine (10 mol %), TBAOBz (25 mol %), MeCN/DMSO 10/1; RT; 22 h, Sigma blue LED

| Entry | Thiol | pKa (in DMSO) | BDE (kcal/mol) | Yield |
|---|---|---|---|---|
| II-140j | PhC(O)SH | 5.2 | 87 | <1% |
| II-116a | PhSH | 10.3 | 79 | NR |
| II-116d | 2,6-DiMeC₆H₃SH | 11.6 | 80 | NR |
| II-134c | 4-MeOBnSH | 16.3 | 88 | <1% |
| II-140h | Mes-CH₂SH | ~16 | ~88 | <1% |
| II-134d | PhCH₂CH₂SH | 16.4 | ~87 | 29% |
| II-143a | EtOC(O)CH₂CH₂SH | 16.6 | ~87 | 17% |
| II-134a | nC₆H₁₃SH | 16.7 | 87 | 26% |
| II-134b | nC₁₂H₂₅SH | 17.6 | 88 | 34% |
| II-124c | CySH | 17.7 | 87 | 38% |
| II-116c | 1-Adamantanethiol | 17.9 | ~87 | 52% |
| II-122f | tert-BuSH | 17.9 | 87 | 15% |
| II-143b | (tert-BuS)₂ | - | 65 (S-S) | 3% |
| II-140l | L-cysteine | 2.0 | 86 | 6% |
| II-124a | Ph₃CSH | - | ~88 | NR |
| II-124b | Ph₃SiSH | - | - | NR |

FIG. 4E

*Further Optimization with Kessil Blue*

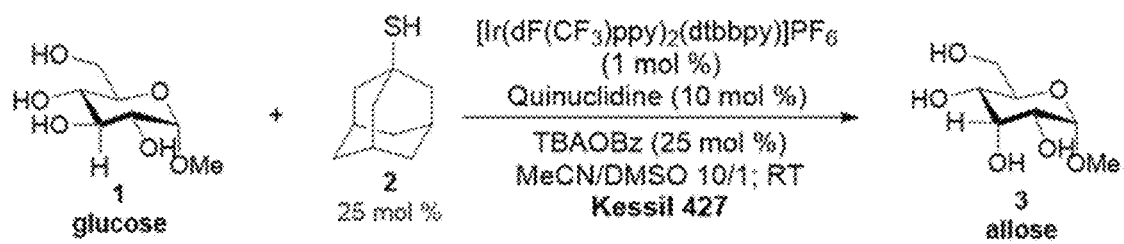

| entry | conditions | yield |
|---|---|---|
| II-129a/141a | Standard, 18 h | 57%/66% |
| II-149a | 10 mol% [SH] | 57% |
| II-149b | 20 mol% [SH] | 65% |
| II-141b/144a/149c | 30 mol% [SH] | 66%/80%/77% |
| II-141c/144b/149d | 40 mol% [SH] | 75%/81%/88% |
| II-139b/144c/170a | 50 mol% [SH] | 86%/80%/88% |
| II-139a | 50 mol% [SH], no base | 82% |
| II-144d | 20 mol% [Q] | 86% |
| II-151c | 4CzIPN as Cat.; 25 mol% [SH] | 77% |
| II-151d | 4CzIPN as Cat.; 50 mol% [SH] | 89% |
| II-151c | 4CzIPN as Cat.; 25 mol% [SH]; no base | 30% |
| II-151d | 4CzIPN as Cat.; 50 mol% [SH]; no base | 29% |
| II-152f | 4CzPN as Cat.; 50 mol% [SH] | 23% |
| II-170d | 4CzTPN as Cat.; 50 mol% [SH] | 23% |

*Base Effect*

| entry | base | yield |
|---|---|---|
| II-130a | NaOAc | 33% |
| II-130b | KOAc | 37% |
| II-130c | CsOAc | 38% |
| II-130d | Bu₄NOAc | 28% |
| II-130e | PhCO₂Na | 21% |
| II-130f | PhCO₂K | 39% |
| II-172g | Bu₄NOBz | 48% |
| II-130g | A | 31% |
| II-130h | B | 13% |
| II-130i | C | 39% |
| II-130j | D | 27% |

SELECTIVE VALORIZATION OF BIOMASS SUGARS

RELATED APPLICATIONS

This application claims the benefit of priority to U.S. Provisional Application Ser. No. 62/950,584, filed Dec. 19, 2019.

BACKGROUND

Glycans have diverse physiological functions, ranging from energy storage and structural integrity to cell signaling and the regulation of intracellular processes. Simple structural and storage polymers including starch, cellulose, and hemicellulose are important sources of the monosaccharide feedstocks (D)-glucose, (D)-xylose, (D)-galactose, (D)-mannose, and (L)-arabinose (FIG. 1A). These five biomass-derived monosaccharides are extracted on commercial scales, and serve as renewable chemical feedstocks and building blocks. There are, however, many hundreds of distinct monosaccharides that cannot be efficiently obtained from their natural sources and must instead be prepared through multistep chemical or chemoenzymatic synthesis (FIG. 1). These so-called "rare sugars" feature prominently in biologically-active natural products and pharmaceutical compounds, notably including numerous FDA-approved antiviral, antibacterial, anti-cancer and cardiac drugs. Thus, there remains an ongoing need for new methods for forming "rare sugars".

SUMMARY

In one aspect, the present disclosure provides methods of forming an epimer of a pyranose monosaccharide or a pyranose saccharide residue in an oligosaccharide or a glycoside, represented by the following scheme:

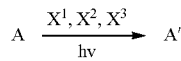

wherein,
A is a pyranose monosaccharide or a pyranose saccharide residue in an oligosaccharide or a glycoside;
A' is an epimer of A, wherein the stereochemical configuration of a chiral center bearing a hydroxyl moiety in A' is inverted relative to the stereochemical configuration of the chiral center in A;
$X^1$ is a photocatalyst;
$X^2$ is an amine;
$X^3$ is a hydrogen atom donor; and
hv is light.

In another aspect, the present disclosure provides methods of deoxygenating a pyranose monosaccharide or a pyranose saccharide residue in an oligosaccharide or a glycoside, represented by the following scheme:

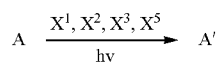

wherein,
A is a pyranose monosaccharide or a pyranose saccharide residue in an oligosaccharide or a glycoside;
A' is a dehydrated isomer of A; wherein A' comprises a —C(O)—CH$_2$— moiety at a location that is —CH(OH)—CH(OH)— in A;
$X^1$ is a photocatalyst;
$X^2$ is a base or absent;
$X^3$ is a hydrogen atom donor;
$X^5$ is a Lewis acid; and
hv is light.

BRIEF DESCRIPTION OF THE DRAWINGS

FIG. 4D depicts exemplary reactions performed with different hydrogen donor sources.

FIG. 4E depicts exemplary reactions performed with different conditions.

DETAILED DESCRIPTION OF THE INVENTION

Figure 1A:
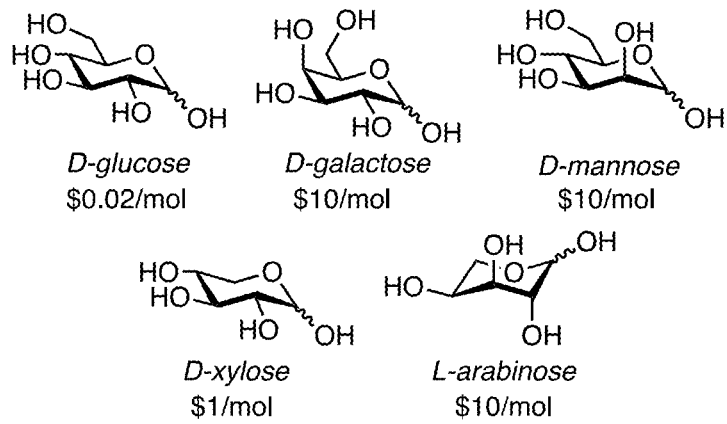
FIG. 1A depicts exemplary biomass-derived monosaccharides.
Figure 1B:
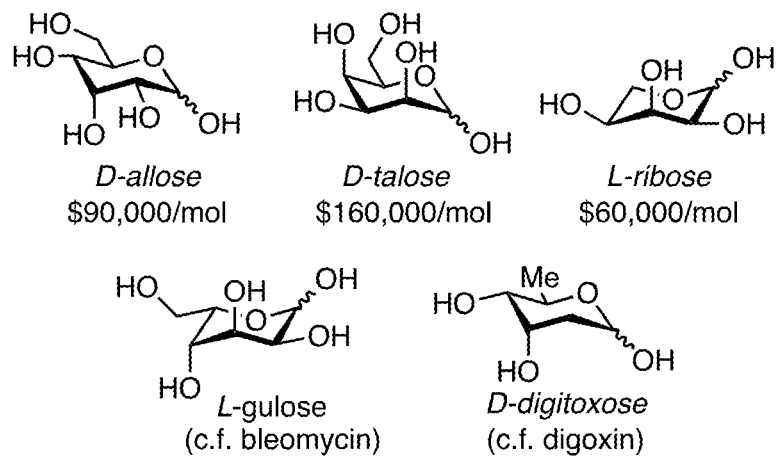
FIG. 1B depicts exemplary "rare" monosaccharides.
Figure 1C:
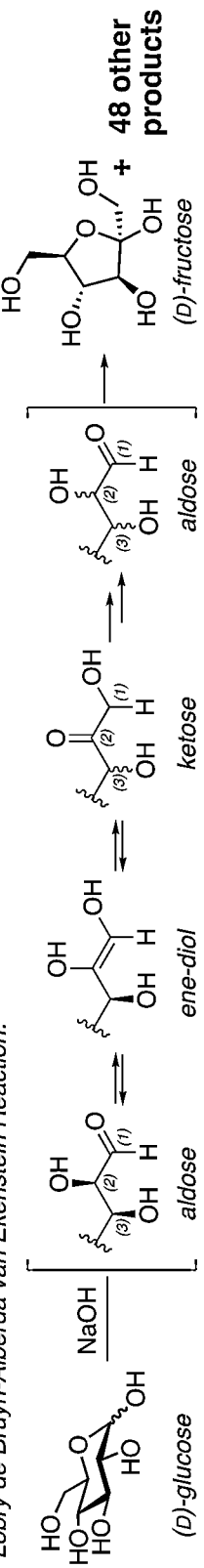
FIG. 1C depicts a known method for preparing certain sugars.
Figure 1C:
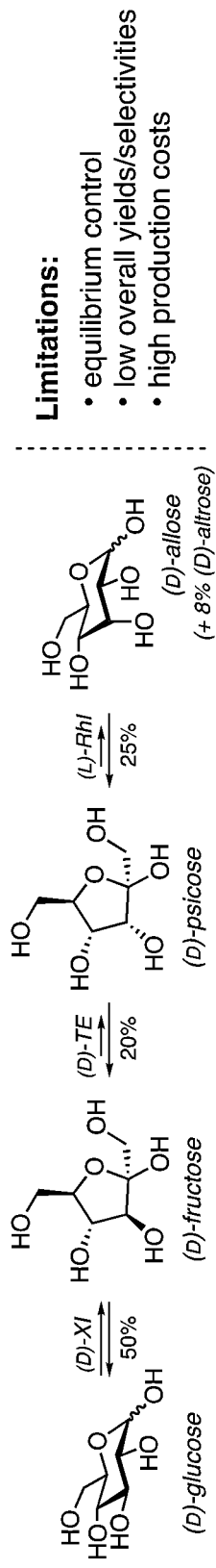

Isomerization is an important strategy for the synthesis of rare sugars from biomass precursors; however, these processes remain challenging due to the structural and stereochemical complexity of sugars. Chemical isomerization reactions (for example, the Lobry de Bruyn-Alberda van Ekenstein and Bilik reactions) are typically unselective, leading to complex thermodynamic distributions of products and often intractable separations (FIG. 1C). In contrast, enzymatic methods offer an added level of precision and have emerged as a powerful synthetic alternative to chemical strategies. Enzymatic isomerizations feature prominently in industrial sugar processing, including in the syntheses of (D)-fructose and (D)-ribose from (D)-glucose. In principle, multistep enzymatic synthesis also provides synthetic access to the rare hexose, pentose, and tetrose isomers; low yields and prohibitive production costs nonetheless limit implementation of these strategies. For example, (D)-allose has potential value as low-glycemic sweetener and shows promising anti-inflammatory and immunosuppressive activity. The enzymatic synthesis of (D)-allose can be achieved in overall 2.5% yield from (D)-glucose through sequential treatment with (D)-xylose isomerase (D-XI, 50% yield), (D)-tagatose 3-epimerase (D-TE, 20% yield), and (L)-rhamnose isomerase (L-RhI, 25% yield allose+8% yield altrose) (FIG. 1C). Like chemical isomerizations, nearly all enzymatic isomerizations proceed through reversible polar enolization mechanisms under equilibrium control. Maximum product yields are therefore dictated by thermodynamic considerations under reaction conditions constrained by temperature-dependent enzyme activity. Reaction scope is also mechanistically restricted: for example, 2-deoxygenated sugars cannot be substrates under enolization-based isomerization conditions.

Figure 1D:
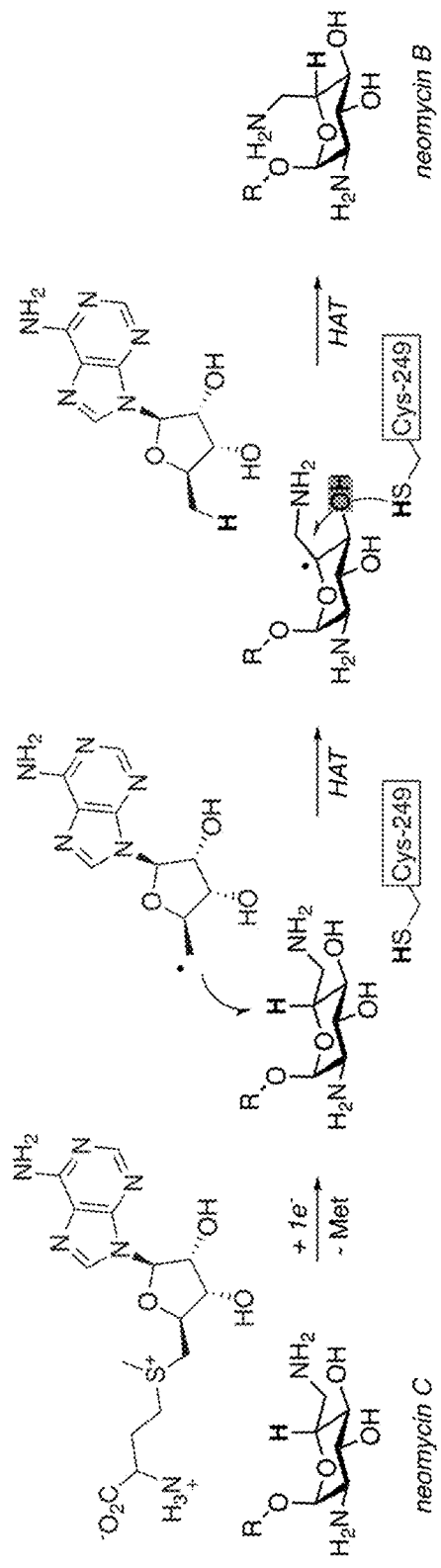
FIG. 1D depicts the enzymatic biosynthesis of Neomycin B.

It was envision that rare sugar isomers could be obtained directly from biomass-derived carbohydrates through site-selective radical epimerization reactions. A kinetically-controlled epimerization process would require C—H bond cleavage and C—H bond formation steps to proceed through distinct mechanisms, but could afford product yields and selectivities exceeding those observed under canonical equilibrium-controlled sugar isomerization conditions. This approach draws is related to reports of enzymatic radical epimerizations mediated by the cofactor S-adenosyl methionine (SAM). For example, in the biosynthesis of Neomycin B from Neomycin C, a high energy 5'-deoxyadenosyl radical (5'dAdo) abstracts the C5 hydrogen atom from the Neomycin C terminal saccharide (FIG. 1D). Subsequent re-delivery of a hydrogen atom to the opposite face is achieved via a pendant cysteine thiol. Within the enzyme active site, diastereoselective hydrogen atom transfer steps are thus promoted through exquisite spatial control over the hydrogen atom donor/acceptor pairs. The architecture of the enzyme further mitigates any chemical incompatibility of 5'dAdo radical and cysteine thiol. Outside the physical context of an enzyme, however, other interactions would be necessary to achieve kinetic control and prevent reagent donor/acceptor quenching. While several notable synthetic hydrogen atom transfer (HAT)-mediated epimerization reactions have been developed, these methods almost universally proceed through reversible HAT steps, affording equilibrium product distributions. However, a remarkable deracemization reaction recently reported by Knowles has established the conceptual viability of contra-thermodynamic radical isomerization through sequential proton-coupled electron transfer (PCET) and HAT steps.

Figure 1E:
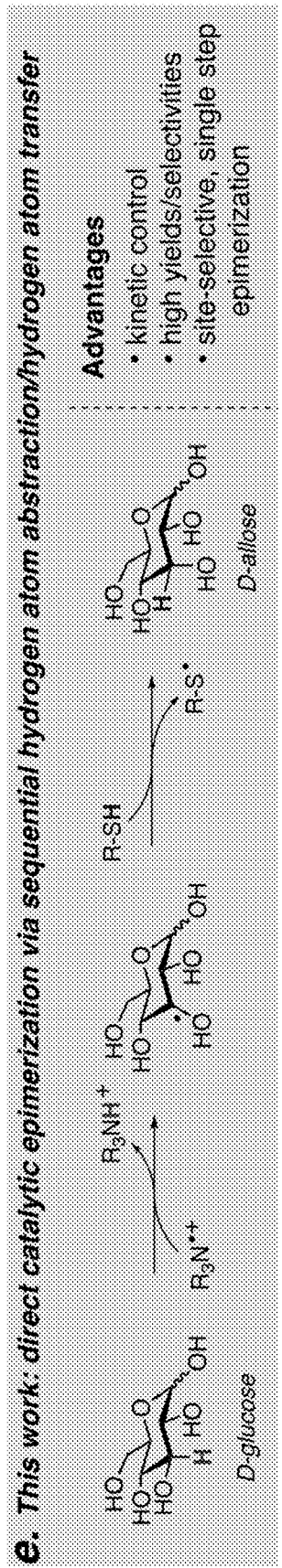
FIG. 1E depicts an exemplary reaction of the present disclosure.

In addition to kinetic challenges posed by employing chemically-incompatible reagents, the success of this transformation further requires distinguishing among numerous nearly identical C—H bonds within the context of a highly-polar, densely-functionalized, stereochemically-complex unprotected carbohydrate substrate. Indeed, while site-selective functionalization of carbohydrate O—H bonds has been the subject of considerable recent attention, examples of selective carbohydrate C—H oxidation and functionalization are extremely limited. Certain precedents by Minnaard, Waymouth, and Muramatsu have established the feasibility of site-selective oxidation of minimally-protected monosaccharides to keto-sugars using $Pd^{II}$/benzoquinone, $Pd^{II}/O_2$, and $Sn^{IV}/Br_2$ catalyst systems, respectively. Recent work by Minnaard and Taylor has further demonstrated that selective carbohydrate C—H alkylation reactions can be promoted via hydrogen atom abstraction by quinuclidinium radical cation generated under photoredox conditions. Disclosed herein is a method for the synthesis of rare sugar isomers from biomass-derived precursors through the site-selective epimerization of unprotected sugars and glycans (FIG. 1E).

In one aspect, the present disclosure provides methods of forming an epimer of a pyranose monosaccharide or a pyranose saccharide residue in an oligosaccharide or a glycoside, represented by the following scheme:

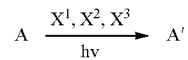

wherein,
A is a pyranose monosaccharide or a pyranose saccharide residue in an oligosaccharide or a glycoside;
A' is an epimer of A, wherein the stereochemical configuration of a chiral center bearing a hydroxyl moiety in A' is inverted relative to the stereochemical configuration of the chiral center in A;
$X^1$ is a photocatalyst;
$X^2$ an amine;
$X^3$ is a hydrogen atom donor; and
hv is light.

In another aspect, the present disclosure provides methods of deoxygenating a pyranose monosaccharide or a pyranose saccharide residue in an oligosaccharide or a glycoside, represented by the following scheme:

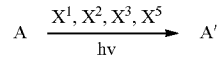

wherein,

A is a pyranose monosaccharide or a pyranose saccharide residue in an oligosaccharide or a glycoside;

A' is a dehydrated isomer of A; wherein A' comprises a —C(O)—CH$_2$— moiety at a location that is —CH(OH)—CH(OH)— in A;

X$^1$ is a photocatalyst;

X$^2$ is a base or absent;

X$^3$ is a hydrogen atom donor;

X$^5$ is a Lewis acid; and hv is light.

In certain embodiments, the pyranose monosaccharide or the pyranose saccharide residue is an allose, an altrose, a galactose, an anhydrogalactose, a glucose, an anhydroglucose, a gulose, a idose, a mannose, a talose, an anhydropyranose, an anhydroglucopyranose, an arabinose, an abequose, a fucose, a lyxose, a mycarose, a quinovose, a rhamnose, a ribose, a paratose, a xylose, a galactosamine, glucosamine, a glucopyranosylamine, a glucosamine, a glucal, a vancosamine, or a deoxyglucose. In certain embodiments, the pyranose monosaccharide or the pyranose saccharide residue is a glucose, an anhydrogalactose, an arabinose, a glucosamine, an anhydroglucose, a galactose, an anhydromannose, a xylose, a fucose, or a deoxyglucose.

In certain embodiments, the pyranose monosaccharide or the pyranose saccharide residue is substituted with alkyl, acyl, ester, amido, alkyloxy, alkyloxyalkyl, aminoalkyl, alkenyl, alkynyl, cycloalkyl, heterocyclyl, heterocyclylalkyl, alkylsilyl, sulfonamide, aryl, heteroaryl, heteroaralkyl, or aralkyl. In certain embodiments, the pyranose monosaccharide or the pyranose saccharide residue is substituted with alkyl, acyl, aralkyl, heterocyclyl, or alkylsilyl. In certain embodiments, the pyranose monosaccharide or the pyranose saccharide residue is substituted with methyl. In certain embodiments, the pyranose monosaccharide or the pyranose saccharide residue is substituted with benzyl. In certain embodiments, the pyranose monosaccharide or the pyranose saccharide residue is substituted with alkylsilyl selected from the group consisting of trimethylsilyl, triisopropylsilyl, tert-butyldimethylsilyl, and tert-butyldiphenylsilyl.

In certain embodiments, A is a pyranose monosaccharide. In certain embodiments, A is a pyranose saccharide residue in an oligosaccharide. In certain embodiments, A is a pyranose saccharide residue in a glycoside (e.g., in an aryl C-glycoside, or a pyranosylnucleobase). In certain embodiments, A is empagliflozin, invokamet, sugammadex, acarbose, amphotericin, carboxymaltose, vancomycin, chloroeremomycin, ivermectin, lomaivitivin, calicheamicin, MK-8591, belomycin, doxorubicin, or neomycin.

In certain embodiments, X$^1$ has a structure represented by formula I

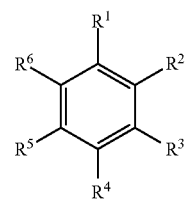

wherein,

R$^1$, R$^2$, R$^3$, R$^4$, R$^5$, and R$^6$ are each independently selected from the group consisting of H, alkyl, halo, hydroxyl, carboxyl, acyl, ester, thioester, alkoxy, amino, amido, cyano, nitro, azido, alkylthio, alkenyl, alkynyl, cycloalkyl, heterocyclylalkyl, heteroaralkyl, sulfonamide, aryl, heteroaryl, heterocyclyl, and aralkyl.

In certain embodiments, R$^1$ is heteroaryl (e.g., carbazolyl) or cyano.

In certain embodiments, R$^2$ is heteroaryl (e.g., carbazolyl) or cyano.

In certain embodiments, R$^3$ is heteroaryl (e.g., carbazolyl) or cyano.

In certain embodiments, R$^4$ is heteroaryl (e.g., carbazolyl) or cyano.

In certain embodiments, R$^5$ is heteroaryl (e.g., carbazolyl) or cyano.

In certain embodiments, R$^6$ is heteroaryl (e.g., carbazolyl) or cyano.

In certain embodiments, X$^1$ is:

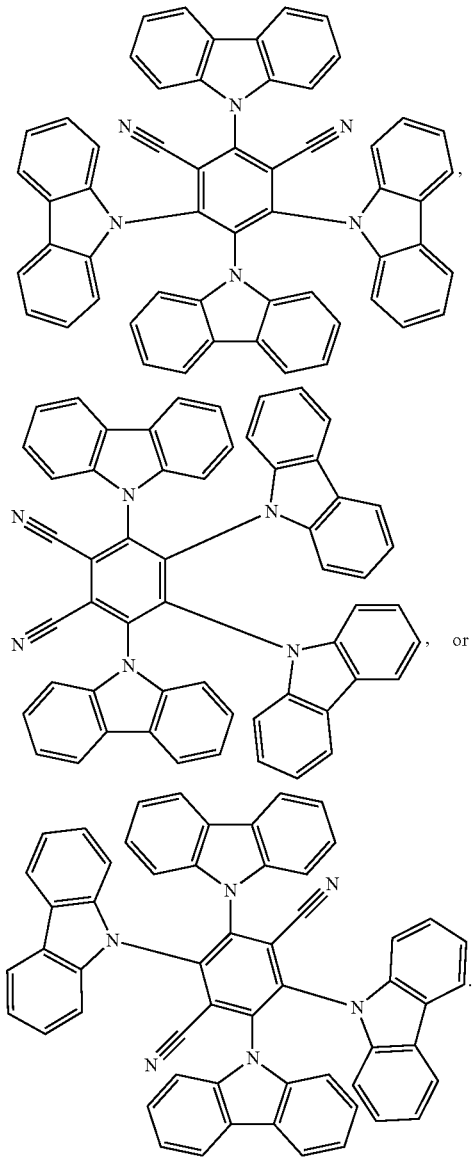

In certain embodiments, wherein X has a structure represented by formula II:

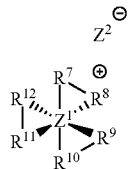

wherein,
each of $R^7$, $R^8$, $R^9$, $R^{10}$, $R^{11}$ and $R^{12}$ is independently aryl or heteroaryl;
$Z^1$ is a transition metal; and
$Z^2$ is a non-coordinating anion.

In certain embodiments, $R^7$ is heteroaryl (e.g., pyridyl).
In certain embodiments, $R^8$ is aryl (e.g., phenyl).
In certain embodiments, $R^9$ is aryl (e.g., phenyl).
In certain embodiments, $R^{10}$ is heteroaryl (e.g., pyridyl).
In certain embodiments, $R^{11}$ is heteroaryl (e.g., pyridyl).
In certain embodiments, $R^{12}$ is heteroaryl (e.g., pyridyl).
In certain embodiments, $R^{10}$ and $R^{11}$ are heteroaryl (e.g., pyridyl).

In certain embodiments, $R^7$, $R^8$, $R^9$, $R^{10}$, $R^{11}$ or $R^{12}$ is substituted with alkyl, heteroalkyl, halo, hydroxyl, carboxyl, acyl, ester, thioester, alkoxy, amino, amido, cyano, nitro, azido, alkylthio, alkenyl, alkynyl, cycloalkyl, heterocyclylalkyl, heteroaralkyl, sulfonamide, aryl, heteroaryl, heterocyclyl, or aralkyl. In certain embodiments, $R^7$, $R^1$, $R^9$, $R^{10}$, $R^{11}$ or $R^{12}$ is substituted with alkyl (e.g., tert-butyl), heteroalkyl (e.g., trifluoromethyl), or halo (e.g., fluoro). In certain embodiments, $R^{10}$ and $R^{11}$ are substituted with alkyl (e.g., methyl, tert-butyl), heteroaryl (e.g., trifluoromethyl), alkoxy (e.g., methoxy). In certain embodiments, $R^{10}$ and $R^{11}$ substituted with the same substituent at the 4 position or the 5 position.

In certain embodiments, the transition metal is a platinum group metal (i.e., ruthenium, rhodium, palladium, osmium, iridium, or platinum; preferably iridium).

In certain embodiments, the non-coordinating anion is a phosphate (e.g., hexafluorophosphate).

In certain embodiments, $X^1$ is

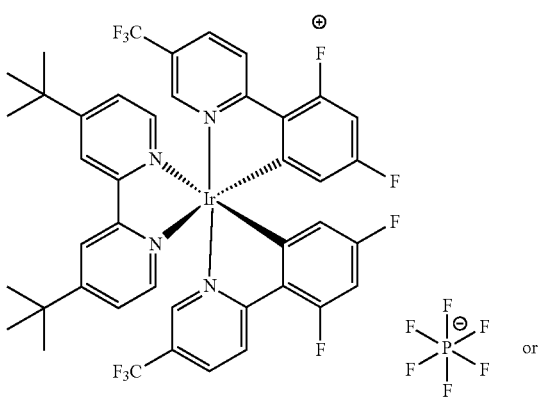

or

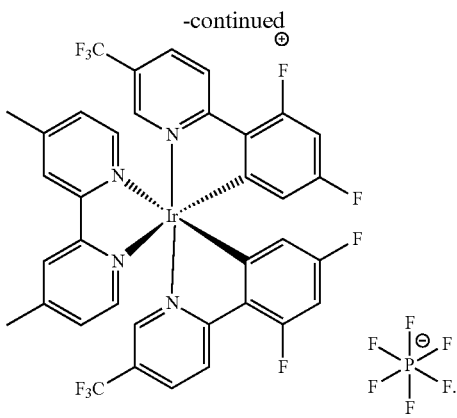

In certain embodiments, $X^1$ is a tungstate (e.g., a decatungstate polyanion). In certain embodiments, $X^1$ is an alkali metal tungstate. In certain embodiments, $X^1$ is sodium tungstate. In certain embodiments, $X^1$ is an alkylammonioum tungstate. In certain embodiments, $X^1$ is selected from tetra-n-butylammonium phosphate tungstate, tetra-n-butylammonium benzoate tungstate (e.g., tetra-n-butylammonium chlorobenzoate tungstate, tetra-n-butylammonium fluorobenzoate tungstate, tetra-n-butylammonium bromobenzoate tungstate, tetra-n-butylammonium iodobenzoate tungstate, tetra-n-butylammonium trifluoromethylbenzoate tungstate, tetra-n-butylammonium methoxybenzoate tungstate, tetra-n-butylammonium cyanobenzoate tungstate, tetra-n-butylammonium nitrobenzoate tungstate), tetra-n-butylammonium bromide tungstate, tetra-n-butylammonium chloride tungstate, tetra-n-butylammonium sulfate tungstate, tetra-n-butylammonium perchlorate tungstate, tetra-n-butylammonium nitrate tungstate, tetra-n-butylammonium tosylate tungstate, tributylmethylammonium dibutyl phosphate tungstate. In certain embodiments, $X^1$ is tetra-n-methylammonium decatungstate (TMADT), tetra-n-propylammonium decatungstate (TPADT), or tetra-n-butylammonium decatungstate (TBDAT).

In certain embodiments, $X^2$ is an alkyl amine or a heterocyclic amine. In certain embodiments, $X^2$ is an alkyl amine. In certain embodiments, $X^2$ is an quaternary alkyl amine. In certain embodiments, $X^2$ is a heterocyclic amine. In certain embodiments, $X^2$ is a heteroaryl amine or a heterocyclyl amine. In certain embodiments, $X^2$ is substituted with alkyl, heteroalkyl, halo, hydroxyl, carboxyl, acyl, ester, thioester, alkoxy, amino, amido, cyano, nitro, azido, alkylthio, alkenyl, alkynyl, cycloalkyl, heterocyclylalkyl, heteroaralkyl, sulfonamide, aryl, heteroaryl, heterocyclyl, or aralkyl. In certain embodiments, $X^2$ is substituted with heteroaralkyl (e.g., quinolinalkyl, methoxyquinolinalkyl), hydroxyl, or amido (e.g., phenylamido or chlorophenylamido). In certain embodiments, $X^2$ is quinuclidine, quinidine, cinchonidine, cinchonine, quinuclidinol, or 3-chloro-N-(3-quinuclidinyl) benzamide.

In certain embodiments, $X^3$ is a thiol or a disulfide (e.g., ditert-butyldisulfide). In certain embodiments, $X^3$ is an alkyl thiol, an acyloxyalkylthiol, an aralkyl thiol, a heterocyclic thiol, or an aryl thiol. In certain embodiments, $X^3$ is a heterocyclic thiol (e.g., a heterocyclyl thiol or heteroaryl thiol). In certain embodiments, $X^3$ is a heteroaryl thiol (e.g., furanthiol). In certain embodiments, $X^3$ is an cycloalkyl thiol (e.g., cyclohexylthiol or adamantylthiol). In certain embodiments, $X^3$ is an alkyl thiol (e.g., hexanethiol, dodecanethiol, or tert-butylthiol). In certain embodiments, $X^3$ is an alkyl thiol (e.g., ethanethiol, octanethiol, or decanethiol). In certain embodiments, X³ is esteralkyl thiol (e.g., ethylmercaptoacetate), acyloxyalkyl thiol (e.g., mercaptoethyl propionate), sulfonatealkyl thiol (e.g., sodium mercaptopropanesulfonate), carbamatealkyl thiol (e.g., tert-butyl mercaptoethylcarbamate), silylalkyl thiol (e.g., trimethoxysilylpropylthiol), hydroxyalkyl thiol (e.g., hydroxyethylthiol), or (cycloalkyl)alkylthiol (e.g., p-mentha-8-thiol-3-one or 2-,3-,10-mercaptopinane). In certain embodiments, X³ is an alkyl dithiol (e.g., hexyldithiol). In certain embodiments, X³ is an aralkyl thiol (e.g., homobenzylthiol). In certain embodiments, X³ is an aryl thiol (e.g., methylphenylthiol, tert-butylphenylthiol, methoxyphenylthiol, dimethoxyphenylthiol, biphenylthiol, fluorophenylthiol, chlorophenylthiol, dichlorophenylthiol, pentachlorophenylthiol, bromophenylthiol, trifluoromethylphenylthiol, trifluoromethoxyphenylthiol, nitrophenylthiol, aminophenylthiol, or phneyldithiol). In certain embodiments, X³ is an amino acid (e.g., cysteine or homocysteine). In certain embodiments, X³ is N-acetylcysteine methyl ester, N-acetylcysteine, cysteine, or homocysteine. In certain embodiments, X³ is a silanethiol (e.g., triisopropylsilanethiol or triphenylsilanethiol). In certain embodiments, X³ is a carbothioic acid (e.g., triisopropylsilanethiolortriphenylsilanethiol).

In certain embodiments, the method further comprises a base. In certain embodiments, the base is a metal acetate, an ammonium acetate, a phosphate, or a carbonate. In certain embodiments, the base is a metal acetate (e.g., sodium acetate, potassium acetate, or cesium acetate). In certain embodiments, the base is an ammonium acetate (e.g., tetrabutylammonium acetate). In certain embodiments, the base is an inorganic base. In certain embodiments, the base is an organic base. In certain embodiments, the base is a heteroaromatic base (e.g., pyridine, cyanopyridine, diethyl pyridinedicarboxylate, di-tert-butylbipyridine, or phenylimidazole). In certain embodiments, the base is a heteroaryl carbonate. In certain embodiments, the base is a carboxylate base (e.g., a benzoate). In certain embodiments, the base has a structure represented by formula III:

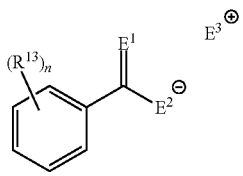

wherein,
E¹ and E² are each independently selected from the group consisting of O and S;
E³ is an alkali metal cation, an alkaline earth metal cation, or a quaternary alkylammonium cation;
R¹³ is independently for each occurrence alkyl, heteroalkyl, halo, hydroxyl, carboxyl, acyl, ester, thioester, alkoxy, amino, amido, cyano, nitro, azido, alkylthio, alkenyl, alkynyl, cycloalkyl, heterocyclylalkyl, heteroaralkyl, sulfonamide, aryl, heteroaryl, heterocyclyl, or aralkyl; and
n is 0-5.

In certain embodiments, E¹ is O.
In certain embodiments, E² is O.
In certain embodiments, E³ is an alkali metal cation (e.g., sodium or potassium).

In certain embodiments, E³ is a quaternary alkylammonium cation (e.g., tetrabutylammonium).
In certain embodiments, R¹³ is halo (e.g., chloro). In certain embodiments, R¹³ is fluoro, chloro, bromo, or iodo.
In certain embodiments, n is 1.
In certain embodiments, the base is

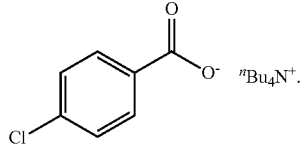

In certain embodiments, the base is immobilized on a resin. In certain embodiments, the resin comprises a plurality of poly(styrene-co-divinylbenzene) microspheres (e.g., Amberlite). In certain embodiments, the resin comprises a poly(styrene-co-divinylbenzene) microsphere functionalized with an alkylammonium salt (e.g., a tetra-alkylammionoum chloride, such as IRA-900). In certain embodiments, the base is selected from the group consisting of tetra-n-butylammonium phosphate, tetra-n-butylammonium benzoate (e.g., tetra-n-butylammonium chlorobenzoate, tetra-n-butylammoniumfluorobenzoate, tetra-n-butylammoniumbromobenzoate, tetra-n-butylammoniumiodobenzoate, tetra-n-butylammoniumtrifluoromethylbenzoate, tetra-n-butylammonium methoxybenzoate, tetra-n-butylammonium cyanobenzoate, tetra-n-butylammonium nitrobenzoate), tetra-n-butylammonium bromide, tetra-n-butylammonium chloride, tetra-n-butylammonium sulfate, tetra-n-butylammonium perchlorate, tetra-n-butylammonium nitrate, tetra-n-butylammonium tosylate, tributylmethylammonium dibutyl phosphate, 1,8-Diazabicyclo(5.4.0)undec-7-ene, 1,4-diazabicyclo[2.2.2]octane, and dimethylaminopyridine. In certain embodiments, the base is selected from the group consisting of tetra-n-butylammonium phosphate, tetra-n-butylammonium benzoate (e.g., tetra-n-butylammonium chlorobenzoate, tetra-n-butylammonium fluorobenzoate, tetra-n-butylammoniumbromobenzoate, tetra-n-butylammoniumiodobenzoate, tetra-n-butylammonium trifluoromethylbenzoate, tetra-n-butylammonium methoxybenzoate, tetra-n-butylammonium cyanobenzoate, tetra-n-butylammonium nitrobenzoate), tetra-n-butylammonium bromide, tetra-n-butylammonium chloride, tetra-n-butylammonium sulfate, tetra-n-butylammonium perchlorate, tetra-n-butylammonium nitrate, tetra-n-butylammonium tosylate, tributylmethylammonium dibutyl phosphate, silica, aluminum oxide, 1,8-Diazabicyclo(5.4.0)undec-7-ene, 1,4-diazabicyclo[2.2.2]octane, and dimethylaminopyridine; or a combination thereof.

In certain embodiments, the method further comprises a Lewis acid. In certain embodiments, the Lewis acid is a transition metal. In certain embodiments, the transitional metal is group VII transition metal. In certain embodiments, the transitional metal is manganese. In certain embodiments, is an alkyl borate. In certain embodiments, the alkyl borate is bis(pinacolato)diboron or Tri-tert-butyl borate.

In certain embodiments, hv is blue light (i.e., light with a wavelength of about 427 nm to about 500 nm). In certain embodiments, hv is white light (e.g., light from a compact fluorescent lamp).

In certain embodiments, the method further comprises a further a solvent or a solvent mixture. In certain embodiments, the solvent is a protic polar solvent, an aprotic polar solvent, or a nonpolar solvent; and the solvent mixture comprises at least two solvents selected independently from a protic polar solvent, an aprotic polar solvent, and a nonpolar solvent. In certain embodiments, the solvent is DMSO, acetonitrile, methanol, water, tetrahydrofuran, dichloromethane, toluene, or dioxane; and the solvent mixture is methanol and water, or acetonitrile and water.

In certain embodiments, the method is performed at ambient conditions (e.g., room temperature and pressure). In certain embodiments, the method is performed at 40° C.-100° C. In certain embodiments, the method is performed at about 40° C., about 50° C., about 60° C., about 70° C., or about 80° C. In certain embodiments, the method is performed at about 50° C., or about 70° C.

In certain embodiments, the method is performed for about 0.5-6 hours. In certain embodiments, the method is performed for about 1 hour or about 2 hours.

In certain embodiments, the sugar is a pyranose and the epimer is formed at the C2, C3, or C4 position; or a combination thereof. In certain embodiments, the sugar is a pyranose and the epimer is formed at the C2 position. In certain embodiments, the sugar is a pyranose and the epimer is formed at the C3 position. In certain embodiments, the sugar is a pyranose and the epimer is formed at the C4 position.

In certain embodiments, the sugar is a pyranose and the sugar is deoxygenated at the C2, C3, or C4 position. In certain embodiments, the sugar is a pyranose and the sugar is deoxygenated at the C2 position. In certain embodiments, the sugar is a pyranose and the sugar is deoxygenated at the C3 position. In certain embodiments, the sugar is a pyranose and the sugar is deoxygenated at the C4 position.

In certain embodiments, the yield of A' is greater than 25%, greater than 30%, greater than 40%, greater than 50%, greater than 60%, greater than 70%, greater than 80%, greater than 90%, greater than 95%, or greater than 99%.

In certain embodiments, the solvent is a deuterated solvent. In certain embodiments, the method replaces a hydrogen at the site of epimerization (e.g., the C2, C3, or C4) position with a deuterium. In certain embodiments, the method replaces a hydrogen at the C2 position with a deuterium. In certain embodiments, the method replaces a hydrogen at the C3 position with a deuterium. In certain embodiments, the method replaces a hydrogen at the C4 position with a deuterium.

In certain embodiments, the method is performed in batch. In certain embodiments, the method is performed continuously (e.g., in a flow reactor).

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, Mass. (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, Calif. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—$CH_2$—O-alkyl, —OP(O)(O-alkyl)$_2$ or —$CH_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

As used herein, the term "alkyl" refers to saturated aliphatic groups, including but not limited to $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x-C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amide", as used herein, refers to a group

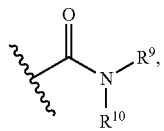

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

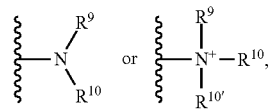

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably, the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

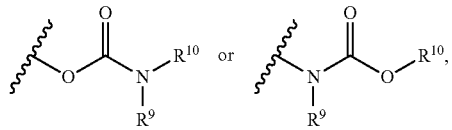

wherein $R^9$ and $R^{10}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group —OCO$_2$—.

The term "carboxy", as used herein, refers to a group represented by the formula —CO$_2$H.

The term "ester", as used herein, refers to a group —C(O)OR$^9$ wherein R$^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —OSO$_3$H, or a pharmaceutically acceptable salt thereof.

The term "sulfonamide" is art-recognized and refers to the group represented by the general formulae

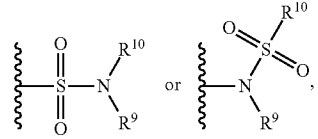

wherein R$^9$ and R$^{10}$ independently represents hydrogen or hydrocarbyl.

The term "sulfoxide" is art-recognized and refers to the group-S(O)—.

The term "sulfonate" is art-recognized and refers to the group SO$_3$H, or a pharmaceutically acceptable salt thereof.

The term "sulfone" is art-recognized and refers to the group —S(O)$_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)SR$^9$ or —SC(O)R$^9$ wherein R$^9$ represents a hydrocarbyl.

The term "thioether", as used herein, is equivalent to an ether, wherein the oxygen is replaced with a sulfur.

The term "urea" is art-recognized and may be represented by the general formula

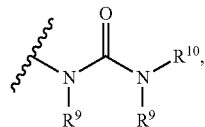

wherein R$^9$ and R$^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

EXAMPLES

The invention now being generally described, it will be more readily understood by reference to the following examples which are included merely for purposes of illustration of certain aspects and embodiments of the present invention, and are not intended to limit the invention.

Example 1: Exemplary Epimerization Methods of the Disclosure

Discussion

After extensive exploration of reaction conditions, the minimally-protected model substrate, α-methylglucose, was found to react cleanly under photochemical conditions to afford α-methylallose as the sole reaction product in 92% yield within 3. Optimal reaction conditions employ catalytic quantities of 1,2,3,5-tetrakis(carbazol-9-yl)-4,6-dicyanobenzene (4-CzIPN), quinuclidine, adamantane thiol, and tetrabutylammonium p-chlorobenozate in MeCN/DMSO at room temperature under blue light irradiation. No epimerization was observed to occur in the absence of photocatalyst, thiol, or light, and only trace product (<1%) was observed in the absence of quinuclidine. Reaction yield was considerably diminished in the absence of benzoate base (29% yield), or by employing tetrabutylammonium benzoate as the base (63% yield). Ir[(dFCF$_3$ppy)(dtbpy)]PF$_6$ (IrF) is also an effective photoredox catalyst for this transformation, promoting the desired reaction at only 1 mol % loading. However, the observation of oxidation products, as well as considerable cost differences (4CzIPN, $5/mmol; IrF, $1000/mmol) led us to select 4CzIPN as the preferred reagent. Alkyl thiols were uniquely effective at promoting epimerization: no reaction was observed using thiophenols or thiobenzoic/thioacetic acid derivatives, nor using any other hydrogen atom donor surveyed.

Scheme 1. Epimerization of α-methylglucose to α-methylallose. Effect of changes to optimized reaction conditions. Yields determined by proton nuclear magnetic resonance ($^1$H NMR) analysis using 4-fluoroanisole as internal standard. RSM, recovered starting material; MeCN, acetonitrile; DMSO, dimethylsulfoxide; RT, room temperature; LED, light emitting diode; Me, methyl; DABCO, 1,4-diazabicyclo[2,2,2]octane.

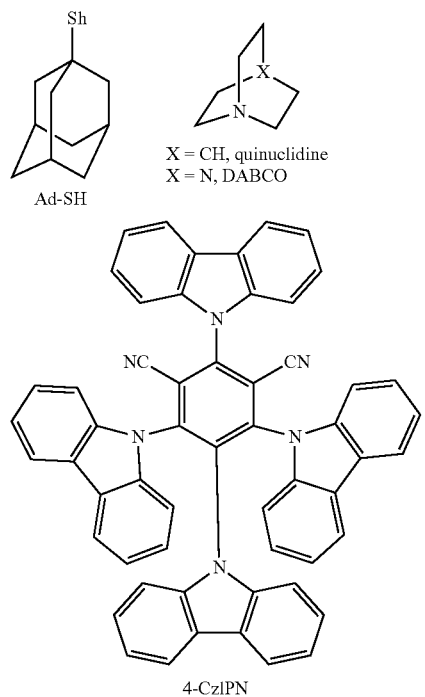

| Entry | variation from "standard conditions" | % yield (% RSM) |
|---|---|---|
| 1 | no photocatalyst | 0% (99%) |
| 2 | no quinuclidine | <1% (99%) |
| 3 | no thiol | 0% (98%) |
| 4 | no hv | 0% (99%) |
| 5 | no 4-ClOBzBu$_4$N | 29% (71%) |
| 6 | Bu$_4$NOBz instead of 4-ClOBzBu$_4$N | 63% (35%) |
| 7 | 1% Ir[dF(CF$_3$)ppy]$_2$(dttbpy)PF$_6$ instead of 4-CzIPN | 88% (2%) |
| 8 | DABCO instead of quinuclidine | 0% (99%) |
| 9 | hydrogen atom source (see SI) | 0% (99%) |

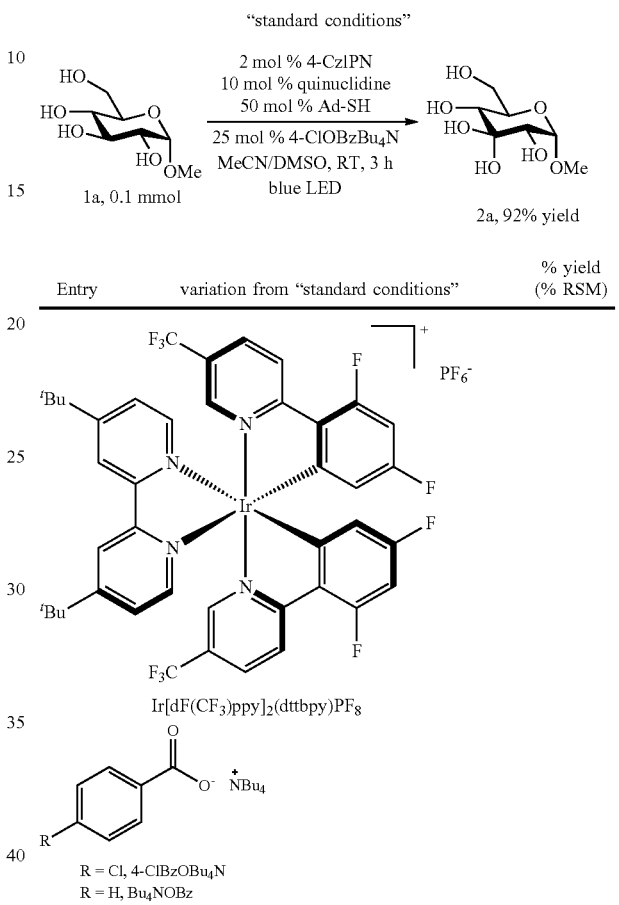

C3-selectivity observed here is congruent with the substrate-controlled selectivity previously noted by both Waymouth and Minnaard in oxidation reactions. Measurements of the $^1J_{(C-H)}$ coupling constants in the absence and presence of quinuclidine suggest that site-selectivity correlates with C—H bond dissociation free enthalpy (BDFE). No epimerization product was detected in reactions employing permethylated or peracetylated substrates. Permethylated glucose exhibited considerably larger $^1J_{(C-H)}$ couplings at all positions (indicating strengthened C—H bonds), and no interaction between quinuclidine and substrate was detected in this case.

Figure 2:
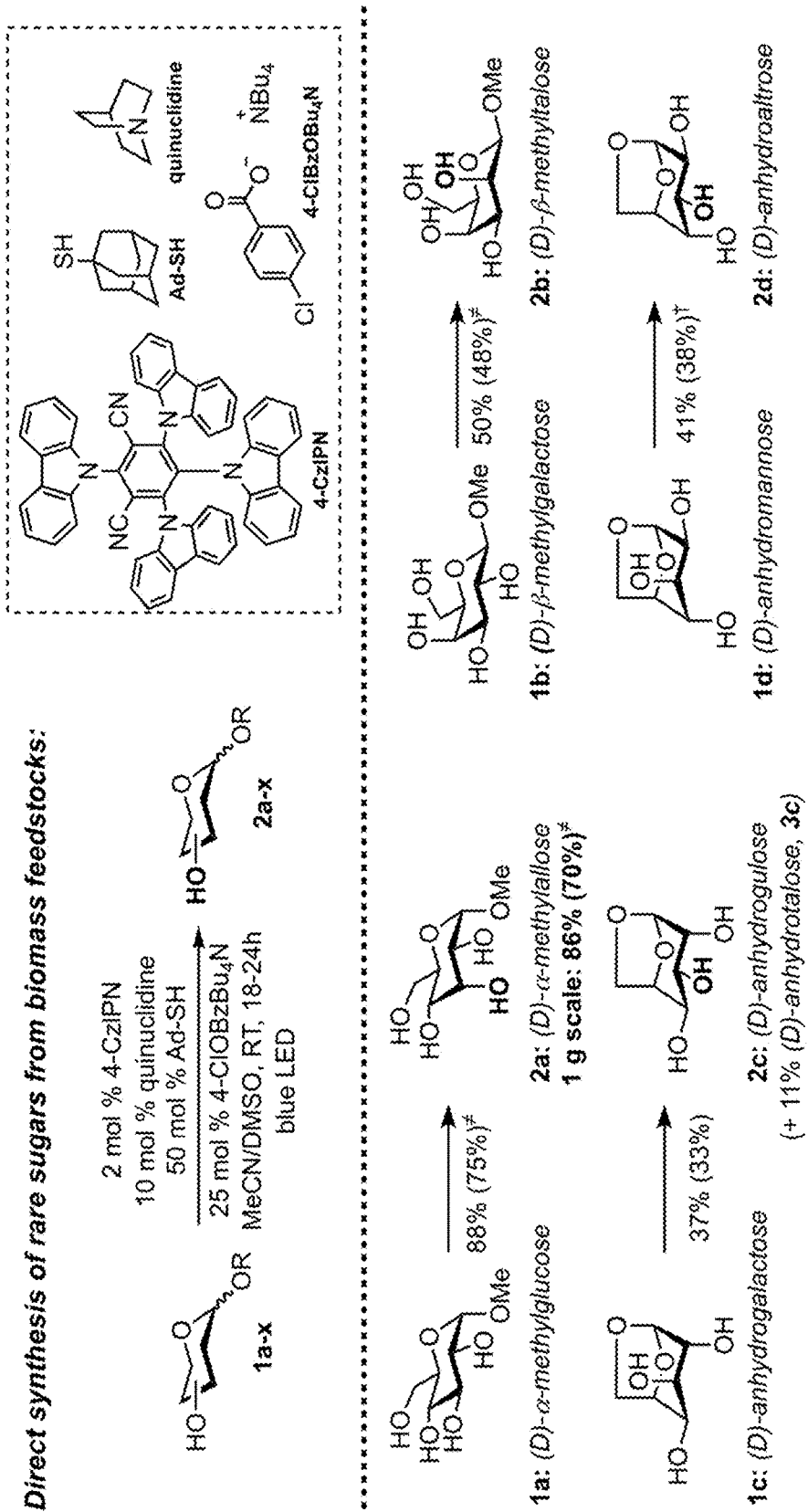
FIG. 2 depicts the exemplary scope of the reaction with respect to substrate. Reactions were conducted on a 0.3 mmol scale in duplicate; the average $^1$H NMR yield is reported; duplicate reactions were combined, then isolated; isolated yields are in parentheses. ˇ, Isolated in peracetylated form ‡, 1 mol % Ir[dF(CF3)ppy]$_2$(dtbpy)PF$_6$ used instead of 4CzIPN. †, Reaction was conducted using 5 mol % quinuclidine. *, Reaction was conducted using 2.5 mol % quinuclidine.
Figure 2:
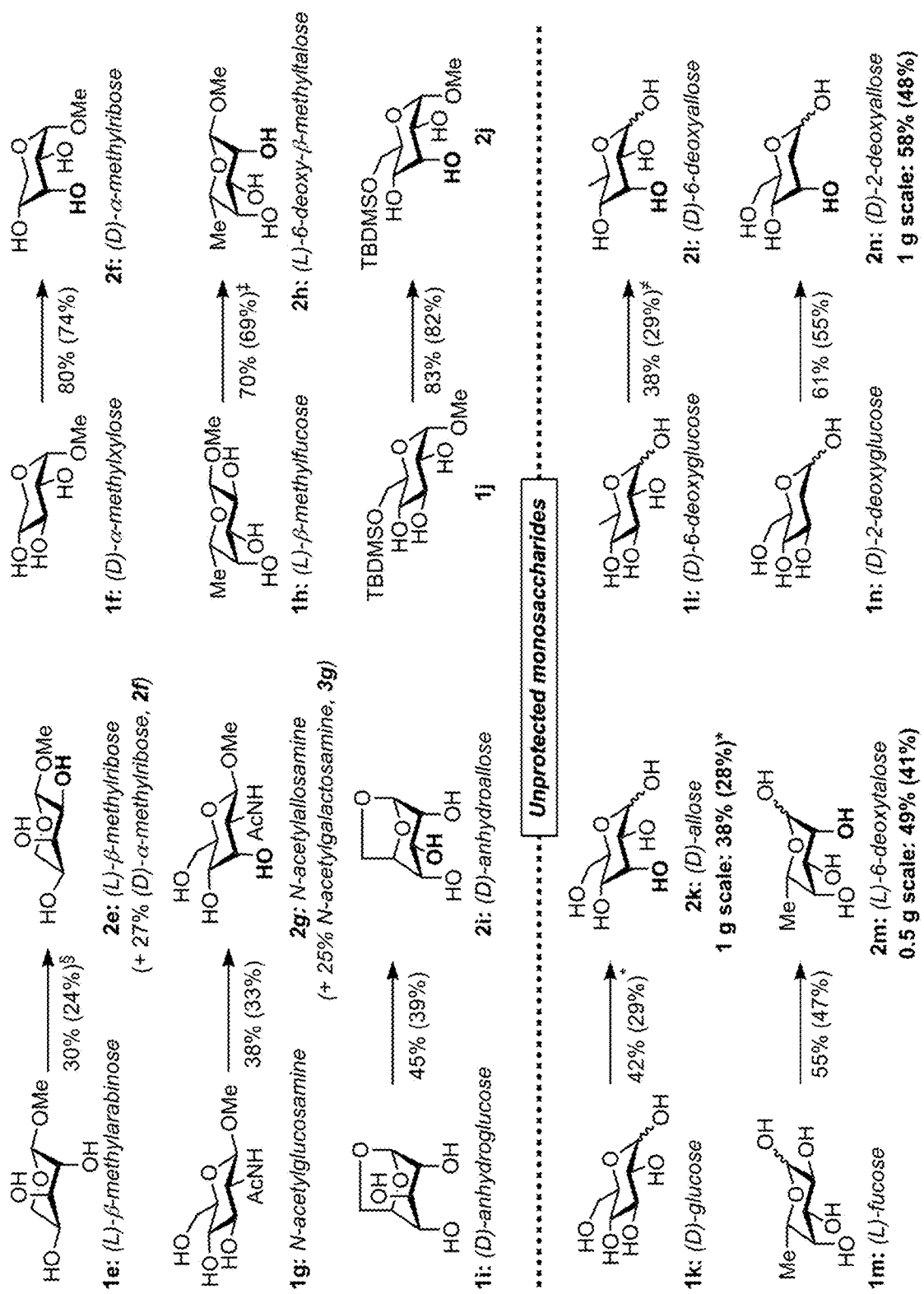
Figure 2:
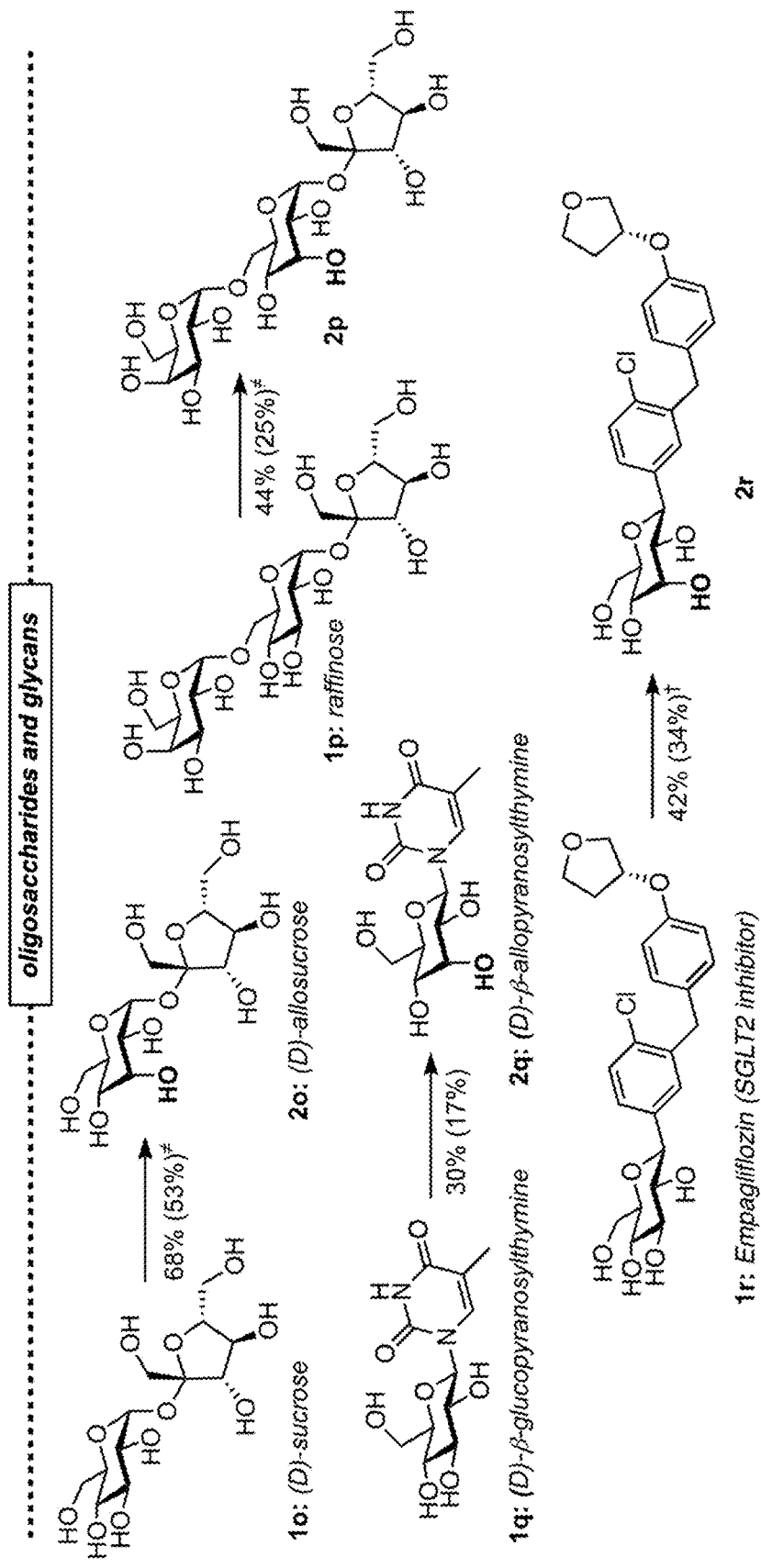

A range of biomass-derived and abundant monosaccharides were evaluated as substrates under the optimized reaction conditions (FIG. 2). This strategy provides synthetic access to 4 of the 5 rare hexose isomers. In addition to (D)-allose products obtained from glucose-configured substrates, (D)-talose (2b), (D)-gulose (2c), and (D)-altrose (2d) products are obtained selectively from the reaction of β-methylgalactose, anhydrogalactose, and anhydromannose, respectively. The biomass-derived pentose sugars (D)-α-methylxylose (1f) and (L)-β-methylarabinose (1e) afforded (D)- and (L)-ribose derivatives through C3- and C2-selective epimerization, respectively. While (D)-ribose is accessible on large scale through glucose fermentation, synthetic access to (L)-ribose remains extremely limited. Despite the presence of an electron rich acetamide substituent, N-acetylglucosamine derivative 1g also undergoes productive epimerization, reacting to afford a 1.5:1 mixture of the C3- and C4-epimeric products, N-acetylallosamine, 2g, and N-acetylgalactosamine, 3g, respectively.

Completely unprotected monosaccharides also undergo selective epimerization under these conditions: for example, 42% yield (D)-allose 2k is obtained from (D)-glucose (c.f. 2.5% total yield over 4 steps, using enzymatic methods), and 55% yield (L)-6-deoxytalose 2m is obtained from the reaction of (L)-fucose. The reaction of (D)-2-deoxyglucose affords (D)-2-deoxyallose in 61% yield: importantly, epimerization of 2-deoxygenated sugars cannot be realized using alternative, enolization-based isomerization methods.

More complex glycans were subsequently evaluated to further assess the selectivity and functional group compatibility of the reaction conditions. Allosucrose, 2o, can be obtained selectively from sucrose in 68% yield, and despite the presence of 14 stereogenic centers, the reaction of raffinose, 1p, affords a singly-epimerized product, 2p, in 44% yield. Pyrimidine-containing pyranonucleoside, 1q, reacted to afford the $C_3$-epimeric product, 2q. Finally, the C-glycoside SGLT2 inhibitor Empagliflozin was also examined as a substrate, and was found to afford the C3 epimeric product, 2r, in 42% yield with no observation of epimerization at any other position in the molecule.

Figure 3A:
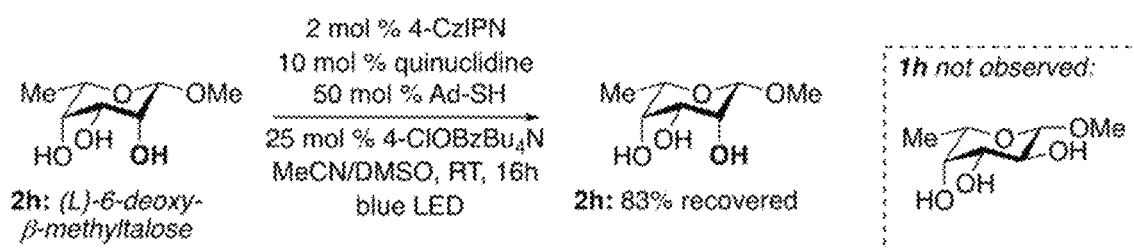
FIG. 3A shows that no epimerization is observed when reaction products are resubjected to the standard reaction conditions.
Figure 3B:
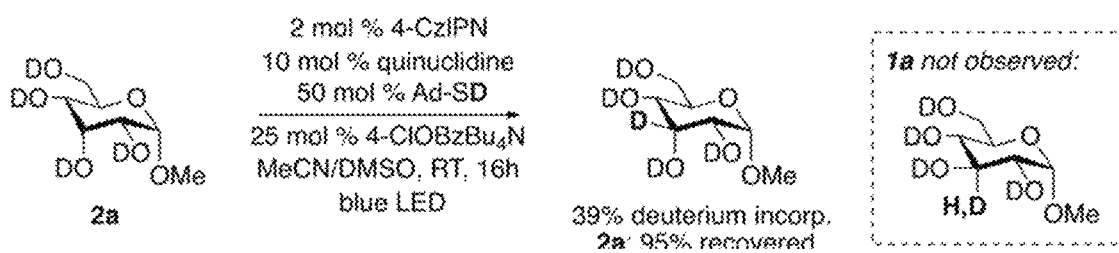
FIG. 3B shows that deuterium labeling studies indicate that reaction product reacts under standard reaction conditions, but both epimers converge to a common product.
Figure 4A:
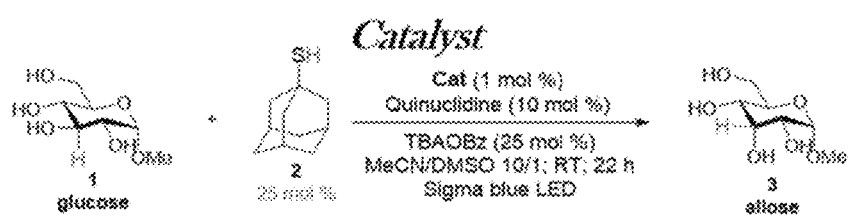
FIG. 4A depicts exemplary reactions performed with different catalysts.
Figure 4A:
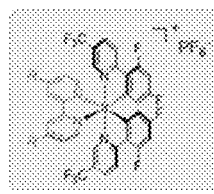
Figure 4A:
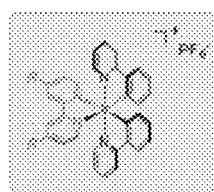
Figure 4B:
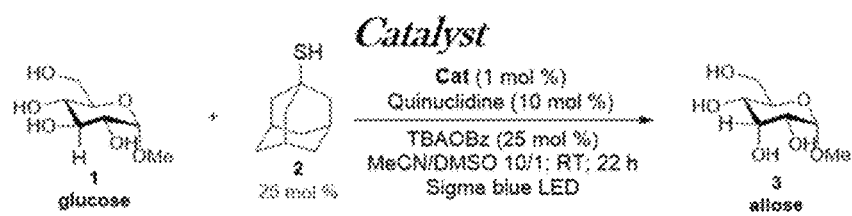
FIG. 4B depicts exemplary reactions performed with different catalysts.
Figure 4B:
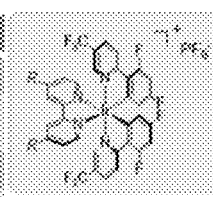
Figure 4B:
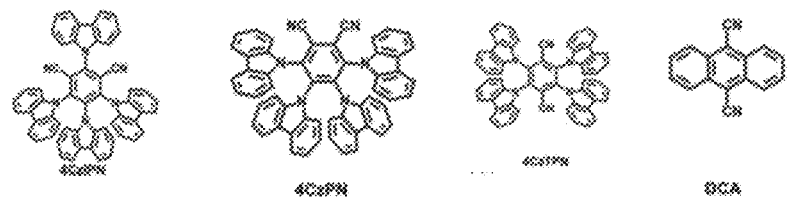
Figure 4C:
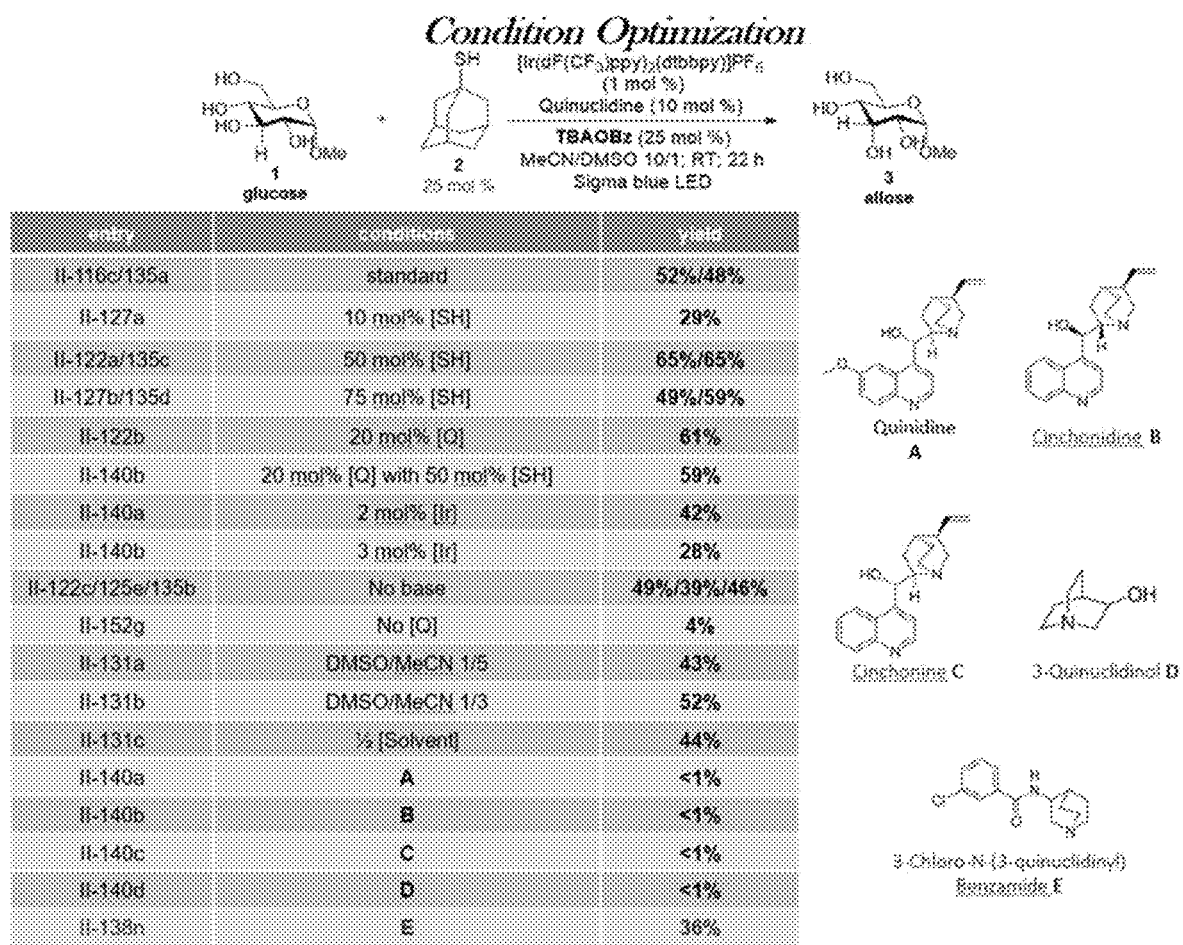
FIG. 4C depicts exemplary reactions performed with different conditions.
Figure 4F:
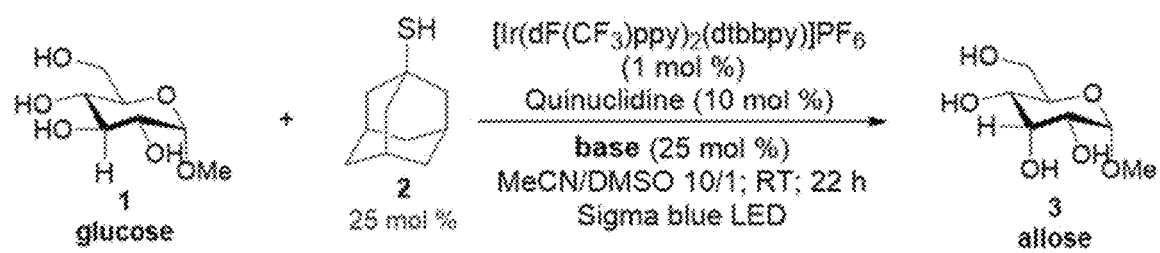
FIG. 4F depicts exemplary reactions performed with different bases.
Figure 4F:
Figure 4F:
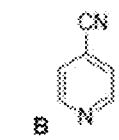
Figure 4F:
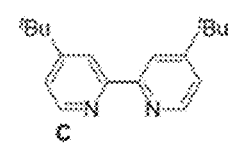
Figure 4F:
Figure 5A:
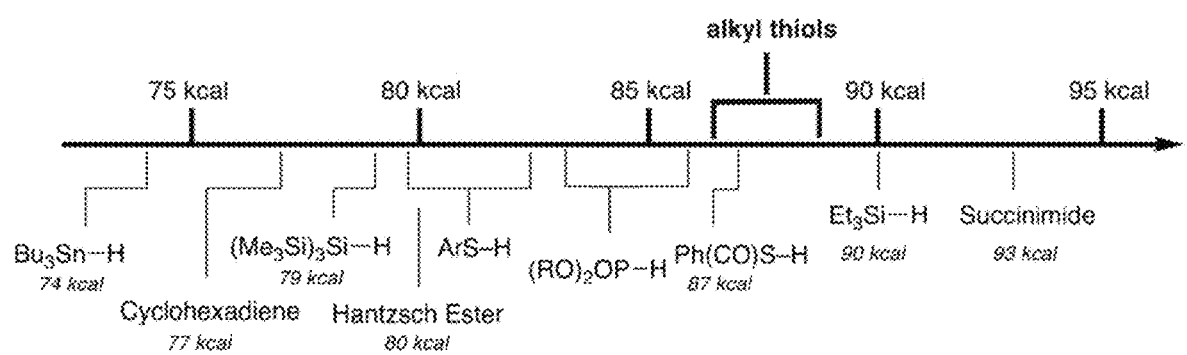
FIG. 5A depicts the bond energy of certain hydrogen atom donors.
Figure 5B:
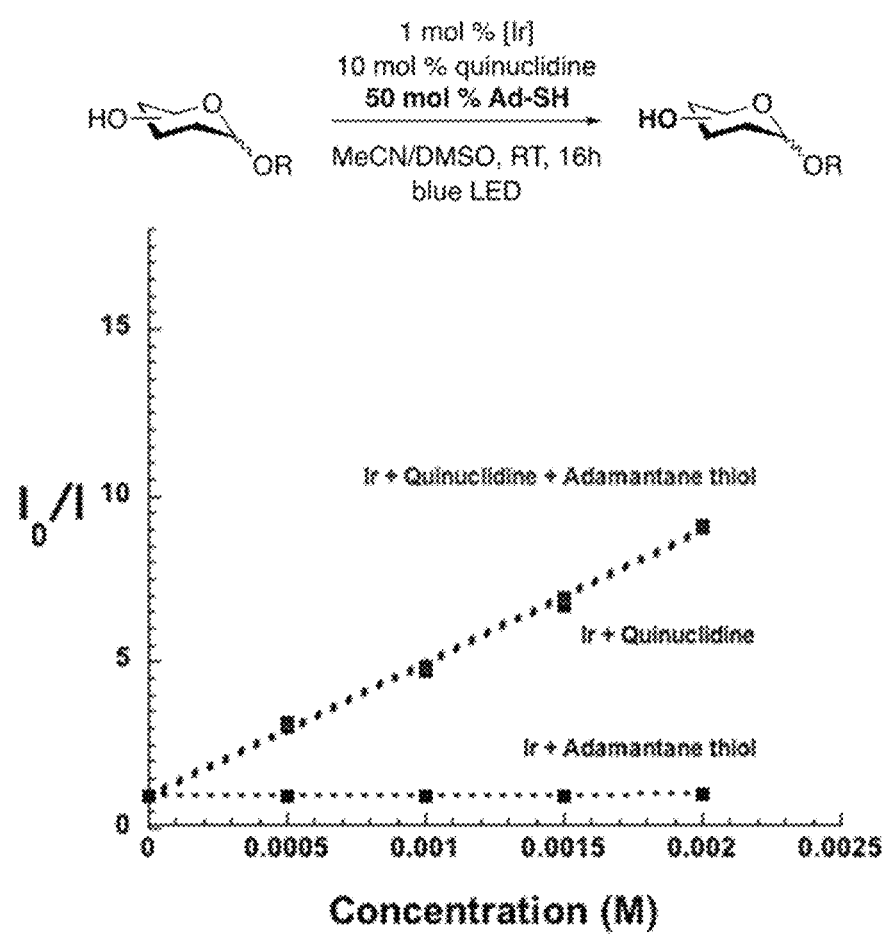
FIG. 5B shows a Stern-Volmer plot for an exemplary reaction of the disclosure.
Figure 5C:
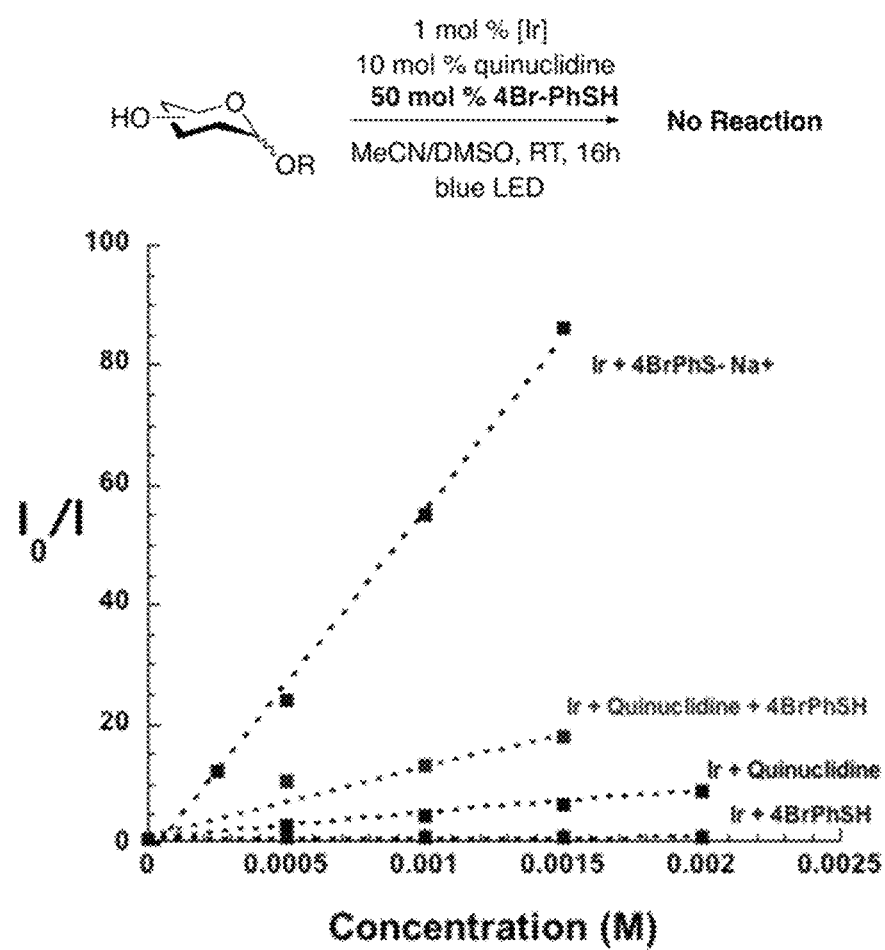
FIG. 5C shows a Stern-Volmer plot for an exemplary reaction of the disclosure.
Figure 6:
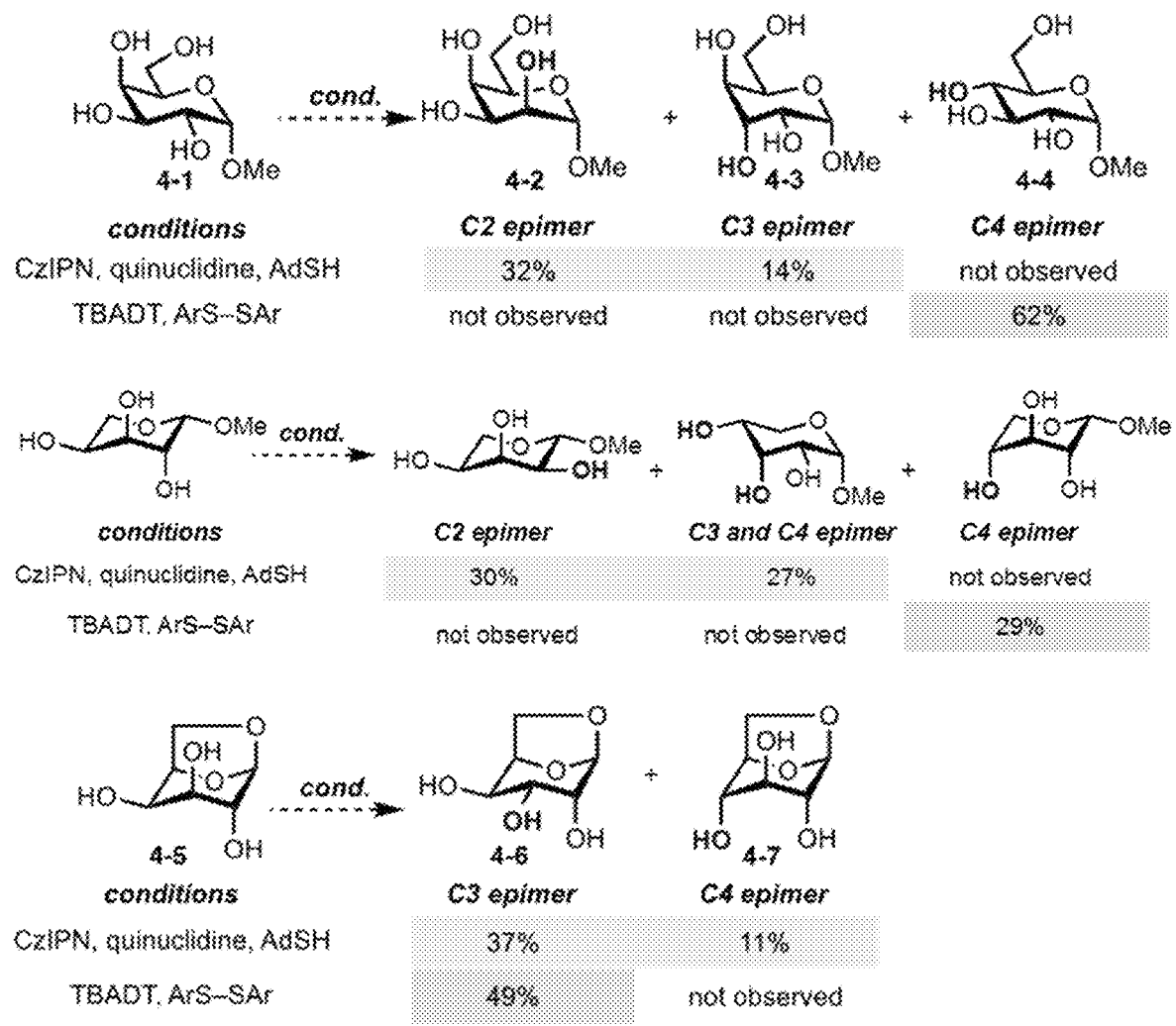
FIG. 6 depicts the effect of reaction conditions on the regioselectivity of the epimerization.
Figure 6:
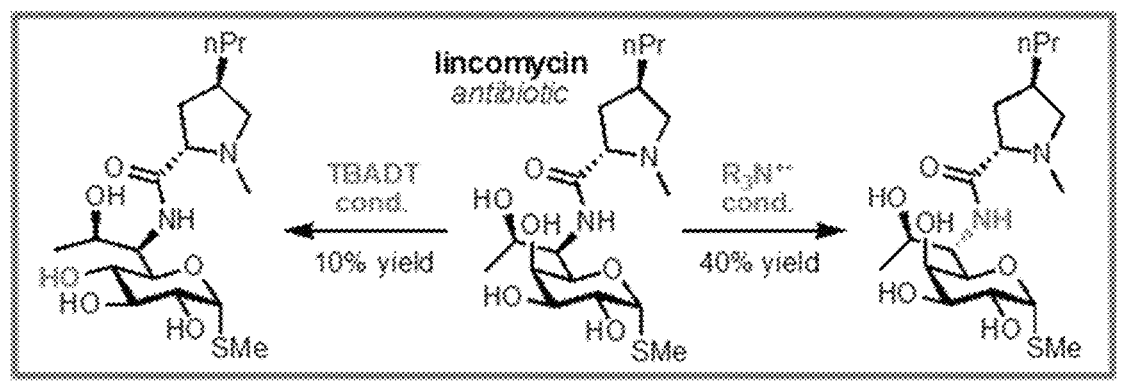
Figure 6:
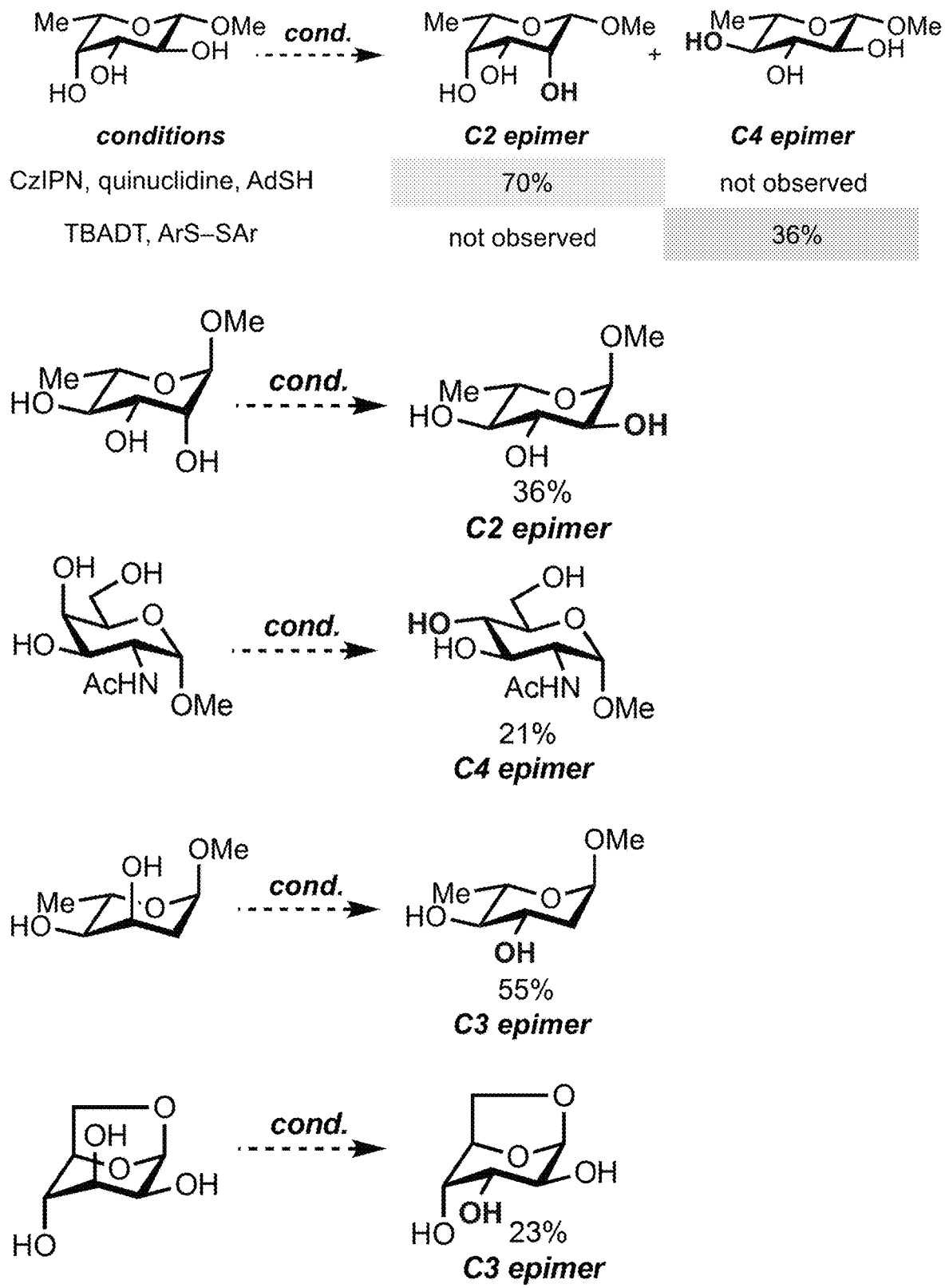
Figure 7A:
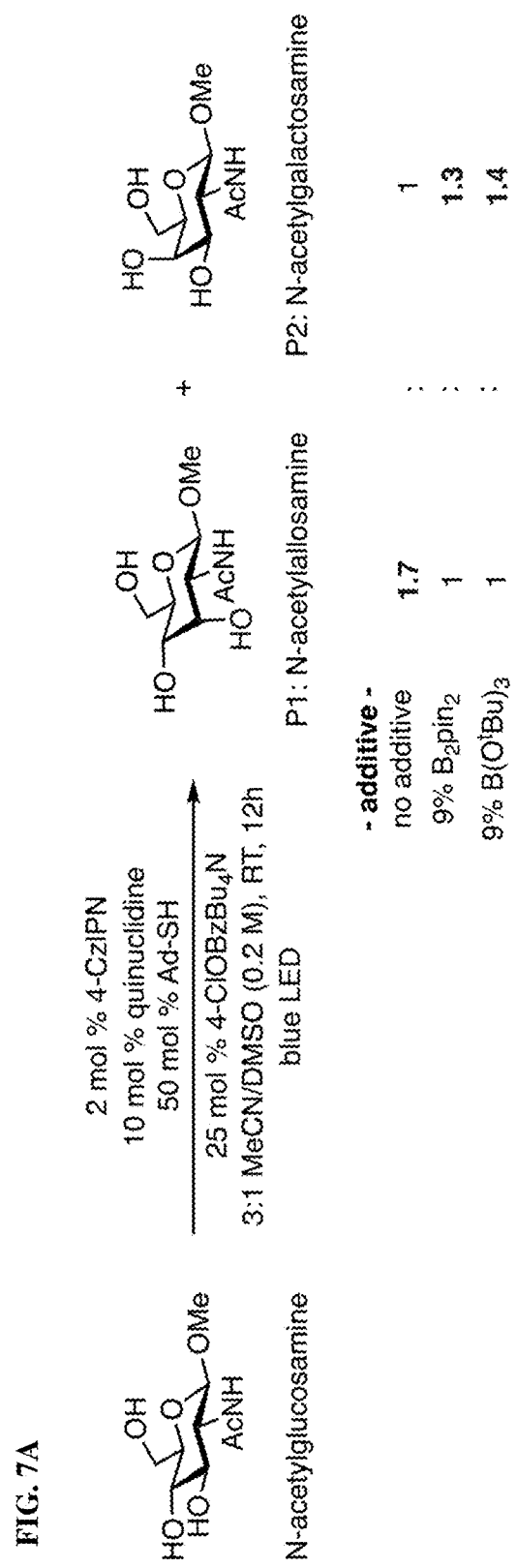
FIG. 7A depicts the effect of the addition of a Lewis acid to the reaction mixture.
Figure 7B:
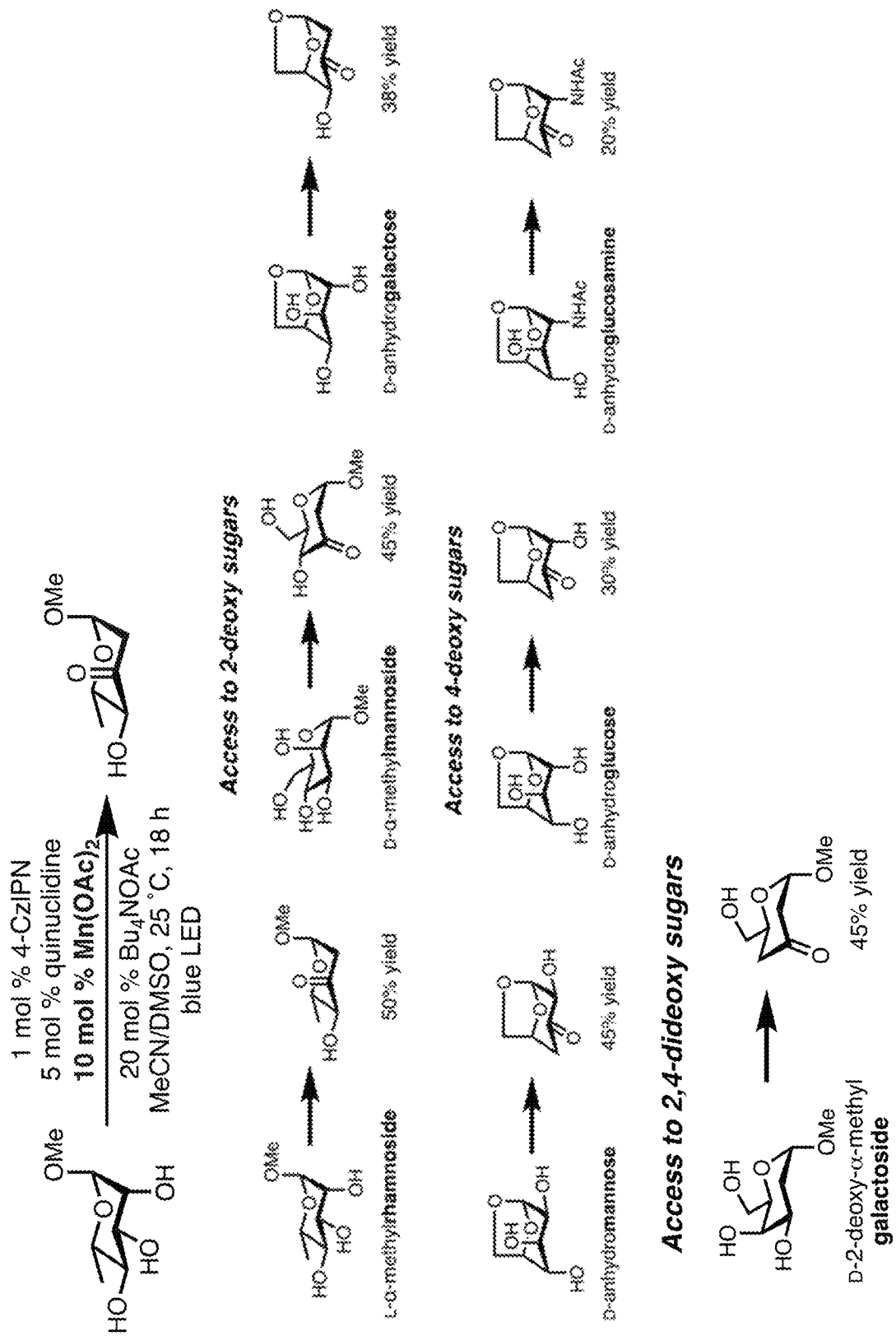
FIG. 7B depicts the effect of the addition of a Lewis acid to the reaction mixture.
Figure 7C:
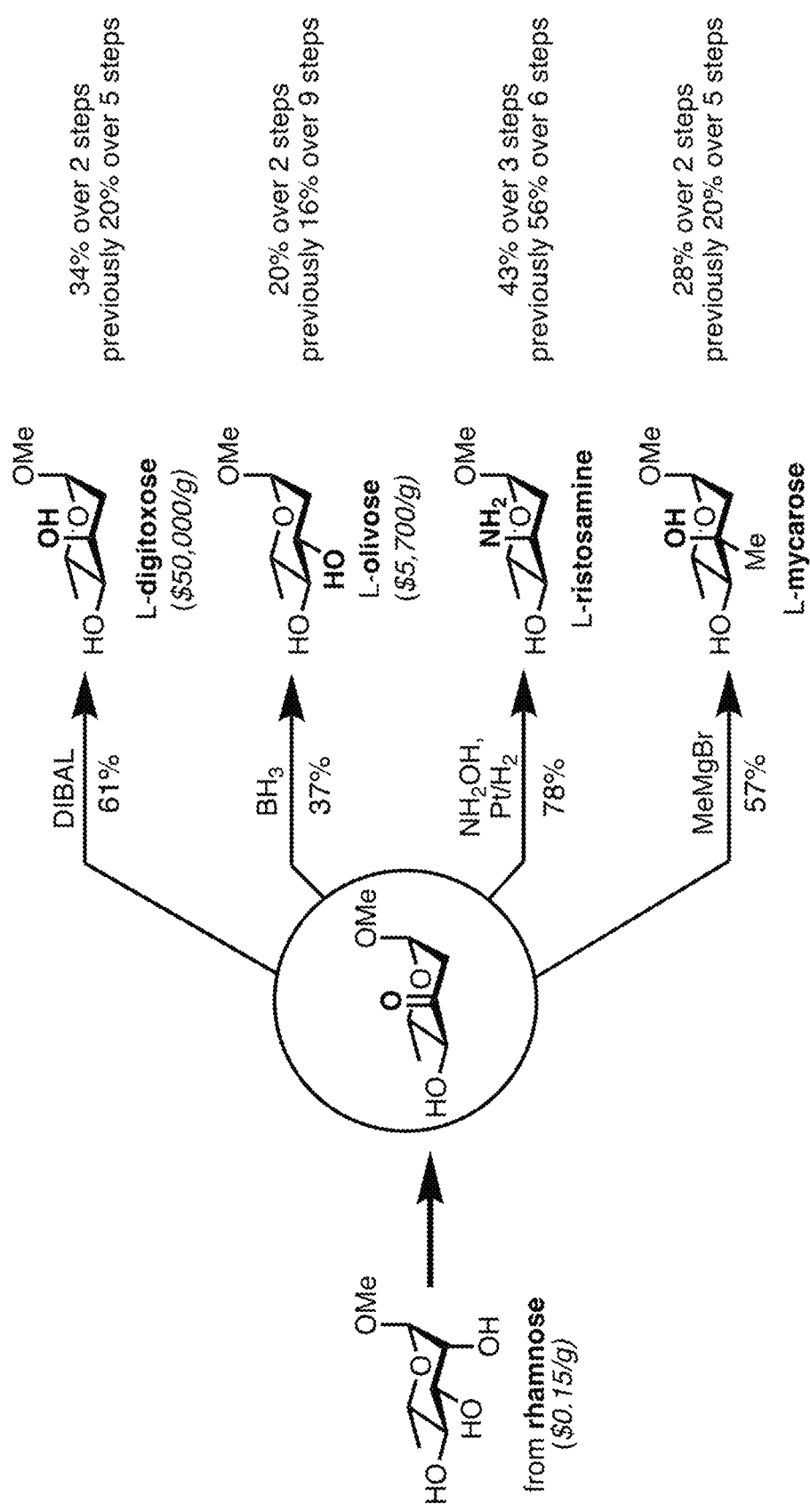
FIG. 7C shows intermediates that can be accessed via the deoxygenation pathway depicted in FIG. 7B.
Figure 8A:
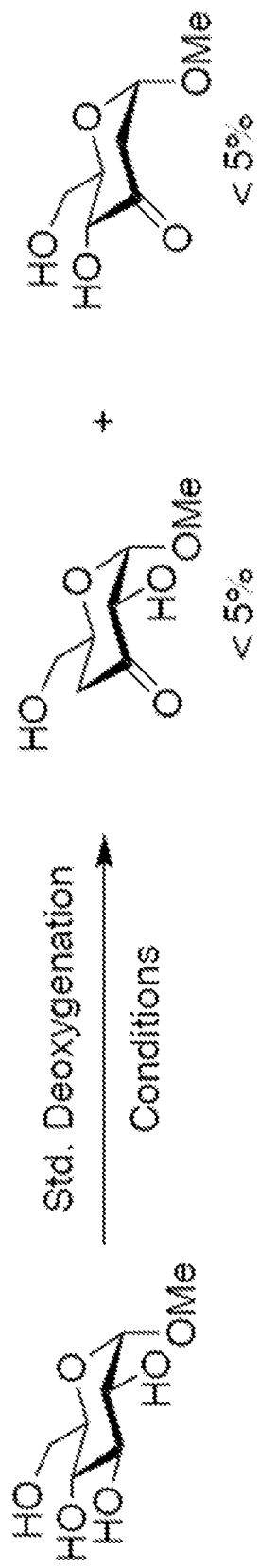
FIG. 8A exemplifies the scope of the deoxygenation reaction disclosed herein. Decreased reactivity is observed when there are no axially-disposed hydroxyl substituents next to the site of radical formation.
Figure 8B:
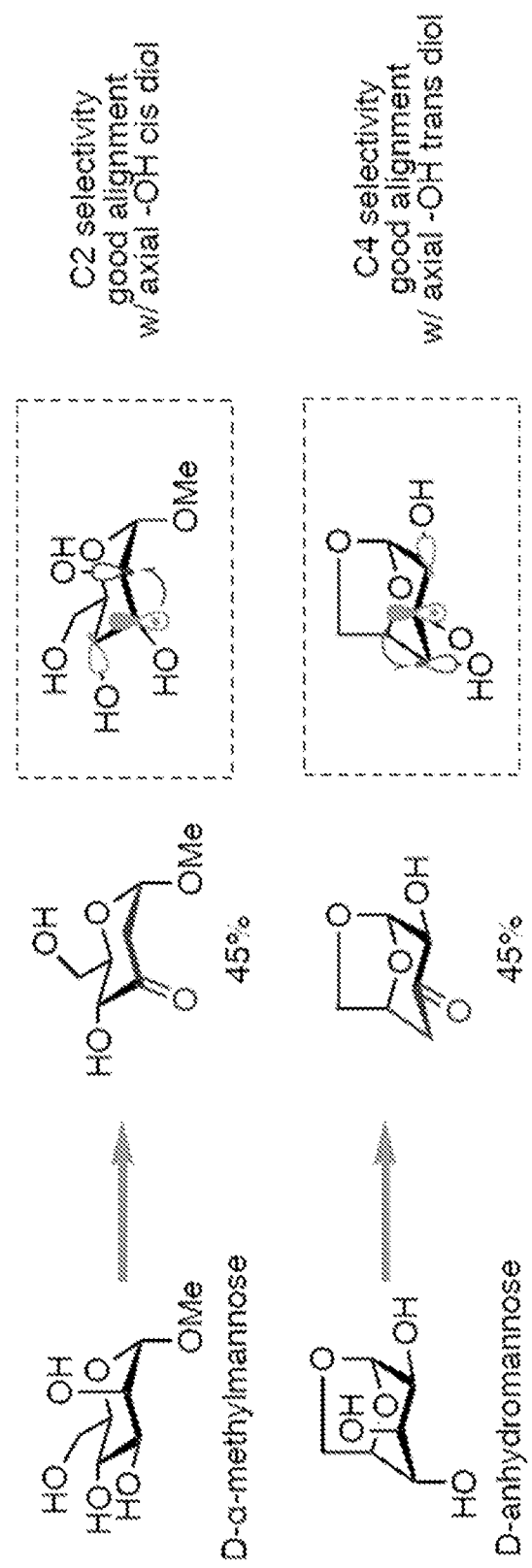
FIG. 8B depicts a predictive model for the regioselectivity of the migration and dehydration steps of the reaction. Hydrogen atom abstraction is sometimes favored at the most hydridic C—H bond (e.g., in the quinuclidine system) or at the least sterically hindered position (e.g., in the decatungstate system).
Figure 8C:
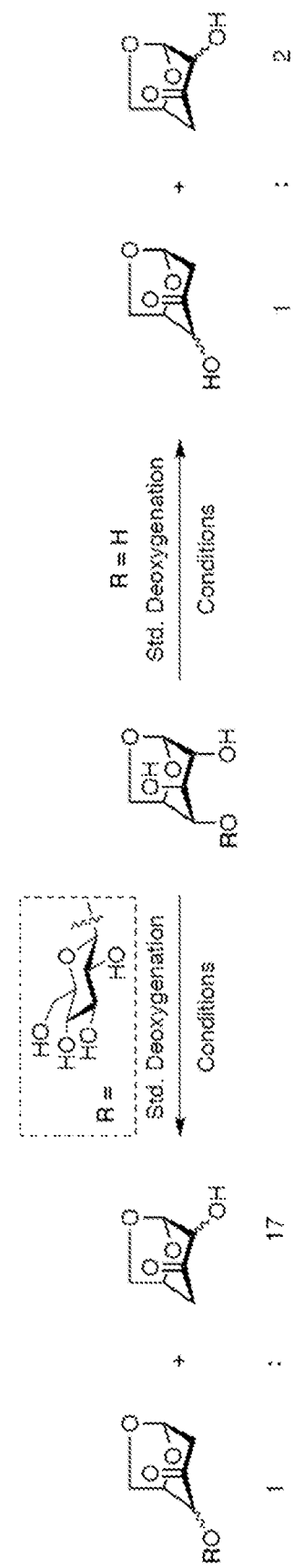
FIG. 8C depicts the effect of leaving group ability on the selectivity of the migration and dehydration steps of the deoxygenation reaction.

A series of experiments were undertaken in order to gather insight into the underlying mechanism of this transformation. Resubjecting 6-deoxy-β-methyltalose, 2h, (formed in 70% yield from β-methylfucose, 1h) to standard reaction conditions did not result in the formation of any β-methylfucose starting material (FIG. 4a). A similar experiment was conducted using α-methylallose and adamantane thiol-d1. After 16 h, 95% α-methylallose was recovered with 39% deuterium incorporation at the C3-position; no glucose products were detected. This experiment demonstrates that both α-methylglucose and α-methylallose can undergo hydrogen atom abstraction but that both converge to the α-methylallose product (FIG. 3B). Taken in conjunction with established thermochemical data, these experiments provide preliminary evidence that these transformations do not proceed under simple equilibrium control.

Figure 3C:
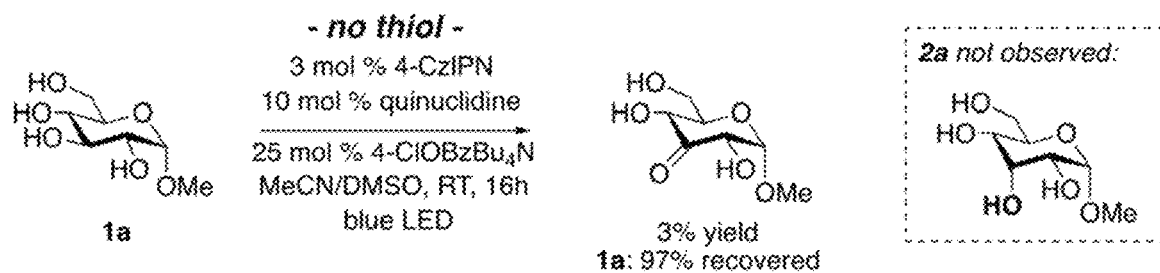
FIG. 3C shows that a reaction in the absence of thiol donor affords no isomerization product, implicating irreversible hydrogen atom abstraction by quinuclinium radical cation.
Figure 3D:
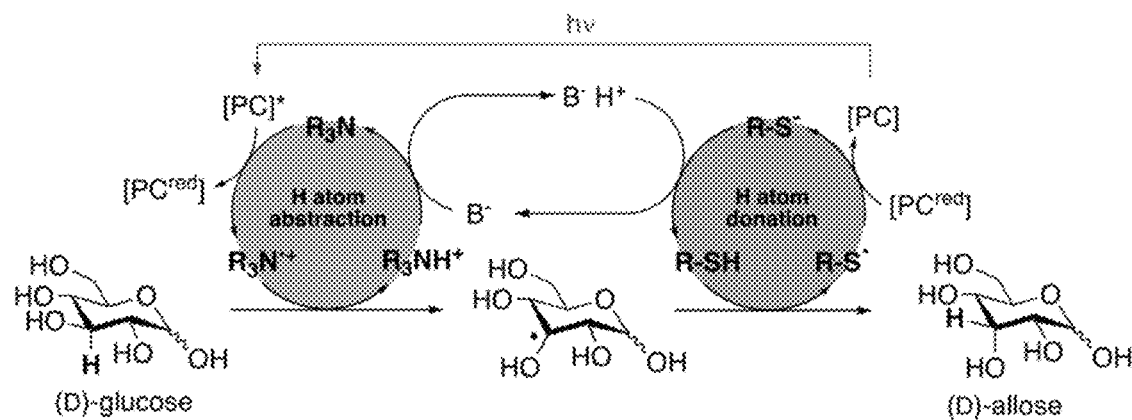
FIG. 3D depicts an exemplary mechanistic pathway for selective isomerization reactions.

To explore the individual elementary steps of this reaction, Stern-Volmer fluorescence quenching was examined under two different sets of conditions. Preliminary experiments reveal that quinuclidine efficiently quenches the photocatalyst excited state, while adamantane thiol does not quench under the conditions examined. In the presence of both quinuclidine and adamantane thiol, quenching kinetics are identical to the "quinuclidine only" conditions. These findings support a mechanism in which the excited photocatalyst is quenched by quinuclidine to generate quinuclidinium radical cation.[28] When catalyst loading is increased to 3 mol % and reaction is run the absence of thiol, small quantities (3% yield) of 3-keto sugar are obtained (FIG. 3C). Importantly, no epimerization is observed under these conditions, nor under any conditions tested where alkyl thiol is not present in the reaction mixture. These experiments establish that photocatalyst and quinuclidine are sufficient for C—H cleavage to occur but insufficient for epimerization. Together, they support a mechanism in which quinuclidinium radical cation mediates an irreversible H-atom abstraction step.

To probe the role of the thiol co-catalyst, an analogous set of fluorescence quenching experiments was carried out using 4-bromothiophenol in place of adamantyl thiol. Under these reaction conditions, no epimerization or consumption of α-methylglucose is observed. As with adamantane thiol, minimal fluorescence quenching was observed using 4-bromothiophenol alone. However, in the presence of both 4-bromothiophenol and quinuclidine, a significant increase in fluorescence quenching was observed relative to the case with quinuclidine alone. It was postulated that this enhanced fluorescence quenching might be due to the oxidation of thiolate—generated in situ by deprotonation of thiol by quinuclidine, or through PCET from a quinuclidine/thiol hydrogen-bonded complex—to the corresponding thiyl radical. Indeed, sodium thiophenolate was also found to quench the photocatalyst at a 10-fold higher rate than quinuclidine alone, and NMR titration studies performed under comparable conditions identified a small equilibrium interaction ($K_{eq}$=42 $M^{-1}$) between 4-bromothiophenol ($pK_a$=9.0 in DMSO) and quinuclidine (quinuclidinium conjugate acid, $pK_a$=9.8 in DMSO), supporting the formation of thiolate in solution.

These experiments indicate that thiol acidity is an important parameter distinguishing productive versus unproductive reaction conditions. In the presence of quinuclidine, acidic thiols can be deprotonated to form thiolate salts. Preferential thiolate quenching of the photocatalyst results in the formation of thiyl radicals. No epimerization was observed under these, or all other photo-oxidative, photo-reductive, and thermal conditions that were explored for the in situ generation of thiyl radical. These findings suggest that thiyl radical is not competent for hydrogen-atom abstraction. Accordingly, the thiol co-catalyst is implicated in a subsequent, irreversible H-atom transfer to the incipient sugar radical.

Collectively, the mechanistic studies presented here support a non-equilibrium epimerization mechanism proceeding through two sequential and distinct hydrogen atom transfer steps: hydrogen atom abstraction by quinuclidinium radical cation (BDE=100 kcal/mol) from substrate, followed by hydrogen atom transfer from thiol (87 kcal/mol) to the incipient sugar radical (FIG. 4D). Though both substrate and product can undergo H-atom abstraction by quinuclidinium radical cation, mechanistic data are consistent with irreversible hydrogen atom abstraction followed by diastereoselective hydrogen atom transfer by thiol. Attendant to a kinetically-controlled epimerization mechanism, the reaction yields and product selectivities presented here exceed nearly all other direct isomerization yields reported to date, which have exclusively reflected thermodynamic product distributions. Ongoing efforts in our laboratory aim are directed towards understanding the molecular basis for site-selectivity, as well as expanding the synthetic scope of this and related transformations.

General Experimental Methods

Unless otherwise noted, all catalytic experiments were performed under nitrogen atmosphere by preparing the reactions in nitrogen-filled purge box. Air and/or moisture-sensitive liquids were transferred with stainless steel cannula or glass Hamilton gas-tight syringes fitted with stainless-steel needles. Reactions were examined by thin-layer chromatography (TLC) on Silica Gel 60 F254 plates (EMD), visualized under UV light (254 nm) and/or p-anisaldehyde and CAM stain, which developed upon heating. Organic solutions were concentrated under reduced pressure on a Büchi rotary evaporator. Flash chromatography was performed using SiliaFlash P60 (230-400 mesh, SiliCycle) and SiliaFlash R60 (20-45 μm, 60 Å, SiliCycle). Ion-exchange chromatography was performed using self-prepared $Ca^{2+}$ form of Dowex 50WX8 (200-400 mesh), which was derived from the commercial available hydrogen form.

Materials and Reagents

All commercially available reagents were purchased from Sigma-Aldrich, Alfa Aesar, Strem, Oakwood, Matrix Scientific, TCI, Carbosynth, or Chem-Impex and used without purification, unless otherwise indicated. Extraction and chromatography solvents were reagent grade and used without purification. Reaction solvents, including acetonitrile and dimethyl sulfoxide, were freshly degassed (freeze-pump-thaw) from commercially anhydrous sources, transferred, and stored in the purge box. Deuterated solvents-namely $CDCl_3$, $CD_2Cl_2$, $d_6$-DMSO, $D_2O$ and $CD_3OD$ (Cambridge Isotope Laboratories) were used without purification.

Instrumentation

Proton nuclear magnetic resonance (H NMR) spectra and proton-decoupled carbon nuclear magnetic resonance ($^{13}C$ NMR) spectra were recorded on a Bruker 400 (400 MHz), 500 (500 MHz), and 600 (600 MHz) spectrometers at 25° C. All chemical shifts (δ) are reported in parts per million (ppm) downfield from tetramethylsilane and are referenced to the residual solvent signal of the NMR solvent. Data are represented as follows: chemical shift, multiplicity (br=broad, s=singlet, d=doublet, t=triplet, q=quartet, quint=quintet, sext=sextet, sept=septet, m=multiplet), coupling constants (J) in Hertz (Hz), integration. Optical rotations were measured using a 1 dm path length cell with a Jasco Model 1010 digital polarimeter at 589 nm. Infrared (IR) spectra were recorded on an Agilent Cary 630 FTIR Spectrometer. Data are represented as follows: frequency of absorption ($cm^{-1}$), intensity of absorption (s=strong, m=medium, w=weak, br=broad). High-resolution mass spectrometry was performed on a JEOL Accu TOF Dart at the Mass Spectrometry Facility at Boston College with the assistance from Marek Domin. Stern-Volmer quenching experiments were performed on Varian Cary Eclipse fluorescence spectrophotometer.

Synthesis of Catalysts (4CzIPN and 4-ClOBzBu4N) and Substrates

4CzIPN

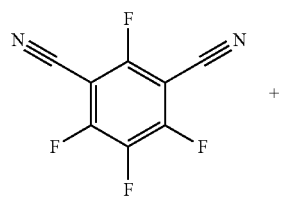

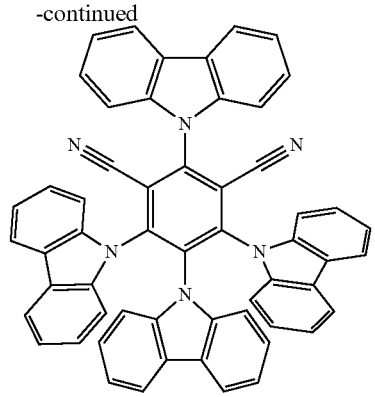

Catalyst 4CzIPN was prepared according to the previously reported procedures (29). To a 250 mL oven-dried round bottom flask, NaH (60% in mineral oil, 1.20 g, 30.0 mmol) was added slowly to the solution of carbazole (3.34 g, 20.0 mmol) in dry THF (80 mL) under nitrogen atmosphere at room temperature. After 30 min, tetrafluoroisophthalonitrile (0.80 g, 4.00 mmol) was added. The resulting reaction mixture was further stirred at room temperature for 12 h and quenched by slow addition of 4.0 mL water. The resulting mixture was then concentrated under reduced pressure and washed with water and EtOH to get rid of the majority of the remaining carbazole. The crude product was then purified by column chromatography on silica gel with $CH_2C_2$/hexane, 2/1 to 4/1 v/v to give 2.91 g (92%) as yellow solid. $^1H$ NMR (400 MHz, $CD_2C_2$) δ 8.33 (d, J=7.7 Hz, 2H), 7.84-7.77 (m, 8H), 7.60-7.56 (m, 2H), 7.44 (d, J=7.6 Hz, 2H), 7.35-7.31 (m, 4H), 7.21-7.16 (m, 8H), 6.99 (d, J=8.2 Hz, 2H), 6.91 (t, J=7.4 Hz, 2H), 6.74 (t, J=7.7 Hz, 2H). $^{13}C$ NMR (100 MHz, $CD_2Cl_2$) δ 145.68, 145.07, 140.30, 138.62, 137.51, 135.49, 127.43, 126.28, 125.34, 125.17, 124.76, 124.16, 122.85, 122.35, 121.74, 121.46, 120.81, 120.02, 116.99, 112.17, 110.46, 110.04.

4-ClOBzBu4N

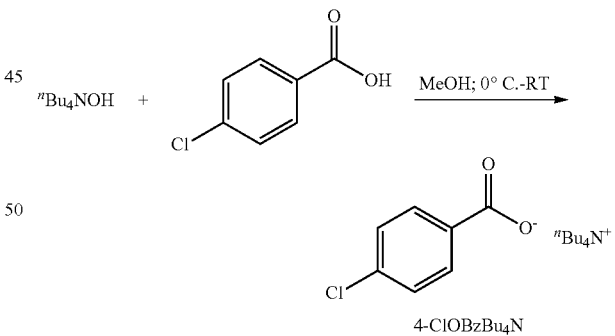

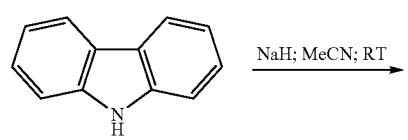

Into a 100 mL oven-dried round bottom flask, 4-chlorobenzoic acid (1.0 eq, 20 mmol) was added and followed by the addition of 10 mL dry MeOH under the nitrogen atmosphere. The reaction was cooled down to 0° C. in an ice bath, then 20 mL of tetrabutylammonium hydroxide (1M in methanol solution) was added dropwise. Upon the completion of slow addition, the reaction was warmed up to room temperature and stirred for 3 hours. After the reaction was completed, solvent was removed under vacuum. The reaction mixture was transferred into a vacuum oven at 40° C. for 72 hours to remove the water residue. Upon cooling down, the product, a white solid, was stored in a dry desiccator. $^1$H NMR (400 MHz, CDCl$_3$) δ 7.99 (d, J=8.4 Hz, 2H), 7.20 (d, J=8.4 Hz, 2H), 3.27-3.22 (m, 8H), 1.60-1.52 (m, 8H), 1.40-1.32 (m, 8H), 0.92 (t, J=7.3 Hz, 12H). $^{13}$C NMR (100 MHz, CDCl$_3$) δ 170.20, 139.36, 134.25, 130.88, 127.08, 58.63, 23.93, 19.63, 13.58.

Reaction Procedure for Substrate Scope (0.3 Mmol Reaction Scale)

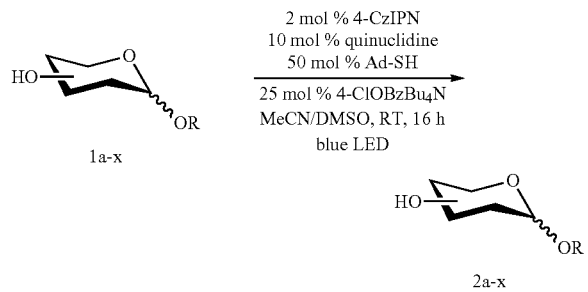

Into a 2-dram vial, methyl α-D-glucopyranoside 1a (58.3 mg, 0.3 mmol), 4CzIPN (4.7 mg, 2 mol %), 1-adamantanethiol (25.2 mg, 50 mol %), quinuclidine (3.3 mg, 10 mol %) and 4-ClOBzBu4N (29.8 mg, 25 mol %) were subsequently added. A 10×3 mm PTFE magnetic stir bar was added, and the vial was slightly capped and transferred into a nitrogen-filled purge box. Dry and degassed MeCN/DMSO (10/1 v/v, 1.5 mL) was added. The vial was then capped with a polypropylene screw cap with a bonded PTFE faced silicone liner and then removed from the purge box. The vial was immediately wrapped with parafilm. The reaction vessel was then placed 5 cm from a LED Kessil lamp and stirred at 600 rpm with cooling fans (shown below). After 16 hours, the crude reaction mixture was concentrated and analyzed by $^1$H NMR spectroscopy with 4-fluoroanisole as analytical standard. Note 1: Unless otherwise noted, the reported yield is the isolated yield of two duplicate reactions. Note 2: Unless otherwise stated, the reactions could be run under Kessil 420, 440, 456, or blue with similar reaction yields as shown below.

(D)-β-glucopyranosylthymine

Substrate 1q was prepared using previously reported procedures (30, 31).

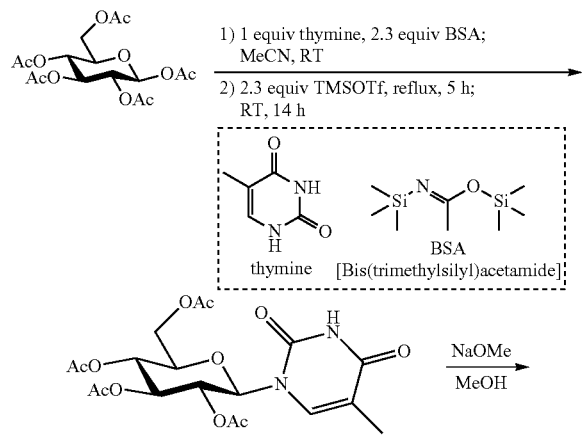

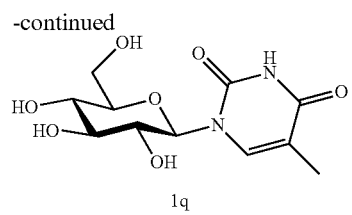

To a mixture of 1,2,3,4,6-Penta-O-acetyl-D-galactopyranose (2.00 g, 5.12 mmol) and thymine (646 mg, 5.12 mmol) in anhydrous MeCN (30 mL), was added N,O-bis(trimethylsilyl)acetamide (2.9 mL, 11.8 mmol). After stirring at room temperature until a clear solution was obtained, trimethylsilyl triflate (2.3 mL, 12 mmol) was added and the reaction mixture was stirred under reflux for 5 h, followed by 14 h at room temperature. The reaction mixture was then diluted with ethyl acetate and washed with water, aq. NaHCO$_3$ solution and brine. The organic phase was then dried over Na$_2$SO$_4$, concentrated under reduced vacuum, and purified using column chromatography (EtOAc/Hexanes, 20%-60%) to give (2',3',4',6'-tetra-O-acetyl-β-D-glucopyranoside)-thymine in 76% yield. Hexanes/EtOAc=1:1, R$_f$=0.3. $^1$H NMR (400 MHz, CDCl$_3$) δ 8.36 (s, 1H), 7.13 (d, J=1.6 Hz, 1H), 5.85 (d, J=9.5 Hz, 1H), 5.38 (t, J=9.5 Hz, 1H), 5.25-5.09 (m, 2H), 4.27 (dd, J=12.6, 5.1 Hz, 1H), 4.12 (dd, J=12.6, 2.1 Hz, 1H), 3.92 (ddd, J=10.3, 5.1, 2.0 Hz, 1H), 2.10 (s, 3H), 2.06 (s, 3H), 2.02 (s, 3H), 2.00 (s, 3H), 1.96 (d, J=1.2 Hz, 3H). $^{13}$C NMR (150 MHz, CDCl$_3$) δ 170.64, 169.89, 169.64, 169.61, 162.99, 150.40, 134.63, 112.42, 80.41, 75.09, 72.91, 69.41, 67.94, 61.83, 20.88, 20.70, 20.66, 20.51, 12.75. HRMS (DART) ([M+H]$^+$) Calcd. for C19H25N2O11: 457.1453, found 457.1458.

(2',3',4',6'-Tetra-O-acetyl-β-D-glucopyranoside)-thymine (1.00 g, 2.19 mmol) and sodium methoxide (81 mg, 1.5 mmol) were added to a 100 mL round bottom flask equipped with a stir bar. The reaction vessel was capped with a septa and purged with nitrogen for 10 min. Then, anhydrous MeOH (43 mL) was added via syringe. After stirring at room temperature for 2 h, the reaction was quenched with diluted HCl in MeOH (125 μL 36% HCl in 10 mL MeOH). Solvent was removed by reduced pressure, and the product was used directly. $^1$H NMR (400 MHz, Deuterium Oxide) δ 7.54 (s, 1H), 5.52 (d, J=8.9 Hz, 1H), 3.82 (dd, J=12.5, 2.2 Hz, 1H), 3.72-3.53 (m, 4H), 3.45 (t, J=9.3 Hz, 1H), 1.82 (s, 3H). $^{13}$C NMR (150 MHz, D$_2$O) δ 166.91, 152.74, 138.00, 112.67, 83.27, 79.23, 76.68, 71.73, 69.67, 61.13, 12.04. HRMS (DART) ([M+H]$^+$) Calcd. for C11H17N2O7: 289.1030, found 289.1024.

Reaction Procedure for Gram-Scale Reactions (3-6 mmol)

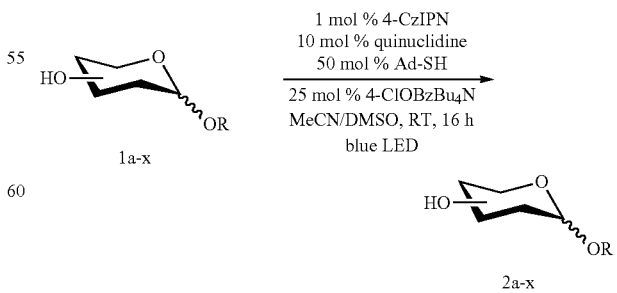

Into a 40 mL vial, methyl α-D-glucopyranoside 1a (1.164 g, 6 mmol), 4CzIPN (0.048 g, 1 mol %), 1-adamantanethiol (0.504 g, 50 mol %), quinuclidine (0.066 g, 10 mol %) and 4-ClOBzBu4N (0.596 g, 25 mol %) were subsequently added. A PTFE magnetic stir bar was added, and the vial was slightly capped and transferred into a nitrogen-filled purge box. Dry and degassed MeCN/DMSO (10/1 v/v, 25 mL) was added. The vial was then capped, sealed with electrical tape, and then removed from the purge box. The reaction vessel was then placed 5 cm from two blue LED Kessil lamps and stirred at 600 rpm with cooling fans (shown below). After 16 hours, the crude reaction mixture was concentrated and analyzed by $^1$H NMR spectroscopy with 4-fluoroanisole as analytical standard.

General Reaction Procedure for Sugar Epimerization
Reaction Procedure for Condition Optimization

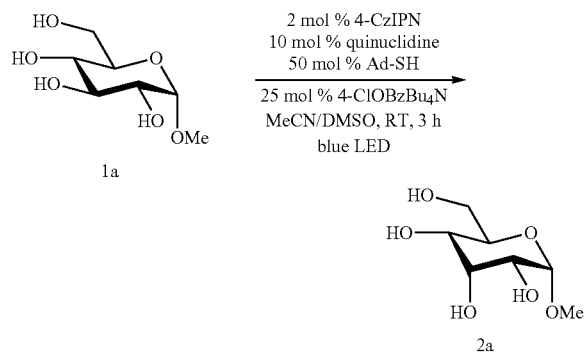

Into a 1-dram vial, methyl α-D-glucopyranoside 1a (19.4 mg, 0.1 mmol), 4CzIPN (1.6 mg, 2 mol %), 1-adamantanethiol (8.4 mg, 50 mol %), quinuclidine (1.1 mg, 10 mol %) and 4-ClOBzBu4N (9.9 mg, 25 mol %) were subsequently added. A 10×3 mm PTFE magnetic stir bar was added, and the vial was slightly capped and transferred into a nitrogen-filled purge box. Dry and degassed MeCN/DMSO (10/1 v/v, 0.5 mL) was added. The vial was then capped with a polypropylene screw cap with a bonded PTFE faced silicone liner and then removed from the purge box. The vial was immediately wrapped with parafilm. The reaction vessel was then placed 5 cm from a LED Kessil lamp and stirred at 300 rpm with a cooling fan (shown below). After 3 hours, the crude reaction mixture was concentrated and analyzed by $^1$H NMR spectroscopy with 4-fluoroanisole as analytical standard.

General Procedure for Purification of Epimeric Sugars
Procedure A (Direct Column Chromatography)

The duplicated reactions were dissolved in methanol and mixed together after crude $^1$H NMR analysis. To the mixture, potassium hexafluorophosphate (KPF$_6$, 1.1 equiv. based on 4-ClOBzBu$_4$)) was added in order to form TBAPF$_6$ to ease the removal of TBAOBz(4-Cl). The solution was then concentrated under vacuum. The desired compound was then directly purified by flash column chromatography with gradient eluent as indicated in each specific product.

Procedure B (Peracetylation and Deacetylation):
Pre-Purification

The duplicated reactions were dissolved in methanol and mixed together after crude $^1$H NMR analysis. To the mixture, potassium hexafluorophosphate (KPF$_6$, 1.1 equiv. based on 4-ClOBzBu$_4$N, 30.4 mg) was added in order to form TBAPF$_6$ to ease the removal of 4-ClOBzBu$_4$N. The solution was concentrated under vacuum and then underwent a quick purification with flash column chromatography to get rid of 4-CzIPN, thiol, quinuclidine, and TBAOBz(4-Cl) by using DCM/MeOH (0% to 2.5%) as eluent followed by 50% to flush the desired product off the column. (Note: For certain sugars, the addition of water to the DCM/MeOH eluent was used.)

Acetylation
To the pre-purified mixture, acetic anhydride (0.2 M, 2 mL) was added, followed by sodium acetate (0.2 equiv. per "OH"). The resulting reaction solution was stirred at 80° C. under nitrogen atmosphere and monitored by TLC. Upon the completion, the reaction was quenched by water and extracted with diethyl ether for three times. The combined organic phase was then washed with sat. NaHCO$_3$, dried over Na$_2$SO$_4$, concentrated, and purified using column chromatography with the combination of hexanes/Et$_2$O.

Deacetylation:
Under nitrogen atmosphere, the acetylated sugar was dissolved in anhydrous MeOH, then MeONa (0.375 equiv. per "OH") was added at 0° C. The resulting solution was gradually warmed up, stirred at RT and monitored by TLC. Upon the completion, the reaction was neutralized by Amberlyst-15 and then filtered. The filtrate was then concentrated under reduced pressured to give the titled compound. (Note: For certain sugars, the overuse of acidic resin will lead to sugar decomposition.)

Procedure C (Ion-Exchange Column Chromatography)
Resin Preparation (50WX8-Ca$^{2+}$) (32): Dowex 50WX8 (200-400 mesh) resin in the hydrogen form (50WX8-H, 250 g) was stirred in the aqueous CaCl$_2$ solution (4 M, 750 mL) for 12 hours to exchange the H$^+$ form to the Ca$^{2+}$ form. The resulting mixture was decanted onto a Buchner funnel and washed with water for at least four times (4×1 L) until there is no change in the pH of the filtrate water. (Note: Special care is needed when preparing highly concentrated CaCl$_2$) solution, which is very exothermic and suggested to process in an ice bath.)

Ion-Exchange Column Chromatography
Dowex 50WX8-Ca$^{2+}$ (200-400 mesh) in the Ca$^{2+}$ form was loaded into a thin and long cylindrical ion-exchange column (see details in specific case below). The crude material was loaded with 1-2 mL of water via a long-needle syringe and eluted with water. The flow rate was maintained at a rate around 1.5 mL/min and the fractions were taken every 1.5-2.0 mL. Fractions were collected on the basis of the intensity of the spots on the TLC stained with anisaldehyde or visualized by UV light, as well as $^1$H NMR analysis.

Exemplary Product Characterization

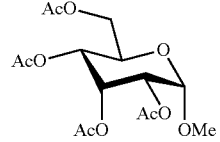

(D)-α-methylallose tetraacetate 2a': The reaction of 1a was proceeded according to the representative reaction procedure B. The purification followed general purification procedure B. Peracetylation reaction: Prepared according to general procedure of purification B-acetylation with the eluent hexanes/Et$_2$O (0%-66%). Hexanes/Et$_2$O=1:2, R$_f$=0.3. [α]$^{20}_D$=+92° (c=1, CHCl$_3$). $^1$H NMR (400 MHz, CDCl$_3$) δ 5.64 (t, J=3.2 Hz, 1H), 5.00-4.95 (m, 2H), 4.88 (d, J=4.2 Hz, 1H), 4.31-4.25 (m, 2H), 4.19-4.16 (m, 1H), 3.44 (s, 3H), 2.16 (s, 3H), 2.09 (s, 6H), 1.99 (s, 3H). $^{13}$C NMR (100 MHz, CDCl$_3$) δ 170.71, 170.66, 169.77, 169.12, 96.95, 67.22, 67.19, 65.83, 63.38, 62.11, 55.93, 20.95, 20.72, 20.51. IR (neat, cm$^{-1}$): 2941 (br), 1742 (s), 1372 (m), 1223 (s), 1041 (s), 912 (w), 749 (w). HRMS (DART) ([M+H]$^+$) Calcd. for C15H23O10: 363.1286, found 363.1287.

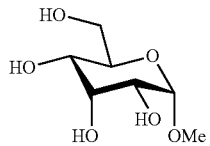

(D)-α-methylallose 2a (23): Prepared from 2a' according to the general purification procedure B. DCM/MeOH=4:1, $R_f$=0.1. [α]$^{20}_D$=+140° (c=1, MeOH). $^1$H NMR (500 MHz, MeOD) δ 4.68 (d, J=3.9 Hz, 1H), 3.97 (t, J=2.8 Hz, 1H), 3.87-3.81 (m, 1H), 3.73-3.66 (m, 2H), 3.59 (t, J=3.6 Hz, 1H), 3.46 (dd, J=9.6, 3.0 Hz, 1H), 3.42 (s, 3H). $^{13}$C NMR (125 MHz, MeOD) δ 101.49, 73.39, 69.45, 68.93, 68.25, 62.72, 56.07. IR (neat, cm$^{-1}$): 3361 (br), 2931 (m), 1597 (w), 1104 (w), 1104 (m), 1041 (s). HRMS (DART) ([M+H]$^+$) Calcd. for C7H15O6: 195.0863, found 195.0861.

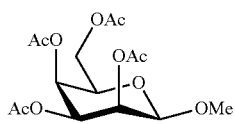

(D)-β-methyltalose tetraacetate 2b': The reaction of 1b proceeded according to the representative reaction procedure B. The purification followed general purification procedure B. Peracetylation reaction: Prepared according to general procedure of purification B, acetylation. Hexanes/Et$_2$O=1:4, $R_f$=0.2. [α]$^{20}_D$=−35° (c=1, CHCl$_3$). $^1$H NMR (400 MHz, CDCl$_3$) δ 5.42-5.36 (m, 1H), 5.31-5.25 (m, 1H), 5.06 (t, J=3.7 Hz, 1H), 4.52 (d, J=1.5 Hz, 1H), 4.32-4.21 (m, 2H), 3.91 (td, J=6.7, 1.6 Hz, 1H), 3.56 (s, 3H), 2.16 (s, 3H), 2.13 (s, 3H), 2.05 (s, 3H), 2.00 (s, 3H). $^{13}$C NMR (100 MHz, CDCl$_3$) δ 170.60, 170.48, 170.31, 169.77, 100.25, 71.53, 68.08, 67.04, 65.05, 61.63, 57.54, 21.00, 20.82, 20.78, 20.68. IR (neat, cm$^{-1}$): 1737 (s), 1368 (m), 1218 (s), 1076 (m), 1047 (m), 1024 (m), 933 (w), 728 (s). HRMS (DART) ([M+H]$^+$) Calcd. for C15H23O10: 363.1286, found 363.1288.

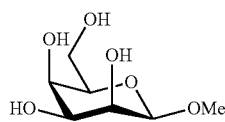

(D)-β-methyltalose 2b (33): Prepared according to general procedure of purification B, deacetylation. DCM/MeOH=4:1, $R_f$=0.1. [α]$^{20}_D$=−45° (c=1, MeOH). $^1$H NMR (400 MHz, MeOD) δ 4.35 (d, J=1.0 Hz, 1H), 3.84 (dt, J=2.5, 1.0 Hz, 1H), 3.82-3.73 (m, 3H), 3.57 (d, J=3.2 Hz, 4H), 3.44 (ddd, J=6.7, 5.6, 1.2 Hz, 1H). $^{13}$C NMR (100 MHz, MeOD) δ 103.34, 77.46, 72.88, 72.86, 70.66, 70.28, 62.46, 57.22. IR (neat, cm$^{-1}$): 3335 (br), 2933 (m), 2855 (m), 1652 (m), 1597 (m), 1306 (m), 1904 (s), 1055 (s), 875 (w), 768 (w). HRMS (DART) ([M+H]$^+$) Calcd. for C7H15O6: 195.0863, found 195.0860.

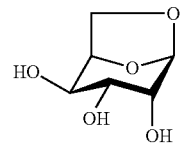

(D)-anhydrogulose 2c: Proceeded according to the representative reaction procedure B. The purification followed general purification procedure A with RediSep R$_f$ Gold® Amine column, 30 g, from Teledyne ISCO (69-2203-506) using DCM/MeOH (0%-20%). DCM/MeOH=6:1, $R_f$=0.25. [α]$^{20}_D$=+29° (c=1, MeOH). $^1$H NMR (400 MHz, MeOD) δ 5.29 (d, J=2.4 Hz, 1H), 4.32 (t, J=4.6 Hz, 1H), 3.97 (dd, J=7.7, 0.7 Hz, 1H), 3.78 (ddd, J=9.1, 4.2, 1.0 Hz, 1H), 3.69 (dd, J=4.8, 2.4 Hz, 1H), 3.59-3.53 (m, 2H). $^{13}$C NMR (100 MHz, MeOD) δ 103.17, 76.19, 72.00, 71.13, 71.11, 64.29. IR (neat, cm$^{-1}$): 3400 (br), 2966 (w), 1912 (w), 1413 (w), 1224 (w), 1127 (s), 1087 (s), 1023 (m), 965 (m), 922 (w), 832 (w). HRMS (DART) ([M+H]$^+$) Calcd. for C6H11O5: 163.0601, found 163.0595.

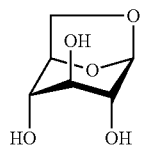

(D)-anhydrotalose 3c: Proceeded according to the representative reaction procedure B. The purification followed general purification procedure A with RediSep R$_f$ Gold® Amine column, 30 g, from Teledyne ISCO (69-2203-506) using DCM/MeOH (0%-20%). DCM/MeOH=6:1, $R_f$=0.25. [α]$^{20}_D$=−94° (c=1, MeOH). $^1$H NMR (600 MHz, MeOD) δ 5.18 (br, J=1.8 Hz, 1H), 4.42 (d, J=7.0 Hz, 1H), 4.26 (t, J=4.7 Hz, 1H), 4.08 (ddt, J=5.0, 3.5, 1.3 Hz, 1H), 3.85-3.79 (m, 1H), 3.60-3.56 (m, 1H), 3.54 (dd, J=5.0, 1.8 Hz, 1H). $^{13}$C NMR (150 MHz, MeOD) δ 102.75, 75.98, 70.51, 70.47, 68.52, 65.58. IR (neat, cm$^{-1}$): 3369 (br), 2918 (m), 1406 (w), 1340 (w), 1134 (s), 1066 (s), 1027 (s), 965 (m), 792 (m), 729 (w), 670 (w). HRMS (DART) ([M+NH$_4$]$^+$) Calcd. for C6H14NO5: 180.0866, found 180.0860.

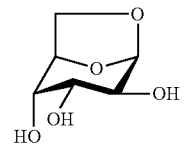 [SMILES: OC1[C@@H]2OCC(O2)[C@@H](O)[C@@H]1O]

(D)-anhydroaltrose 2d (34): Proceeded according to the representative reaction procedure B with the following change: 5 mol % quinuclidine. The purification followed general purification procedure A with RediSep R$_f$ Gold® Amine column, 30 g, from Teledyne ISCO (69-2203-506) using DCM/MeOH (0%-20%). DCM/MeOH=6:1, $R_f$=0.2. [α]$^{20}_D$=−166° (c=1, MeOH). $^1$H NMR (400 MHz, MeOD) δ 5.21 (d, J=1.7 Hz, 1H), 4.57-4.48 (m, 1H), 3.82-3.77 (m, 1H), 3.73-3.67 (m, 2H), 3.59 (dd, J=8.7, 4.5 Hz, 1H), 3.52 (dd, J=8.7, 1.7 Hz, 1H). $^{13}$C NMR (100 MHz, MeOD) δ 103.34, 78.43, 74.40, 71.58, 71.24, 66.41. IR (neat, cm$^{-1}$): 3370 (br), 2916 (w), 1409 (w), 1337 (w), 1226 (w), 1132

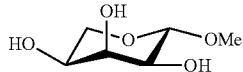

(L)-β-methylribopyranose 2e (35): Proceeded according to the representative reaction procedure B. The purification followed general purification procedure A with RediSep R$_f$ Gold® Amine column, 30 g, from Teledyne ISCO (69-2203-506) using DCM/MeOH (0%-20%). DCM/MeOH=6:1, R$_f$=0.4. $[\alpha]^{20}_D$=+126° (c=1, MeOH). $^1$H NMR (400 MHz, MeOD) δ 4.61 (d, J=3.7 Hz, 1H), 3.81 (t, J=3.1 Hz, 1H), 3.79-3.72 (m, 2H), 3.66 (dd, J=12.3, 5.3 Hz, 1H), 3.55 (td, J=3.7, 1.2 Hz, 1H), 3.40 (s, 3H). $^{13}$C NMR (100 MHz, MeOD) δ 103.42, 72.47, 70.63, 68.09, 64.78, 55.97. IR (neat, cm$^{-1}$): 3395 (br), 2936 (w), 1445 (w), 1199 (w), 1130 (m), 1095 (m), 1059 (s), 978 (m), 919 (m), 825 (m), 728 (m). HRMS (DART) ([M+NH$_4$]$^+$) Calcd. for C6H16NO5: 182.1023, found 182.1014.

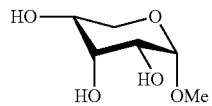

(D)-α-methylribose 3e (same as 2f) (36): DCM/MeOH=6:1, R$_f$=0.3. $[\alpha]^{20}_D$=+84° (c=1, MeOH). $^1$H NMR (400 MHz, MeOD) δ 4.48 (d, J=2.9 Hz, 1H), 3.85 (t, J=3.2 Hz, 1H), 3.75 (dd, J=11.1, 8.1 Hz, 1H), 3.69-3.63 (m, 2H), 3.49-3.40 (m, 4H). $^{13}$C NMR (100 MHz, MeOD) δ 101.85, 72.08, 70.71, 68.87, 61.73, 56.47. IR (neat, cm$^{-1}$): 3427 (br), 2932 (w), 1408 (w), 1129 (w), 1082 (m), 1044 (s), 999 (w), 887 (w), 764 (w). HRMS (DART) ([M+NH$_4$]$^+$) Calcd. for C6H16NO5: 182.1023, found 182.1018.

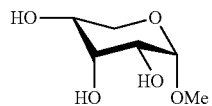

(D)-α-methylribose 2f (36): Proceeded according to the representative reaction procedure B. The purification followed general purification procedure A using DCM/MeOH (0%-20%). DCM/MeOH=6:1, R$_f$=0.3. $[\alpha]^{20}_D$=+87° (c=1, MeOH). $^1$H NMR (400 MHz, MeOD) δ 4.49 (d, J=3.0 Hz, 1H), 3.86 (br, 1H), 3.75 (dd, J=11.1, 8.2 Hz, 1H), 3.70-3.63 (m, 2H), 3.47-3.41 (m, 4H). $^{13}$C NMR (100 MHz, MeOD) δ 101.85, 72.08, 70.71, 68.87, 61.73, 56.47. IR (neat, cm$^{-1}$): 3316 (br), 2929 (w), 1254 (w), 1133 (m), 1082 (m), 1046 (s), 999 (m), 964 (w0, 890 (2), 764 (w). HRMS (DART) ([M+NH$_4$]$^+$) Calcd. for C6H16NO5: 182.1023, found 182.1016.

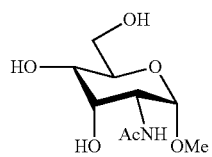

N-acetylallosamine 2g (37): Prepared according to the general reaction procedure B and purified with general purification procedure A with the eluent from DCM/MeOH (0%-10%). DCM/MeOH=10:1, R$_f$=0.2. $[\alpha]^{20}_D$=+78° (c=1, MeOH). $^1$H NMR (400 MHz, MeOD) δ 4.67 (d, J=3.9 Hz, 1H), 4.06 (t, J=3.5 Hz, 1H), 3.93 (t, J=3.1 Hz, 1H), 3.87-3.79 (m, 1H), 3.79-3.71 (m, 2H), 3.54 (dd, J=9.8, 3.1 Hz, 1H), 3.40 (s, 3H), 2.02 (s, 3H). $^{13}$C NMR (100 MHz, MeOD) δ 172.98, 99.74, 71.39, 68.90, 68.04, 62.70, 56.03, 51.52, 22.53. IR (neat, cm$^{-1}$): 3329 (br), 2928 (m), 1653 (s), 1537 (s), 1379 (m), 1050 (s), 847 (s). 794 (m). HRMS (DART) ([M+H]$^+$) Calcd. for C9H18NO6: 236.1129, found 236.1124.

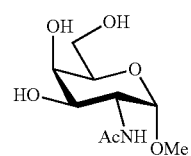

N-acetylgalactosamine 3g: Prepared according to the general reaction procedure and purified with general purification procedure A (direct chromatography) with gradient eluent from DCM/MeOH (0%-10%). DCM/MeOH=10:1, R$_f$=0.15. $[\alpha]^{20}_D$=+158° (c=1, MeOH). $^1$H NMR (500 MHz, MeOD) δ 4.69 (d, J=3.7 Hz, 1H), 4.27 (dd, J=10.9, 3.6 Hz, 1H), 3.88 (d, J=3.1 Hz, 1H), 3.77-3.70 (m, 4H), 3.37 (s, 3H), 1.99 (s, 3H). $^{13}$C NMR (125 MHz, MeOD) δ 173.99, 100.06, 72.35, 70.38, 69.88, 62.84, 55.57, 51.55, 22.62. IR (neat, cm$^{-1}$): 3292 (br), 2912 (m), 2362 (m), 1648 (s), 1546 (s), 1042 (s), 943 (w), 792 (w). HRMS (DART) ([M+H]$^+$) Calcd. for C9H18NO6: 236.1129, found 236.1129.

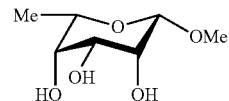

(L)-6-deoxy-β-methyltalose 2h (36, 38): Proceeded according to the representative reaction procedure B. The purification followed general purification procedure A with the eluent DCM/MeOH (0%-20%). DCM/MeOH=6:1, R$_f$=0.4. $[\alpha]^{20}_D$=+59° (c=1, MeOH). $^1$H NMR (400 MHz, MeOD) δ 4.31 (d, J=1.0 Hz, 1H), 3.80 (dt, J=3.1, 1.2 Hz, 1H), 3.59-3.47 (m, 6H), 1.30 (d, J=6.4 Hz, 3H). $^{13}$C NMR (100 MHz, MeOD) δ 103.10, 73.59, 72.66, 70.50, 57.04, 16.70. IR (neat, cm$^{-1}$): 3380 (br), 2935 (w), 1446 (w), 1374 (w), 1212 (w), 1177 (w), 1090 (s), 1061 (s), 1018 (s), 970 (w), 860 (w), 805 (w). HRMS (DART) ([M+H]+) Calcd. for C7H15O5: 179.0914, found 179.0911.

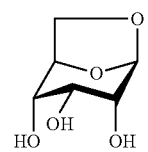

(D)-anhydroallose 2i: Proceeded according to the representative reaction procedure B. The purification followed general purification procedure A with the eluent DCM/MeOH (0%-20%). DCM/MeOH=6:1, R$_f$=0.15. $[\alpha]^{20}_D$=−68° (c=1, MeOH). $^1$H NMR (400 MHz, MeOD) δ 5.36 (d, J=2.6 Hz, 1H), 4.54 (ddd, J=5.6, 2.9, 1.0 Hz, 1H), 3.79-3.73 (m, 2H), 3.70-3.65 (m, 2H), 3.64-3.60 (m, 1H). $^{13}$C NMR (100 MHz, MeOD) δ 102.81, 77.62, 72.02, 71.82, 65.83, 64.61. IR (neat, cm$^{-1}$): 3383 (br), 2908 (w), 1416 (w), 1130 (s), 1101 (s) 1074 (s), 971 (s), 917 (m), 859 (m), 654 (m). HRMS (DART) ([M+H]$^+$) Calcd. for C6H11O5: 163.0601, found 163.0598.

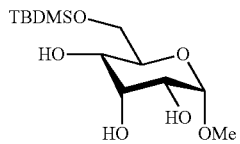

(D)-C6-α-methylglucose 2j: Proceeded according to the representative reaction procedure B. The purification followed general purification procedure A with the eluent DCM/MeOH (0%-10%). DCM/MeOH=10:1, R$_f$=0.3. [α]$^{20}_D$=+81° (c=1, MeOH). $^1$H NMR (400 MHz, MeOD) δ 4.67 (d, J=3.8 Hz, 1H), 4.00-3.92 (m, 2H), 3.82 (dd, J=11.2, 5.5 Hz, 1H), 3.69 (ddd, J=10.2, 5.5, 2.1 Hz, 1H), 3.57 (t, J=3.7 Hz, 1H), 3.46 (dd, J=10.1, 3.2 Hz, 1H), 3.42 (s, 3H), 0.92 (s, 9H), 0.09 (d, J=0.9 Hz, 6H). $^{13}$C NMR (100 MHz, MeOD) δ 101.50, 73.44, 69.55, 69.31, 68.19, 64.18, 55.99, 26.40, 19.27, −5.10, −5.17. IR (neat, cm$^{-1}$): 3398 (br), 2929 (m), 2859 (w), 1389 (w), 1252 (w), 1125 (m), 1049 (s), 837 (m), 776 (m). HRMS (DART) ([M+H]$^+$) Calcd. for C13H29O6Si: 309.1728, found 309.1728.

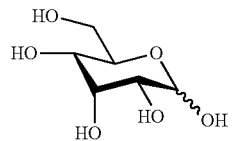

(D)-allose 2k (39): Prepared according to the representative procedures B (0.3 mmol) and C (6 mmol) with the following changes: For 0.3 mmol reaction scale, 2.5 mol % quinuclidine, MeCN/DMSO 3:1, 1.5 mL, the reaction stirred for 6 hours; for 6 mmol reaction scale, 2.5 mol % quinuclidine, 2 mol % 4CzIPN, MeCN/DMSO 3:1, 25 mL, the reaction stirred for 12 hours. The purification of 0.6 mmol reaction followed general purification procedure C (a glass column was packed with ion-exchange resin 1.5 cm diameter×25 cm length). The purification of 6 mmol reaction followed general purification procedure B and then purification procedure C (glass column was packed with ion-exchange resin to 2.5 cm diameter×50 cm length). [α]$^{20}_D$=+12° (c=1, H$_2$O). The compound contains a mixture of four isomers (α-pyanoside, β-pyranoside, α-furanoside and β-furanoside) and the major isomer 3-allopyranoside was reported below: $^1$H NMR (500 MHz, D$_2$O) δ 4.89 (d, J=8.2 Hz, 1H), 4.17 (t, J=2.8 Hz, 1H), 3.88 (dd, J=12.2, 1.7 Hz, 1H), 3.81-3.77 (m, 1H), 3.70 (dd, J=12.2, 5.8 Hz, 1H), 3.63 (dd, J=10.0, 2.9 Hz, 1H), 3.41 (dd, J=8.2, 3.0 Hz, 1H). $^{13}$C NMR (100 MHz, D$_2$O) δ 94.02, 74.21, 71.85, 71.77, 67.40, 61.78. IR (neat, cm$^{-1}$): 3326 (br), 2917 (m), 1419 (m), 1254 (m), 1029 (s), 722 (s). HRMS (DART) ([M+NH$_4$]$^+$) Calcd. for C6H16NO6: 198.0972, found 198.0966.

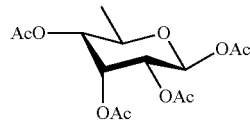

(D)-6-deoxyallose tetraacetate 2l': The reaction of 11 was proceeded according to the representative reaction procedure B with the following changes: MeCN/DMSO 3:1, 1.5 mL. The purification followed general purification procedure B. Peracetylation reaction: Prepared according to general procedure of purification B with the eluent hexanes/Et$_2$O (0%-90%), only the β-isomer of acetylated sugar was isolated. Hexanes/Et$_2$O=1/1, R$_f$=0.4. [α]$^{20}_D$=+8° (c=1, CHCl$_3$). $^1$H NMR (400 MHz, CDCl$_3$) δ 5.96 (d, J=8.6 Hz, 1H), 5.63 (t, J=2.9 Hz, 1H), 4.94 (dd, J=8.6, 3.1 Hz, 1H), 4.68 (dd, J=9.9, 2.7 Hz, 1H), 4.08 (dq, J=9.9, 6.2 Hz, 1H), 2.14 (s, 3H), 2.10 (s, 3H), 2.00 (s, 3H), 1.99 (s, 3H), 1.20 (d, J=6.2 Hz, 3H). $^{13}$C NMR (100 MHz, CDCl$_3$) δ 169.86, 169.35, 169.32, 169.02, 89.94, 70.89, 69.08, 68.42, 68.30, 20.90, 20.64, 20.56, 20.49, 17.18. IR (neat, cm$^{-1}$): 3298 (br), 1746 (s), 1372 (m), 1227 (w), 1042 (s), 912 (w), 749 (w). HRMS (DART)([M+NH$_4$]$^+$) Calcd. for C14H24NO9: 350.1446, found 350.1450.

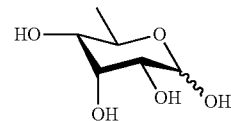

(D)-6-deoxyallose 2l (40): Prepared from 2l' according to the general purification procedure B (deacetylation). DCM/MeOH=6:1, R$_f$=0.2. [α]$^{20}_D$=+3° (c=1, MeOH). The compound contains a mixture of four isomers (α-pyanoside, β-pyranoside, α-furanoside and β-furanoside) and the major isomer β-allopyranoside was reported below: $^1$H NMR (400 MHz, MeOD) δ 4.79 (d, J=8.0 Hz, 1H), 4.01 (t, J=2.9 Hz, 1H), 3.75 (dq, J=9.6, 6.2 Hz, 1H), 3.23 (dd, J=8.0, 3.0 Hz, 1H), 3.16 (dd, J=9.6, 2.9 Hz, 1H), 1.23 (d, J=6.2 Hz, 3H). $^{13}$C NMR (100 MHz, MeOD) δ 95.37, 74.49, 73.85, 72.97, 70.62, 18.25. IR (neat, cm$^{-1}$): 3341 (br), 2905 (m), 1596 (s), 1314 (s), 1077 (s), 901 (w), 708 (w). HRMS (DART) ([M+NH$_4$]$^+$) Calcd. for C6H16NO5: 182.1023, found 182.1021.

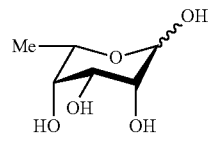

(L)-6-deoxytalose 2m (40): Prepared according to the general reaction procedure B (0.3 mmol reaction scale) and C (3 mmol reaction scale) with the following changes: MeCN/DMSO 3:1, 1.5 mL (0.3 mmol reaction scale) and MeCN/DMSO 3:1, 15 mL, 2 mol % 4CzIPN (3 mmol reaction). Purified with general purification procedure A (direct chromatography) with gradient eluent DCM/MeOH (0%-10%). DCM/MeOH=6:1, R$_f$=0.2. [α]$^{20}_D$=−28° (c=1, MeOH). The compound contains a mixture of four isomers (α-pyanoside, β-pyranoside, α-furanoside and β-furanoside) and the major isomer α-talopyranoside was reported below: $^1$H NMR (400

MHz, MeOD) δ 5.10 (d, J=1.5 Hz, 1H), 4.09 (q, J=6.6 Hz, 1H), 3.78 (t, J=3.2 Hz, 1H), 3.68-3.66 (m, 1H), 3.59-3.58 (m, 1H), 1.23 (d, J=6.6 Hz, 3H). $^{13}$C NMR (100 MHz, MeOD) δ 96.55, 74.54, 72.97, 67.65, 67.06, 17.05. IR (neat, cm$^{-1}$): 3393 (br), 2935 (m), 1418 (w), 1088 (s), 970 (m), 811 (m), 689 (w). HRMS (DART) ([M+NH$_4$]$^+$) Calcd. for C6H16NO5: 182.1023 found 182.1017.

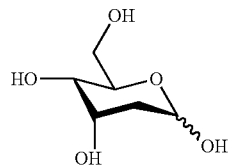

(D)-2-deoxyallose 2n (41): Prepared according to the representative reaction procedures B (0.3 mmol) and C (6 mmol) with the following changes: For 0.3 mmol reaction scale, MeCN/DMSO 3:1, 1.5 mL; for 6 mmol reaction scale, 2 mol % 4CzIPN, MeCN/DMSO 3:1, 25 mL. Purified with general purification procedure A with gradient eluent DCM/MeOH (0%-10%), the desired product eluents first and has a distinctive blue color with p-anisaldehyde stain that differs from starting material. DCM/MeOH=6:1, R$_f$=0.2. [α]$^{20}_D$=+35° (c=1, MeOH). The compound contains a mixture of four isomers (α-pyanoside, β-pyranoside, α-furanoside and β-furanoside) and the major isomer 3-allopyranoside was reported below: $^1$H NMR (400 MHz, MeOD) δ 5.11 (dd, J=9.6, 2.0 Hz, 1H), 4.06 (dd, J=6.1, 3.0 Hz, 1H), 3.83 (dt, J=11.7, 3.1 Hz, 1H), 3.79-3.73 (m, 1H), 3.69-3.63 (m, 1H), 3.86-3.81 (m, 1H), 2.09-2.00 (m, 1H), 1.64 (ddd, J=13.5, 9.7, 2.7 Hz, 1H). $^{13}$C NMR (100 MHz, MeOD) δ 91.55, 74.12, 67.78, 67.53, 62.19, 38.98. IR (neat, cm$^{-1}$): 3339 (br), 2930 (m), 1427 (w), 1340 (w), 1055 (s), 846 (m), 723 (w). HRMS (DART) ([M+NH$_4$]$^+$) Calcd. for C6H16NO5: 182.1023, found 182.1015.

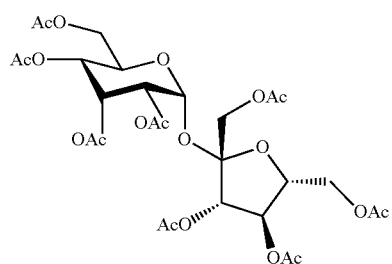

(D)-allosucrose octaacetate 2o' (42): The reaction of 1o was proceeded according to the representative reaction procedure B with the following change: MeCN/DMSO 3:1, 1.5 mL. The purification followed general purification procedure B. Peracetylation reaction: Prepared according to general procedure of purification B, acetylation. Et$_2$O/hexanes=4:1, R$_f$=0.1. [α]$^{20}_D$=+48° (c=1, CHCl$_3$). $^1$H NMR (400 MHz, CDCl$_3$) δ 5.65 (t, J=3.3 Hz, 1H), 5.60 (d, J=4.4 Hz, 1H), 5.49-5.40 (m, 2H), 4.97-4.93 (m, 2H), 4.51 (ddd, J=10.7, 4.5, 2.2 Hz, 1H), 4.40-4.16 (m, 7H), 2.15 (s, 3H), 2.13-2.07 (m, 17H), 2.01 (s, 3H). $^{13}$C NMR (101 MHz, CDCl$_3$) δ 170.90, 170.64, 170.53, 170.32, 170.12, 169.73, 169.56, 169.29, 103.92, 89.58, 78.72, 75.82, 74.98, 67.20, 66.86, 65.75, 64.72, 63.97, 63.37, 62.07, 21.00, 20.88, 20.85, 20.83, 20.80, 20.69. IR (neat, cm$^{-1}$): 1739 (s), 1434 (w), 1369 (m), 1213 (s), 1038 (s), 905 (m), 734 (m). HRMS (DART) ([M+H]$^+$) Calcd. for C28H42O19N: 696.2346, found 696.2319.

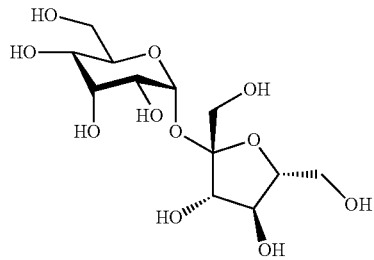

(D)-allosucrose 2o (42): Prepared from 2o according to general procedure of purification B, deacetylation. [α]$^{20}_D$=+30° (c=1, MeOH). $^1$H NMR (400 MHz, MeOD) δ 5.38 (d, J=4.0 Hz, 1H), 4.12-3.98 (m, 3H), 3.95 (ddd, J=10.2, 4.4, 2.5 Hz, 1H), 3.85 (dd, J=11.9, 2.5 Hz, 1H), 3.82-3.71 (m, 4H), 3.71-3.58 (m, 3H), 3.55 (dd, J=10.2, 3.1 Hz, 1H). $^{13}$C NMR (100 MHz, MeOD) δ 105.45, 93.68, 83.94, 79.46, 75.53, 73.17, 69.85, 68.78, 67.69, 64.07, 63.19, 62.18. IR (neat, cm-1):3295 (br), 2924 (w), 1593 (m), 1317 (m), 1048 (s), 979 (m). HRMS (ESI) ([M+Na]$^+$) Calcd. for C12H22O11Na: 365.1060, found 365.1065.

(D)-alloraffinose undecaacetate 2p': The reaction of 1p was proceeded according to the representative reaction procedure B with the following changes: MeCN/DMSO 3:1, 1.5 mL. Proceeded according to the representative reaction procedure B. The purification followed general purification procedure B. Peracetylation reaction: Prepared according to general procedure of purification B-acetylation with the eluent hexanes/Et$_2$O (0%-90%). Hexanes/Et$_2$O=1:10, R$_f$=0.3. [α]$^{20}_D$=+80° (c=1, CHCl$_3$). $^1$H NMR (400 MHz, CDCl$_3$) δ 5.64 (t, J=3.0 Hz, 1H), 5.54 (d, J=4.2 Hz, 1H), 5.46-5.41 (m, 3H), 5.33 (dd, J=10.8, 3.3 Hz, 1H), 5.15 (d, J=3.6 Hz, 1H), 5.08 (dd, J=10.8, 3.6 Hz, 1H), 4.91-4.88 (m, 2H), 4.49 (dd, J=10.5, 4.4 Hz, 1H), 4.42-4.25 (m, 5H), 4.21 (d, J=12.1 Hz, 1H), 4.13 (dd, J=11.2, 6.4 Hz, 1H), 4.04 (dd, J=11.2, 6.9 Hz, 1H), 3.73 (dd, J=11.2, 5.7 Hz, 1H), 3.63 (d, J=9.9 Hz, 1H), 2.18 (s, 3H), 2.12-2.08 (m, 21H), 2.03 (s, 3H), 2.01 (s, 3H), 1.95 (s, 3H). $^{13}$C NMR (100 MHz, CDCl$_3$) δ 170.51, 170.44, 170.38, 170.16, 170.13, 170.05, 169.65, 169.56, 169.30, 168.97, 104.20, 96.05, 89.69, 78.56, 77.20, 76.08, 75.03, 68.21, 68.15, 67.33, 66.94, 66.68, 66.27, 65.94, 65.52, 63.62, 62.40, 61.63, 20.88, 20.73, 20.70, 20.67, 20.62, 20.60, 20.57, 20.55, 20.49. IR (neat, cm$^{-1}$):

3476 (br), 2963 (w), 1740 (s), 1370 (s), 1216 (s), 1040 (s), 755 (s). HRMS (DART) ([M+NH$_4$]$^+$) Calcd. for C40H58O27N: 984.3196, found 984.3180.

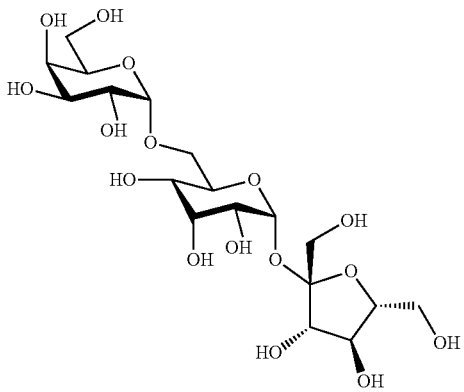

(D)-alloraffinose 2p: Prepared from 2p' according to the general purification procedure B (deacetylation). $[\alpha]^{20}_D$=+84° (c=1, MeOH). $^1$H NMR (400 MHz, MeOD) δ 5.41 (d, J=3.8 Hz, 1H), 4.93 (d, J=3.3 Hz, 1H), 4.18-4.11 (m, 3H), 4.04 (t, J=3.0 Hz, 1H), 3.96-3.88 (m, 3H), 3.83-3.60 (m, 11H), 3.57 (dd, J=10.1, 3.1 Hz, 1H). $^{13}$C NMR (100 MHz, MeOD) δ 105.48, 100.63, 93.50, 83.68, 79.14, 75.20, 73.10, 72.43, 71.45, 71.10, 70.52, 69.03, 68.64, 68.41, 68.26, 64.09, 62.97, 62.83. IR (neat, cm$^{-1}$): 3279 (br), 2923 (m), 1594 (s), 1349 (m), 1048 (s), 990 (s), 766 (w). HRMS (ESI) ([M+Na]$^+$) Calcd. for C18H32O16Na: 527.1583, found 527.1588.

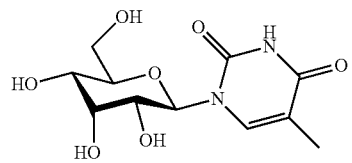

(D)-β-allopyranosylthymine 2q: Proceeded according to the representative reaction procedure B with the following change: MeCN/DMSO 3:1, 1.5 mL. The purification of a 0.3 mmol reaction followed general purification procedure C (a glass column was packed with ion-exchange resin 1.5 cm diameter×35 cm length). $[\alpha]^{20}_D$=+3° (c=1, H$_2$O). $^1$H NMR (400 MHz, D$_2$O) δ 7.62 (d, J=1.6 Hz, 1H), 5.84 (d, J=9.6 Hz, 1H), 4.31 (t, J=3.0 Hz, 1H), 4.00-3.85 (m, 3H), 3.80-3.71 (m, 2H), 1.91 (s, 3H). $^{13}$C NMR (150 MHz, D$_2$O) δ 167.03, 152.97, 138.12, 112.59, 80.71, 76.25, 71.77, 68.78, 66.89, 61.44, 12.07. IR (neat, cm$^{-1}$): 3380 (br), 1685 (s), 1474 (w), 1388 (m), 1264 (w), 1090 (m), 1044 (m), 894 (w), 799 (w). HRMS (DART) ([M+H]$^+$) Calcd. for C11H17N2O7: 289.1030, found 289.1035.

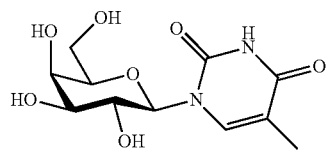

(D)-β-galactopyranosylthymine 3q (43): $[\alpha]^{20}_D$=+29° (c=1, H$_2$O). $^1$H NMR (400 MHz, D$_2$O) δ 8.46 (s, NH), 7.73 (s, 1H), 5.58 (d, J=9.1 Hz, 1H), 4.06 (d, J=3.3 Hz, 1H), 3.98-3.73 (m, 4H), 1.92 (s, 3H). $^{13}$C NMR (150 MHz, D$_2$O) δ 166.90, 152.79, 138.03, 112.68, 83.62, 78.63, 73.72, 69.38, 69.24, 61.51, 12.08. IR (neat, cm$^{-1}$): 3329 (br), 1690 (s), 1593 (m), 1475 (w), 1378 (w), 1286 (w), 1089 (m), 1066 (m), 780 (w). HRMS (DART) ([M+H]$^+$) Calcd. for C11H17N2O7: 289.1030, found 289.1027.

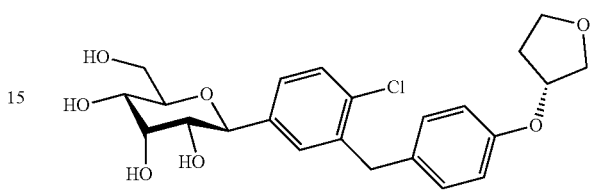

Allo-Empagliflozin 2r: Prepared according to the general reaction procedure B with the following changes: 5 mol % quinuclidine, MeCN/DMSO 3:1, 1.5 mL. Purified with general purification procedure A with the eluent from DCM/MeOH (0%-10%). DCM/MeOH=10:1, R$_f$=0.3. $[\alpha]^{20}_D$=+12° (c=1, MeOH). $^1$H NMR (400 MHz, MeOD) δ 7.37-7.29 (m, 3H), 7.13 (d, J=8.6 Hz, 2H), 6.81 (d, J=8.6 Hz, 2H), 4.99-4.96 (m, 1H), 4.46 (d, J=9.7 Hz, 1H), 4.11-3.99 (m, 3H), 3.96-3.86 (m, 5H), 3.74-3.68 (m, 2H), 3.59 (dd, J=9.6, 2.9 Hz, 1H), 3.46 (dd, J=9.6, 2.8 Hz, 1H), 2.22 (dtd, J=14.4, 8.4, 6.0 Hz, 1H), 2.12-2.06 (m, 1H). $^{13}$C NMR (100 MHz, MeOD) δ 155.82, 139.31, 138.24, 132.84, 132.11, 130.60, 129.56, 128.65, 126.87, 115.01, 77.14, 76.63, 76.06, 72.62, 72.46, 71.60, 67.75, 66.72, 61.97, 37.84, 32.46. IR (neat, cm$^{-1}$): 3367 (br), 2925 (m), 1611 (m), 1508 (s), 1240 (s), 1041 (s), 906 (w). HRMS (DART) ([M+H]$^+$) Calcd. for C23H28O7Cl: 451.1518, found 451.1502.

Effect of Different Hydrogen Atom Donors

General Procedures for the Screening of Different Hydrogen Atom Donors

Into a 1-dram vial, methyl (D)-α-methylglucose 1a (19.4 mg, 0.1 mmol), [Ir(dF(CF$_3$)ppy)$_2$(dtbbpy)]PF$_6$ (1.1 mg, 1 mol %), "H donor" (25 mol %), quinuclidine (1.1 mg, 10 mol %) and TBAOBz (9.1 mg, 25 mol %) were subsequently added. A 10×3 mm PTFE magnetic stir bar was added, and the vial was slightly capped and transferred into a nitrogen-filled purge box. Dry and degassed MeCN/DMSO (10/1 v/v, 0.5 mL) was added. The vial was then capped with a polypropylene screw cap with a bonded PTFE faced silicone liner and then removed from the purge box. The vial was immediately wrapped with parafilm. The reaction vessel was then placed in a 16-slot Aldrich® Micro Photoreactor (ALD-KIT001) with a blue LED and stirred at 300 rpm with a cooling fan overhead. After 22 hours, the crude reaction mixture was concentrated and analyzed by $^1$H NMR with 4-fluoroanisole as analytical standard. Note: Hydrogen donors that are liquid were added via a gas-tight syringe after the vial was transferred out from the purge box (vials equipped with a PTFE faced silicone septa, instead of a solid cap). The vial was removed from the purge box and connected to nitrogen via a needle. Then the hydrogen donor was added. The resulting solution was sparged with nitrogen for 2 minutes, then the outlet needle and nitrogen inlet needles were removed followed by sealing the vial with parafilm.

TABLE S1

The Effect of Different Hydrogen Atom Donors for Sugar Epimerization.

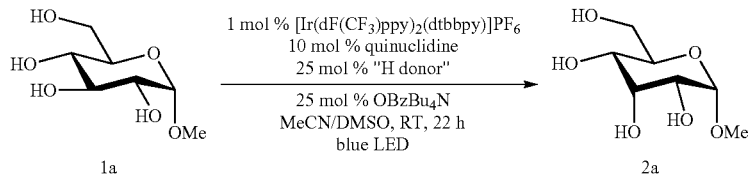

| Alkyl thiols | | Thiophenol/thiobenzoic acid | | Other "H" donors[a] | |
|---|---|---|---|---|---|
| "H" Donor | yield | "H" Donor | yield | "H" Donor | yield |
| 4-MeOBnSH | <1% | PhSH | 0% | $^i$Pr$_3$SiH | 0% |
| Mes-CH$_2$SH | <1% | 2,6-DiMeC$_6$H$_3$SH | 0% | (EtO)$_2$MeSiH | 0% |
| PhCH$_2$CH$_2$SH | 29% | 4-MeC$_6$H$_4$SH | 0% | Ph$_3$SiH | 0% |
| EtOC(O)CH$_2$CH$_2$SH | 17% | 4-$^t$BuMeC$_6$H$_4$SH | 0% | Bu$_3$SnH | 0% |
| nC$_6$H$_{13}$SH | 26% | 4-NH$_2$C$_6$H$_4$SH | 0% | 1,4-cyclohexadiene | 0% |
| nC$_{12}$H$_{25}$SH | 34% | 4-BrC$_6$H$_4$SH | 0% | succinimide | 0% |
| CySH | 38% | 4-NO$_2$C$_6$H$_4$SH | 0% | 9,1-dihydroanthracene | 0% |
| 1-Adamantanethiol | 52% | 4-CF$_3$C$_6$H$_4$SH | 0% | (EtO)$_2$P(O)H | 0% |
| tert-BuSH | 15% | PhC(O)SH | 0% | (PhO)$_2$P(O)H | 0% |
| L-cysteine | 6% | | | Et$_3$N BH$_3$ | 0% |
| Ph$_3$CSH | 0% | | | Py BH$_3$ | 0% |

[a]The reactions were carried out in the presence of 4CzIPN (1 mol%); "H donors" (50 mol %), quinuclidine (10 mol %) and d-ClOBzBu$_4$N (25 mol %).

Stern-Volmer Fluorescence Quenching Experiments

Stern-Volmer fluorescence quenching experiments were performed with freshly prepared stock solutions of [Ir(dFCF$_3$ppy)$_2$(dtbbpy)]PF$_6$ (0.02 mmol) or 4CzIPN (0.02 mmol) in MeCN/DMSO (v/v 10/1, 20 mL) at room temperature under nitrogen atmosphere. For each sample, the luminescence was acquired two times and averaged. The results are summarized in the FIGS. S2-S9 below.

The Epimerization Reaction in the Absence of Ad-SH

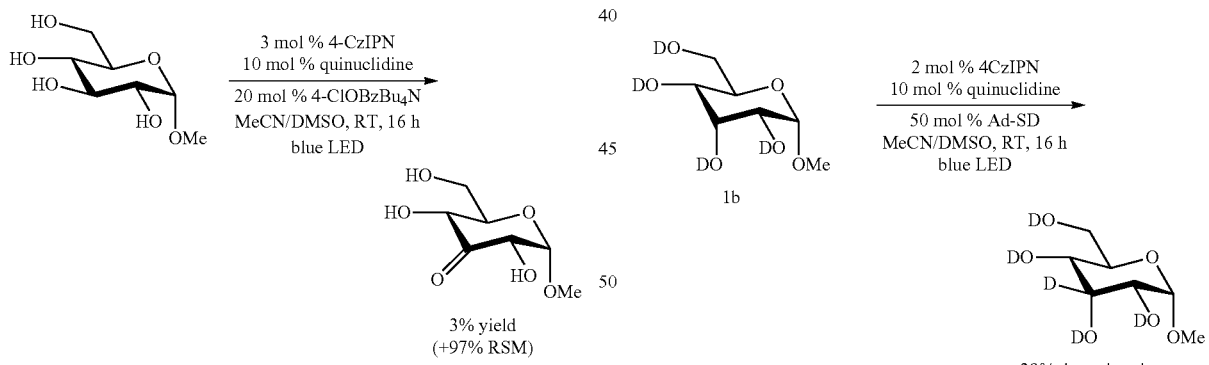

Into an oven-dried 1-dram vial, methyl α-D-glucopyranoside 1a (19.4 mg, 0.1 mmol), 4CzIPN (1.6 mg, 3 mol %), quinuclidine (1.1 mg, 10 mol %) and 4-ClOBzBu4N (9.9 mg, 25 mol %) were subsequently added. A 10×3 mm PTFE magnetic stir bar was added, and the vial was slightly capped and transferred into a nitrogen-filled purge box. After the injection of dry and degassed MeCN/DMSO (10/1 v/v, 0.5 mL). The vial was then capped with a polypropylene screw cap with a bonded PTFE faced silicone liner, and then removed from the purge box. The reaction vessel was then placed 5 cm from a blue LED Kessil lamp and stirred at 300 rpm with a cooling fan. After 16 hours, the crude reaction mixture was concentrated under reduced pressure, and analyzed by $^1$H NMR spectroscopy with 4-fluoroanisole as analytical standard. C3-oxidated product was isolated with column chromatography via a gradient eluent (DCM to DCM/MeOH 20/1). Known compound (32): $^1$H NMR (400 MHz, MeOD) δ 5.05 (d, J=4.2 Hz, 1H), 4.40 (dd, J=4.2, 1.5 Hz, 1H), 4.23 (dd, J=9.7, 1.3 Hz, 1H), 3.88 (dd, J=12.1, 2.1 Hz, 1H), 3.80 (dd, J=12.1, 4.6 Hz, 1H), 3.65 (ddd, J=9.7, 4.6, 2.1 Hz, 1H), 3.40 (s, 3H). $^{13}$C NMR (100 MHz, MeOD) δ 207.04, 103.82, 76.71, 76.05, 73.33, 62.46.

Deuterium-Labelling Experiment with Sugar 1b

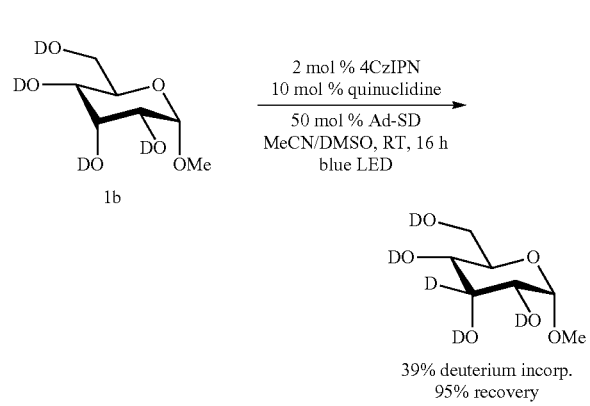

Into an oven-dried 1.5-dram vial, methyl α-D-allopyranoside 2a (19.4 mg, 0.1 mmol), 4CzIPN (1.6 mg, 2 mol %), quinuclidine (1.1 mg, 10 mol %) and 4-ClOBzBu4N (9.9 mg, 25 mol %) were subsequently added. The reaction mixture was dissolved in CD$_3$OD (1 mL) and evaporated off, this was repeated three times in order to exchange all the protic hydrogens into deuteriums. A PTFE magnetic stir bar was added, and the vial was slightly capped and transferred into a nitrogen-filled purge box. Then the vial was slightly capped and transferred into a nitrogen-filled purge box. 1-adamantanethiol-d1 (8.4 mg, 50 mol %) was added, followed by the injection of dry and degassed MeCN/DMSO (10/1 v/v, 0.5 mL). The vial was then capped with a polypropylene screw cap with a bonded PTFE faced silicone liner, and then removed from the purge box. The reaction vessel was then placed 5 cm from a blue LED Kessil lamp and stirred at 300 rpm with a cooling fan. After 16 hours, the crude reaction mixture was concentrated and analyzed by $^1$H NMR spectroscopy with 4-fluoroanisole as analytical standard. (Note: 1-adamantanethiol-d1 was prepared from 1-adamantanethiol by exchanging with $CD_3OD$ for three times (3×1 mL) and stored in the purge box).

Further Examples

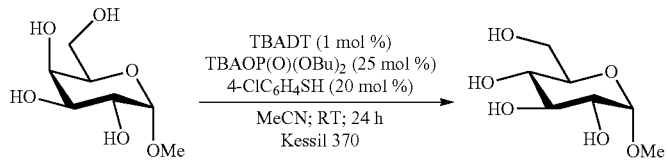

| entry | variations | yield | SM | M.B. |
|---|---|---|---|---|
| IV-134a | Tetrabutylammonium DT | 48% | 42% | 90% |
| IV-134b | Tetramethylammonium DT | 44% | 39% | 83% |
| IV-134c | Tetrapropylammonium DT | 54% | 29% | 83% |
| IV-132h | TMAB; no base | 2% | 85% | 87% |
| IV-132i | TPAB; no base | 15% | 65% | 80% |
| IV-132l | TBAB; no base | 23% | 67% | 90% |
| IV-132j | TMAB + base | 23% | 43% | 66% |
| IV-132k | TPAB + base | 41% | 26% | 67% |

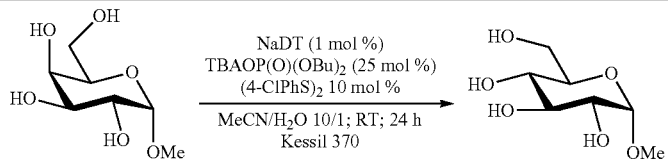

| Entry | (4-ClPhS)2 | yield | SM | MB. |
|---|---|---|---|---|
| IV-084a | 1 mol % TBADT | 49% | 32% | 81% |
| IV-096b | standard | 23% | 52% | 75% |
| IV-096a | 1 mol % NaDT; MeCN alone | 47% | 32% | 79% |
| IV-096i | 1 mol % NaDT; MeCN/H2O 5/1 | — | 95% | 95% |
| IV-096j | 1 mol % NaDT; MeCN/H2O 1/1 | 17% | 71% | 88% |
| IV-096c | 2 mol % NaDT | 31% | 20% | 51% |

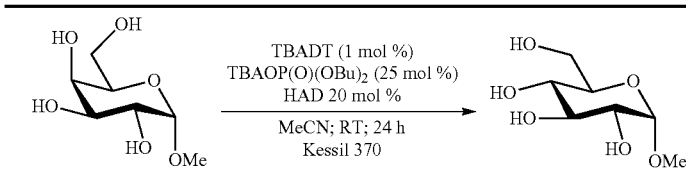

| entry | variations | Pka | BDE | σ | yield |
|---|---|---|---|---|---|
| 100a | 4-MeC$_6$H$_4$SH | 10.8 | 78 | −0.17 | 25% |
| 100b | 4-tBuC$_6$H$_4$SH | 10.2 | 81 | −0.20 | 20% |
| 100c | 4-MeOC$_6$H$_4$SH | | 77 | −0.27 | 31% |
| 100d | 3,4-diMeOC$_6$H$_3$SH | | | | 28% |
| 100h | 4-Ph-C$_6$H$_4$SH | | | −0.01 | 55% |
| 100f | 4-FC$_6$H$_4$SH | | 79 | 0.06 | 48% |
| 100g | 4-ClC$_6$H$_4$SH | 9.8 | 79 | 0.23 | 50% |
| 97e | 4-BrC$_6$H$_4$SH | | 79 | 0.23 | 44% |
| 100e | 4-CF$_3$OC$_6$H$_4$SH | | | 0.39 | 48% |
| 100j | 4-CF$_3$C$_6$H$_4$SH | | 81 | 0.54 | 53% |
| 100i | 4-NO$_2$C$_6$H$_4$SH | 5.5 | 81 | 0.78 | <5% |
| 100l | 3-NH$_2$C$_6$H$_4$SH | 11.4 | | −0.16 | 33% |
| 100k | 3-BrC$_6$H$_4$SH | 8.7 | 81 | 0.39 | 32% |
| 100m | 3-CF$_3$C$_6$H$_4$SH | 8.7 | 81 | 0.43 | 49% |

-continued

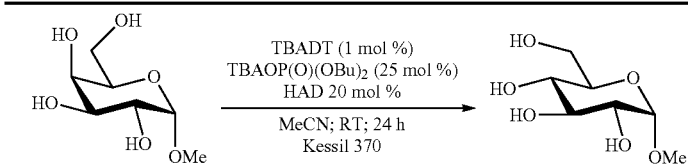

| entry | variations | Pka | BDE | σ | yield |
|---|---|---|---|---|---|
| 100p | 3,5-diClC$_6$H$_3$SH | 7.4 | | | 54% |
| 100n | 4,4'-HSC$_6$H$_4$-C$_6$H$_4$SH | | | | 54% |
| 100o | 2-ClC$_6$H$_4$SH | 8.9 | 80 | | 32% |
| 100q | C$_6$Cl$_5$SH | | 88 | | 40% |
| 100r | CySH | 17.7 | 87 | | 10% |
| 100s | EtO(O)CCH$_2$SH | 14.2 | ~86 | | 26% |
| 100t | (iPr)$_3$SiSH | — | | | 3% |
| 100u | Ph$_3$SiSH | — | | | 13% |
| 100v | MeC(O)SH | 3.33 | 87 | | 33% |

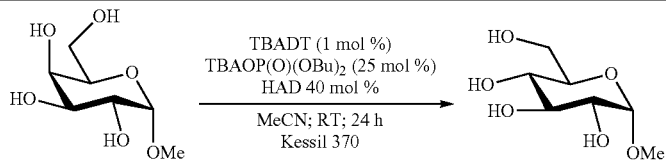

| entry | variations | yield | SM | M.B. |
|---|---|---|---|---|
| IV-103a | 4-ClC6H4SH | 58% | 16% | 74% |
| IV-103c | Sodium 3-mercapto-1-propanesulfonate | 5% | 85% | 90% |
| IV-103d | N-Acetyl-L-cysteine methyl ester | 24% | 81% | 105% |
| IV-103e | Boc-cysteamine | 22% | 63% | 85% |
| IV-103f | Sodium 2-mercaptoethanesulfonate | 6% | 81% | 87% |
| IV-103g | N-Acetyl-L-cysteine | 13% | 79% | 92% |
| IV-105f | Si(OMe)$_3$CH$_2$CH$_2$CH$_2$SH | 15% | 62% | 77% |
| IV-103h | HOCH$_2$CH$_2$SH | 22% | 67% | 89% |
| IV-103i | HO(O)CCH$_2$CH$_2$SH | 36% | 44% | 80% |
| IV-103j | p-Mentha-8-thiol-3-one | 11% | 69% | 80% |
| IV-103k | 2-,3-,10-Mercaptopinane | 22% | 50% | 72% |
| IV-100r | CySH | 10% | 68% | 78% |
| IV-100s | EtO(O)CCH$_2$SH | 26% | 54% | 80% |
| IV-100t | (iPr)$_3$SiSH | 3% | 77% | 80% |
| IV-100u | Ph$_3$SiSH | 13% | 77% | 90% |
| IV-100v | MeC(O)SH | 33% | 41% | 74% |
| IV-116a | 1-furanyl thiol | 18% | 71% | 89% |
| IV-116b | 1-dectane thiol | 16% | 74% | 90% |
| IV-116c | Ethane thiol | 19% | 71% | 90% |
| IV-116d | 1-octane thiol | 26% | 48% | 74% |
| IV-116e | 1,6-hexyl dithiols | 21% | 39% | 60% |

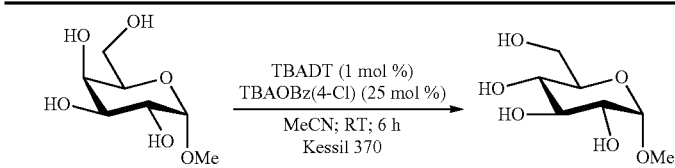

| entry | Conditions (10% (4-ClPhS)$_2$, 1 mol % TBADT, base 25 mol %) | Pdt Yield (SM yield) |
|---|---|---|
| IV-078a | TBABr + TBAOBz(4-Cl), 6 h | 32% (57%) |
| IV-078b | TBACl+ TBAOBz(4-Cl) , 6 h | 29% (57%) |

-continued

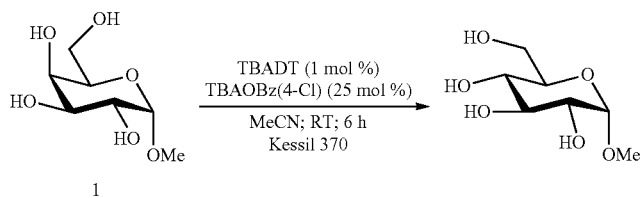

| entry | Conditions (10% (4-ClPhS)$_2$, 1 mol % TBADT, base 25 mol %) | Pdt Yield (SM yield) |
|---|---|---|
| IV-078c | TBABr, 6 h | 16% (71%) |
| IV-078d | TBACl, 6 h | 23% (58%) |
| IV-079j | (TBA)$_2$SO$_4$, 20 h | 22% (51%) |
| IV-079k | TBAClO$_4$, 20 h | 0% (90%) |
| IV-079l | TMANO$_3$, 20 h | 0% (99%) |
| IV-079m | TEAOTs, 20 h | 0% (92%) |
| IV-077p | TBAOP(O)(OBu)$_2$, 18 h | 60% (23%) |
| IV-077q | TBAOP(O)(OBu)$_2$, 36 h | 58% (5%) |
| IV-079a | TBAOP(O)(OBu)$_2$, silica, 20 h | 57% (17%) |
| IV-079b | TBAOP(O)(OBu)$_2$, Al2O3, 20 h | 52% (25%) |
| IV-079c | TBAOP(O)(OBu)$_2$, IRA-900, 20 h | 0% (88%) |
| IV-079d | TBAOP(O)(OBu)$_2$, M.S., 20 h | 48% (32%) |
| IV-072a2 | TBAOP(O)(OBu)$_2$ | 47% |
| IV-072b2 | Cs$_2$CO$_3$ | 5% |
| IV-072c2 | K$_2$CO$_3$ | 9% |
| IV-072d2 | Na$_2$CO$_3$ | 14% |
| IV-072e2 | K$_3$PO$_4$ | 1% |
| IV-073a1 | TBAOBz; 15 h | 38% |
| IV-073b1 | TBAOBz(4-Cl); 15 h | 47% |
| IV-073c1 | TBAOBz(4-F); 15 h | 38% |
| IV-073d1 | TBAOBz(4-I); 15 h | 25% |
| IV-073e1 | TBAOBz(4-CF$_3$); 15 h | 36% |
| IV-073f1 | TBAOBz(4-MeO); 15 h | 28% |
| IV-073g1 | TBAOBz(3-MeO); 15 h | 39% |
| IV-073h1 | TBAOBz(4-CN); 15 h | 8% |
| IV-073i1 | TBAOBz(4-NO$_2$); 15 h | 44% |
| IV-072f2 | Quinuclidine | <1% |
| IV-072g2 | DBU | <1% |
| IV-073j1 | DABCO | <1% |
| IV-073k1 | DMAP | <1% |
| IV-073l1 | tBubbpy | 13% |

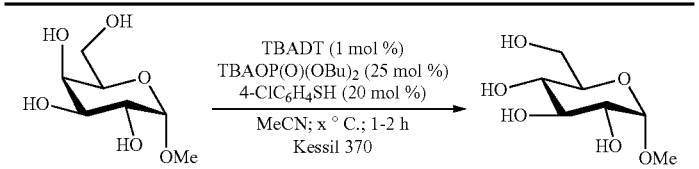

| entry | variations | yield | SM | M.B. |
|---|---|---|---|---|
| IV-132e | RT; 1 h | 10% | 76% | 86% |
| IV-132f | RT; 2 h | 16% | 69% | 85% |
| IV-132a | 50° C.; 1 h | 10% | 79% | 89% |
| IV-132b | 50° C.; 2 h | 18% | 64% | 82% |
| IV-132c | 70° C.; 1 h | 11% | 77% | 88% |
| IV-132d | 70° C.; 2 h | 18% | 70% | 88% |

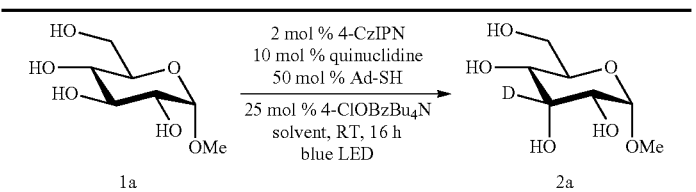

| Entry | Variations | Yield | D-incorporation | RSM |
|---|---|---|---|---|
| III-120a | MeCN/CD$_3$OD 1/1 | 29% | 22% (76%) | 69% |
| III-120b | MeCN/CD$_3$OD 1/1; pretreated the reaction solid with CD$_3$OD (0.5 mL × 1) | 29% | 27% (93%) | 70% |
| III-120c | MeCN/CD$_3$OD 1/1; 1-Ad-SD; pretreated the reaction solid with CD$_3$OD (0.5 mL × 1) | 26% | 24% (92%) | 73% |
| III-128a | MeCN/CD$_3$OD 2/1 | 50% | 33% (66%) | 31% |
| III-128b | MeCN/CD$_3$OD 10/1 | 57% | 26% (46%) | 27% |
| III-122a | MeCN/D$_2$O 10/1; pretreated the reaction solid with CD$_3$OD (0.5 mL × 1) | 24% | 21% (88%) | 51% |
| III-122b | MeCN/D$_2$O 5/1; pretreated the reaction solid with CD$_3$OD (0.5 mL × 1) | 19% | 17% (89%) | 63% |
| III-122c | MeCN/D$_2$O 1/1 | — | — | >99% |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A method of deoxygenating a pyranose monosaccharide or a pyranose saccharide residue in an oligosaccharide or a glycoside, represented by the following scheme:

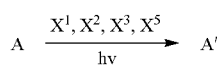

wherein,
A is a pyranose monosaccharide or a pyranose saccharide residue in an oligosaccharide or a glycoside;
A' is a dehydrated isomer of A; wherein A' comprises a —C(O)—CH$_2$— moiety at a location that is —CH(OH)—CH(OH)— in A;
X$^1$ is a photocatalyst;
X$^2$ is a base or absent;
X$^3$ is an alkyl thiol;
X$^5$ is a Lewis acid; and
hv is light.

2. The method of claim 1, wherein:
X$^1$ is:

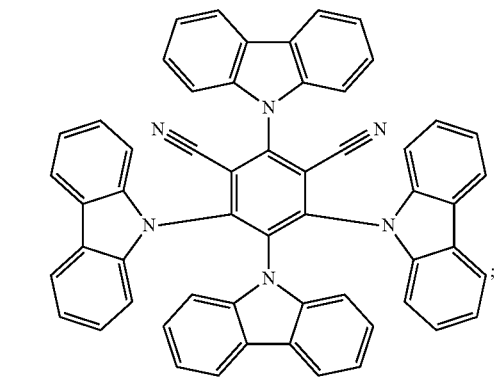 [SMILES: N#Cc1c(-n2c3ccccc3c3ccccc32)c(C#N)c(-n2c3ccccc3c3ccccc32)c(-n2c3ccccc3c3ccccc32)c1-n1c2ccccc2c2ccccc21]

X$^2$ is quinuclidine;
X$^3$ is adamantanethiol; and
hv is blue light.

3. A method of forming an epimer of a pyranose monosaccharide or a pyranose saccharide residue in an oligosaccharide or a glycoside, represented by the following scheme:

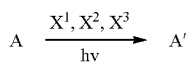

wherein,

A is a pyranose monosaccharide or a pyranose saccharide residue in an oligosaccharide or a glycoside;

A' is an epimer of A, wherein the stereochemical configuration of a chiral center bearing a hydroxyl moiety in A' is inverted relative to the stereochemical configuration of the chiral center in A;

$X^1$ is a photocatalyst;

$X^2$ is an amine;

$X^3$ is an alkyl thiol; and hv is light.

4. The method of claim 3, wherein $X^1$ has a structure represented by formula I:

I wherein, $R^1$, $R^2$, $R^3$, $R^4$, $R^5$, and $R^6$ are each independently selected from the group consisting of H, alkyl, halo, hydroxyl, carboxyl, acyl, ester, thioester, alkoxy, amino, amido, cyano, nitro, azido, alkylthio, alkenyl, alkynyl, cycloalkyl, heterocyclylalkyl, heteroaralkyl, sulfonamide, aryl, heteroaryl, heterocyclyl, and aralkyl.

5. The method of claim 4, wherein $X^1$ is:

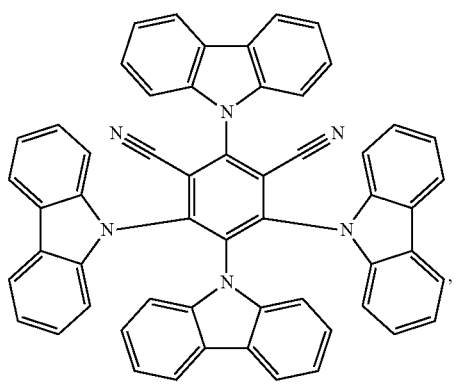

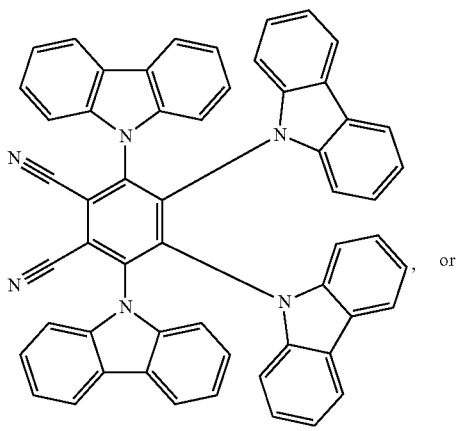

, or

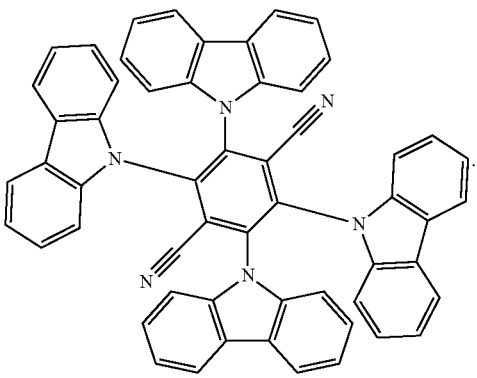

6. The method of claim 3, wherein $X^1$ has a structure represented by formula II:

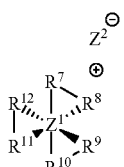

II wherein, each of $R^7$, $R^8$, $R^9$, $R^{10}$, $R^{11}$ and $R^{12}$ is independently aryl or heteroaryl;

$Z^1$ is a transition metal; and $Z^2$ is a non-coordinating anion.

7. The method of claim 6, wherein $X^1$ is

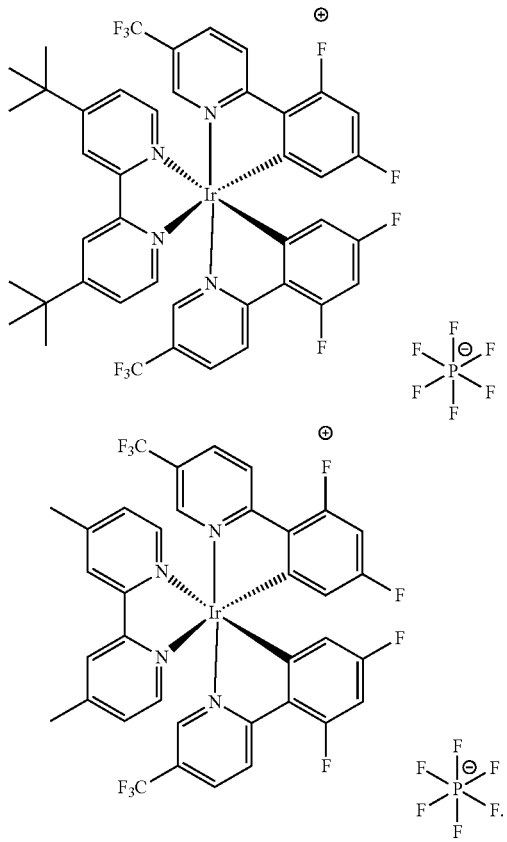

8. The method of claim 3, wherein $X^1$ is a tungstate.

9. The method of claim 8, wherein $X^1$ is sodium tungstate.

10. The method of claim 8, wherein $X^1$ is tetra-n-methylammonium decatungstate (TMADT), tetra-n-propylammonium decatungstate (TPADT), or tetra-n-butylammonium decatungstate (TBDAT).

11. The method of claim 3, wherein $X^2$ is an alkyl amine or a heterocyclic amine.

12. The method of claim 3, wherein $X^3$ is adamantanethiol.

13. The method of claim 3, wherein the method further comprises a base.

14. The method of claim 13, wherein the base is an organic base.

15. The method of claim 13, wherein the base has a structure represented by formula III:

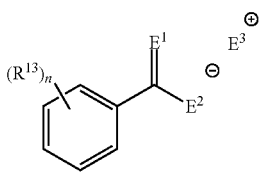

wherein, $E^1$ and $E^2$ are each independently selected from the group consisting of O and S;

$E^3$ is an alkali metal cation, an alkaline earth metal cation, or a quaternary alkylammonium cation;

$R^{13}$ is independently for each occurrence alkyl, heteroalkyl, halo, hydroxyl, carboxyl, acyl, ester, thioester, alkoxy, amino, amido, cyano, nitro, azido, alkylthio, alkenyl, alkynyl, cycloalkyl, heterocyclylalkyl, heteroaralkyl, sulfonamide, aryl, heteroaryl, heterocyclyl, or aralkyl; and n is 0-5.

16. The method of claim 3, wherein hv is blue light or white light.

17. The method of claim 3, wherein the method is performed at ambient conditions.

18. The method of claim 3, wherein the method further comprises a deuterated solvent and the method replaces a hydrogen at the site of epimerization with a deuterium.

19. The method of claim 3, wherein the yield of A' is greater than 25%, greater than 30%, greater than 40%, greater than 50%, greater than 60%, greater than 70%, greater than 80%, greater than 90%, greater than 95%, or greater than 99%.

20. The method of claim 3, wherein $X^1$ is:

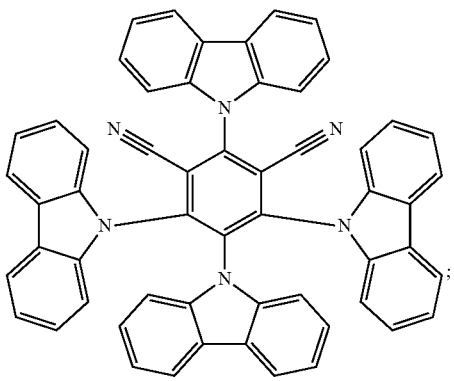 [SMILES: N#Cc1c(-n2c3ccccc3c3ccccc32)c(C#N)c(-n2c3ccccc3c3ccccc32)c(-n2c3ccccc3c3ccccc32)c1-n1c2ccccc2c2ccccc21]

$X^2$ is quinuclidine;
$X^3$ is adamantanethiol; and
hv is blue light.

* * * * *